(12) United States Patent
He et al.

(10) Patent No.: US 8,497,368 B2
(45) Date of Patent: Jul. 30, 2013

(54) HETEROCYCLIC HYDRAZONE COMPOUNDS

(75) Inventors: Feng He, Shanghai (CN); Miao Dai, Shanghai (CN); Xingnian Fu, Lanzhou (CN); Yue Li, Shanghai (CN); Lei Liu, Shanghai (CN); Yuan Mi, Shanghai (CN); Yao-chang Xu, Shanghai (CN); Guoliang Xun, Taicang (CN); Zhengtian Yu, Shanghai (CN); Ji Yue Zhang, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/389,912

(22) PCT Filed: Aug. 10, 2010

(86) PCT No.: PCT/EP2010/061609
§ 371 (c)(1),
(2), (4) Date: Feb. 10, 2012

(87) PCT Pub. No.: WO2011/018454
PCT Pub. Date: Feb. 17, 2011

(65) Prior Publication Data
US 2012/0142681 A1  Jun. 7, 2012

Related U.S. Application Data

(60) Provisional application No. 61/233,328, filed on Aug. 12, 2009.

(30) Foreign Application Priority Data

Apr. 21, 2010 (WO) ................ PCT/CN2010/071981
Jun. 18, 2010 (WO) ................ PCT/CN2010/074078

(51) Int. Cl.
| C07D 487/04 | (2006.01) |
| A61K 31/4985 | (2006.01) |
| A61P 35/00 | (2006.01) |
| A61P 19/02 | (2006.01) |

(52) U.S. Cl.
USPC .......................................... 544/236; 514/248

(58) Field of Classification Search
USPC .......................................... 544/236; 514/248
See application file for complete search history.

(56) References Cited

U.S. PATENT DOCUMENTS

| 6,087,374 | A | 7/2000 | Schladetzky et al. |
| 6,346,534 | B1 | 2/2002 | Zhu et al. |
| 7,572,807 | B2 | 8/2009 | Li et al. |
| 7,732,604 | B2 | 6/2010 | Cheng et al. |
| 8,071,581 | B2 | 12/2011 | Smith et al. |
| 8,389,526 | B2 | 3/2013 | Furet et al. |
| 8,410,264 | B2 | 4/2013 | Dai et al. |
| 2005/0070542 | A1 | 3/2005 | Hodgetts et al. |
| 2009/0124609 | A1 | 5/2009 | Albrecht et al. |
| 2009/0258855 | A1 | 10/2009 | Bounaud et al. |
| 2009/0264406 | A1 | 10/2009 | Furet et al. |
| 2012/0302570 | A1 | 11/2012 | Dai et al. |

FOREIGN PATENT DOCUMENTS

| JP | 2009203214 | | 9/2009 |
| WO | 01/83481 | A1 | 11/2001 |
| WO | 2005/004607 | A1 | 1/2005 |
| WO | 2005/010005 | A1 | 2/2005 |
| WO | 2006/101456 | A1 | 9/2006 |
| WO | 2007/064797 | A2 | 6/2007 |
| WO | 2007/075567 | A1 | 7/2007 |
| WO | 2007/132308 | A1 | 11/2007 |
| WO | 2007/138472 | A2 | 12/2007 |
| WO | 2008/003753 | A1 | 1/2008 |
| WO | 2008/064157 | A1 | 5/2008 |
| WO | 2008/116898 | A1 | 10/2008 |
| WO | 2009/106577 | A1 | 9/2009 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Mass, R. D., Int. J. Radiation Oncology Bio. Phys. vol. 58(3): 932-940, 2004.*
Fabbro et al. Pharmacology & therapeutics 93, 79-98, 2002.*
Hulikal, V. Deuterium Labeled Compounds in Drug Discovery Process, 2010. Abstract provided-see also www. hwb.gov.in/htmldocs/nahwd201 O/L15.pdf.*
Coumar, Mohane Selvaraj et al., "Structure-Based Drug Design of Novel Aurora Kinase A Inhibitors: Structural Basis for Potency and Specificity" J. Med. Chem., vol. 52, Issue 4, pp. 1050-1062, 2009.
U.S. Appl. No. 13/613,291, filed Sep. 13, 2012.

* cited by examiner

*Primary Examiner* — Venkataraman Balasubramanian
(74) *Attorney, Agent, or Firm* — Laura K. Madden

(57) ABSTRACT

The invention relates to compounds of formula (I) and salts thereof: wherein the substituents are as defined in the specification; a compound of formula (I) for use in the treatment of the human or animal body, in particular with regard to c-Met tyrosine kinase mediated diseases or conditions; the use of a compound of formula (I) for manufacturing a medicament for the treatment of such diseases; pharmaceutical compositions comprising a compound of the formula (I), optionally in the presence of a combination partner, and processes for the preparation of a compound of formula (I).

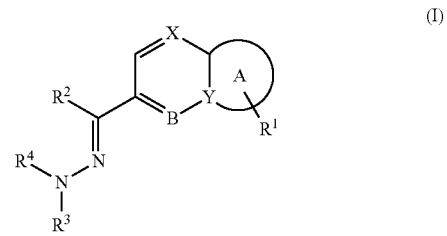

(I)

18 Claims, No Drawings

HETEROCYCLIC HYDRAZONE COMPOUNDS

The invention relates to bicyclic compounds of formula (I) and salts thereof, the uses of such compounds to treat the human or animal body, in particular with regard to a proliferative disease, pharmaceutical compositions comprising such compounds, combinations comprising a compound of formula (I), and processes for the preparation of such compounds.

The Hepatocyte Growth Factor Receptor, herein referred to as c-Met, is a receptor tyrosine kinase that has been shown to be over-expressed and/or genetically altered in a variety of malignancies, specifically, gene amplification and a number of c-Met mutations are found in various solid tumors, see e.g. WO2007/126799. Further, the receptor tyrosine kinase c-Met is involved in the processes of migration, invasion and morphogenesis that accompany embryogenesis and tissue regeneration. C-met is also involved in the process of metastasis. Several lines of evidence have indicated that c-Met plays a role in tumor pathogenesis. Gain of function germ line mutations in c-Met is associated with development of hereditary papillary renal cell carcinoma (PRCC). Amplification or mutations in c-Met have also been reported in sporadic forms of PRCC, in head and neck squamous cell carcinoma, in gastric carcinoma, in pancreatic carcinoma and in lung cancer. Such alterations have been shown in selected instances to confer dependence of the tumor on c-Met and/or resistance to other targeted therapies. Elevated levels of c-Met, together with its unique ligand HGF/SF, are observed at high frequency in multiple clinically relevant tumors. A correlation between increased expression and disease progression, metastases and patient mortality has been reported in several cancers, including bladder, breast, squamous cell carcinoma and gastric carcinoma as well as leiomyosarcoma and glioblastoma.

WO 2008/008539 discloses certain fused heterocyclic derivatives which are useful in the treatment of HGF mediated diseases. WO 2007/013673 discloses fused heterocyclic derivatives as Lck inhibitors which are useful as immunosuppressive agents. EP0490587 discloses certain pyrazolopyrimidines which are useful as angiotensin II antagonists. The disclosures of the publications cited in this specification are herein incorporated by reference.

It is an aim of the present invention to provide further compounds that modulate, and in particular inhibit, c-Met. It has now been found that the compounds of the formula (I) described herein are inhibitors of c-Met and have a number of therapeutic applications. For example, the compounds of formula (I) are suitable for use in the treatment of diseases dependent on c-Met activity, especially solid tumors or metastasis derived therefrom. Through the inhibition of c-Met, compounds of the invention also have utility as anti-inflammatory agents, for example for the treatment of an inflammatory condition which is due to an infection.

Preferably, the compounds of the invention are metabolically stable, posses favourable pharmacokinetic properties, are non-toxic and demonstrate few side-effects. In addition, preferred compounds of the invention exist in a physical form that is stable, non-hygroscopic and easily formulated. A preferred aspect of the invention is directed to compounds of formula (I) having an activity that is superior to the activity of compounds of the prior art. Another preferred aspect of the invention is directed to compounds of formula (I) having have good kinase selectivity.

The present invention relates to a compound of the formula (I),

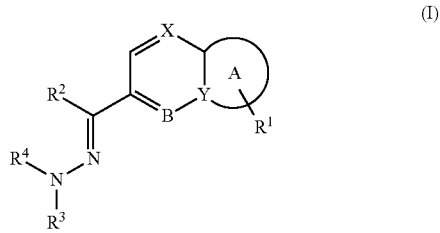

wherein
Y is C or N;
X is CH or N;
B is CH or N;
A is a ring;
such that when X is CH and B is N, ring A is ring Ai or ring Aii;

when X is N and B is N, ring A is Aiii;

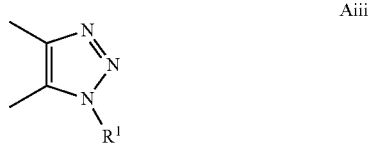

and when X is N and B is N, or X is N and B is CH, ring A is Ai;

$R^1$ is a group selected from i, ii and iii:

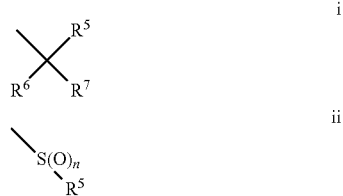

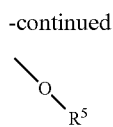

wherein $R^5$ is heteroaryl$^1$;

$R^6$ is hydrogen, deuterium, OH, methyl or halo;

$R^7$ is hydrogen, deuterium, halo, or $(C_1-C_3)$alkyl, wherein said $(C_1-C_3)$alkyl is optionally substituted by one or more substituents independently selected from OH and halo; or $R^6$ and $R^7$, together with the carbon to which they are attached form cyclopropyl, wherein said cyclopropyl is optionally substituted by methyl;

n is 0, 1 or 2;

$R^2$ is hydrogen, $NH_2$, or $(C_1-C_4)$alkyl, wherein said $(C_1-C_4)$alkyl is optionally substituted by one or more substituents independently selected from OH, $NH_2$ and halo;

$R^3$ is hydrogen, —$CONH_2$, —$CONH(C_1-C_4)$alkyl, —CONHphenyl, wherein the phenyl of said CONHphenyl is optionally substituted by one or more halo, —$(C_1-C_4)$alkyl, —$CO(C_1-C_4)$alkyl, —$CO_2(C_1-C_4)$alkyl, phenyl, heteroaryl$^2$, —COheteroaryl$^2$, —$CSNH_2$, —$CSNH(C_1-C_4)$alkyl, —CS-NHbenzyl, —$SO_2(C_1-C_4)$alkyl or —$COCH_2$heterocyclyl$^1$, said heterocyclyl$^1$ being optionally substituted by $(C_1-C_3)$alkyl;

$R^4$ is hydrogen or $(C_1-C_3)$alkyl;

or $R^3$ and $R^4$ together with the nitrogen to which they are attached form a 5 or 6 membered saturated or partially unsaturated monocyclic group comprising 1 ring N atom to which $R^3$ and $R^4$ are attached and optionally 1 additional ring heteroatom independently selected from N, O and S, wherein said monocyclic group is substituted by one or two =O substituents;

or a pharmaceutically acceptable salt thereof.

The following general definitions shall apply in this specification, unless otherwise specified:

A "compound of the invention", or "compounds of the invention", or "a compound of the present invention" means a compound or compounds of formula (I) as described herein.

As used herein, the terms "including", "containing" and "comprising" are used herein in their open, non-limiting sense.

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

"Treatment" includes prophylactic (preventive) and therapeutic treatment as well as the delay of progression of a disease, disorder or condition.

Any non-cyclic carbon containing group or moiety with more than 1 carbon atom is straight-chain or branched. "Alkyl" refers to a straight-chain or branched-chain alkyl group. For example, $(C_1-C_4)$alkyl includes methyl, ethyl, n- or iso-propyl, and n-, iso-, sec- or tert-butyl.

"heteroaryl$^1$" means a 9- or 10-membered, unsaturated or partially unsaturated bicyclic group comprising 1, 2, 3 or 4 ring heteroatoms independently selected from N, O and S, wherein the total number of ring S atoms does not exceed 1, and the total number of ring O atoms does not exceed 1.

Heteroaryl$^1$ is optionally substituted by one or more substituents, preferably 1, 2 or 3 substituents, independently selected from halo, OH, and $(C_1-C_3)$alkyl, wherein said $(C_1-C_3)$alkyl is optionally substituted by one or more substituents independently selected from OH and halo.

Specific examples of heteroaryl$^1$ include, but are not limited to, quinolinyl, isoquinolinyl, cinnolinyl, quinazolinyl, quinoxalinyl, phthalazinyl, 1,5-naphthyridinyl, 1,6-naphthyridinyl, 1,7-naphthyridinyl, 1,8-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, benzofuranyl, benzothiophenyl, indolyl, benzimidazolyl, benzoxazolyl, indazoyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolizinyl, imidazo[1,2-a]pyridinyl, imidazo[1,5-a]pyridinyl, pyrazolo[1,5-a]pyridinyl, pyrrolo[1,2-b]pyridazinyl and imidazo[1,2-c]pyrimidinyl, and the partially saturated equivalents thereof.

"heteroaryl$^2$" means a 5- to 10-membered unsaturated or partially unsaturated monocyclic or bicyclic group comprising 1, 2, 3 or 4 ring heteroatoms independently selected from N, O and S, wherein the total number of ring S atoms does not exceed 1, and the total number of ring O atoms does not exceed 1. Heteroaryl$^2$ is optionally substituted by one or more substituents independently selected from halo, OH, and $(C_1-C_3)$alkyl, wherein said $(C_1-C_3)$alkyl is optionally substituted by one or more substituents independently selected from OH and halo. Specific examples of heteroaryl$^2$ include, but are not limited to, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, quinolinyl, isoquinolinyl, cinnolinyl, quinazolinyl, quinoxalinyl, azaquinoxalinyl, phthalazinyl, 1,5-naphthyridinyl, 1,6-naphthyridinyl, 1,7-naphthyridinyl, 1,8-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, benzofuranyl, benzothiophenyl, indolyl, benzimidazolyl, benzoxazolyl, indazoyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolizinyl, imidazo[1,2-a]pyridinyl, imidazo[1,5-a]pyridinyl, pyrazolo[1,5-a]pyridinyl, pyrrolo[1,2-b]pyridazinyl and imidazo[1,2-c]pyrimidinyl, and partially saturated cyclic groups, such as 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

"heterocyclyl$^1$" means a 5 or 6 membered saturated or partially unsaturated monocyclic group comprising 1 or 2 ring heteroatoms independently selected from N, O and S. Specific examples of heterocyclyl$^1$ include, but are not limited to, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl and 1,4-azathianyl.

"heteroaryl$^3$" means a 9- or 10-membered, unsaturated or partially unsaturated bicyclic group comprising 1 or 2 ring N heteroatoms. Heteroaryl³ is optionally substituted by one or more substituents independently selected from halo, OH, and (C₁-C₃)alkyl, wherein said (C₁-C₃)alkyl is optionally substituted by one or more substituents independently selected from OH and halo. Specific examples of heteroaryl³ include, but are not limited to, quinolinyl, isoquinolinyl, cinnolinyl, azaquinazolinyl, quinoxalinyl, phthalazinyl, 1,5-naphthyridinyl, 1,6-naphthyridinyl, 1,7-naphthyridinyl, 1,8-naphthyridinyl, 2,6-naphthyridinyl, 2,7-naphthyridinyl, indolyl, benzimidazolyl, indazolyl, pyrrolo[2,3-b]pyridinyl, pyrrolo[2,3-c]pyridinyl, pyrrolo[3,2-c]pyridinyl, pyrrolo[3,2-b]pyridinyl, isoindolyl, indazolyl, indolininyl, imidazo[1,2-a]pyridinyl, imidazo[1,5-a]pyridinyl, pyrazolo[1,5-a]pyridinyl and pyrrolo[1,2-b]pyridazinyl.

heteroaryl⁴ means a 5 or 6 membered unsaturated or partially unsaturated monocyclic group comprising 1, 2, 3 or 4 ring heteroatoms independently selected from N, O and S, wherein the total number of ring S atoms does not exceed 1, and the total number of ring O atoms does not exceed 1. Specific examples of heteroaryl⁴ include, but are not limited to, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

In a preferred embodiment, heteroaryl⁴ means a 5 or 6 membered unsaturated monocyclic group comprising 1 or 2 ring N heteroatoms. Specific examples of this preferred embodiment include, but are not limited to pyrrolyl, pyrazolyl, imidazolyl, pyridinyl, pyridazinyl, pyrimidinyl and pyrazinyl.

"disease" as used herein includes a disorder or condition.

According to the disclosures herein, the compound of formula (I) is selected from any one of the following structures (Ia) to (Ie):

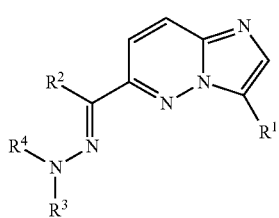
(Ia)

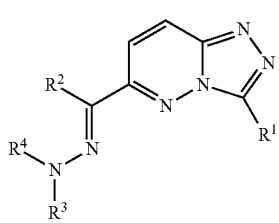
(Ib)

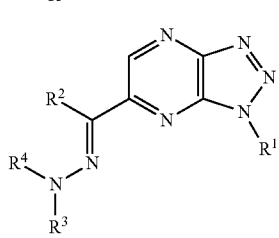
(Ic)

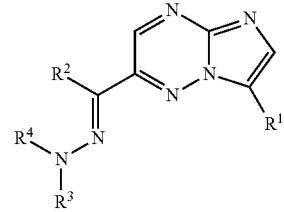
(Id)

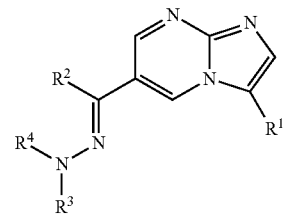
(Ie)

In an embodiment of the invention, there is provided a compound of formula (I) wherein
B is N;
Y is C or N;
X is CH or N;
such that when X is CH, ring A is ring Ai or ring Aii

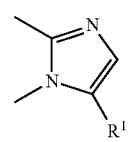
Ai

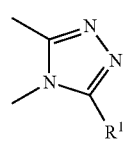
Aii when X is N, ring A is Aiii;

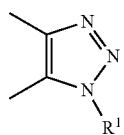
Aiii and when X is N and B is CH, ring A is Ai.

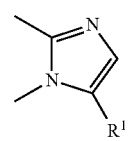
Ai

Such compounds have the structure (Ia), (Ib), (Ic) or (Ie) as disclosed herein.

In another embodiment of the invention, there is provided a compound of formula (I) wherein
B is N;
Y is C or N;

X is CH or N; such that when X is CH, ring A is ring Ai or ring Aii

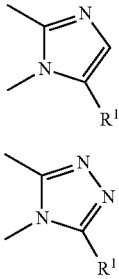

Ai

Aii and when X is N, ring A is Aiii;

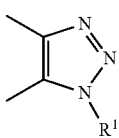

Aiii

Such compounds have the structure (Ia), (Ib) or (Ic) as disclosed herein

In another embodiment of the invention, $R^1$ is i or ii:

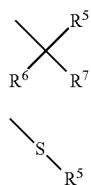

i ii

In a preferred embodiment of the invention, $R^1$ is:

i

In another embodiment of the invention, $R^1$ is a group selected from i, ii and iii:

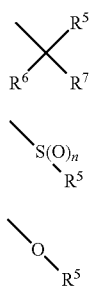

i ii iii and $R^5$ is heteroaryl$^3$.

In another preferred embodiment of the invention, $R^1$ is i:

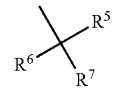

i and $R^5$ is heteroaryl$^3$.

In another embodiment of the invention, heteroaryl$^1$ and heteroaryl$^3$ are each optionally substituted by one or more substituents independently selected from halo, OH, and ($C_1$-$C_3$)alkyl. In particular, heteroaryl$^1$ and heteroaryl$^3$ are each optionally substituted by one, two or three substituents independently selected from halo and ($C_1$-$C_2$)alkyl.

In a preferred embodiment of the invention, $R^5$ is indazolyl or quinolinyl, optionally substituted by one or more substituents independently selected from halo and ($C_1$-$C_3$)alkyl. In particular, $R^5$ is indazolyl or quinolinyl optionally substituted by one, two or three substituents independently selected from halo and ($C_1$-$C_3$)alkyl.

In a further preferred embodiment of the invention, $R^5$ is indazolyl optionally substituted by one, two or three substituents independently selected from methyl and fluoro, or $R^5$ is quinolinyl optionally substituted by one or two fluoro substituents.

In a particular embodiment of the invention, $R^5$ is indazol-5-yl substituted at the 1 position by a methyl substituent and optionally further substituted one or two fluoro substituents, or $R^5$ is quinolin-6-yl optionally substituted by one or two fluoro substituents.

In another embodiment of the invention, $R^6$ is hydrogen, deuterium, OH or halo, particularly hydrogen, deuterium or halo, and in a preferred embodiment, $R^6$ is hydrogen.

In another embodiment of the invention, $R^7$ is hydrogen, deuterium, halo, or methyl, wherein said methyl is optionally substituted by one or more substituents independently selected from OH and halo. In another embodiment of the invention $R^7$ is hydrogen, deuterium, halo, or methyl. In a preferred embodiment, $R^7$ is hydrogen.

Where $R^1$ is i, and $R^6$ and $R^7$ are not both hydrogen, the compound of formula (I) contains an asymmetric carbon atom at $R^1$. Included within the scope of the invention is a compound of formula (I) containing the (R), or the (S) enantiomer of $R^1$i, or a mixture thereof. In a preferred embodiment of the invention there is provided a compound of formula (I) containing the (S) enantiomer of $R^1$i, or a mixture including the (S) enantiomer as a major component.

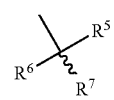

i

In another embodiment of the invention, $R^1$ is selected from fluoroquinolinylmethyl-, fluoroquinolinylmethyl-d-, fluoroquinolinylmethyl-d2-, quinolinylmethyl-, difluoroquinolinylmethyl-, fluoroquinolinylhydroxymethyl-, quinolinylhydroxymethyl-, difluoroquinolinylhydroxymethyl-, fluoroquinolinylhydroxyethyl-, quinolinylhydroxyethyl-, fluoroquinolinylethyl-, quinolinylethyl-, 4,6-difluoro-1-methylindazolylethyl-, 4,6-difluoro-1-methylindazolylmethyl-, difluoro(quinolinyl)methyl-, quinolinylpropanyl-, difluoroquinolinylethyl-, quinolinylcyclopropyl-, 6-fluoro-1-methylindazolylethyl-, 6-fluoro-1-methyl-indazolylmethyl-, 1-methylindazolylmethyl-, and 1-methylindazolylethyl-.

In a preferred embodiment of the invention n is 0.

In another embodiment of the invention, $R^2$ is hydrogen or methyl. Preferably, $R^2$ is methyl.

In another embodiment of the invention, $R^3$ is hydrogen, —$CONH_2$, —$CONHCH_3$, —CONHphenyl, wherein the phenyl of said CONHphenyl is optionally substituted by one or more halo, —($C_1$-$C_4$)alkyl, —$COCH_3$, —$CO_2CH_3$, phenyl, benzoxazolyl, heteroaryl[4], —COheteroaryl[4], —$CSNH_2$, —CSNH($C_1$-$C_2$)alkyl, —CSNHbenzyl, —$SO_2$Me, —$COCH_2$-morpholinyl, $COCH_2$piperidinyl, or —$COCH_2$piperazinyl, said piperazinyl being optionally substituted by one or more ($C_1$-$C_3$)alkyl;

In a further embodiment of the invention, $R^3$ is hydrogen, —$CONH_2$, —$CONHCH_3$, —CONHphenyl, wherein the phenyl of said CONHphenyl is optionally substituted by one or more halo, —($C_1$-$C_4$)alkyl, —$COCH_3$, —$CO_2CH_3$, phenyl, pyridinyl, benzoxazolyl, —COpyridinyl, —$CSNH_2$, —CSNH($C_1$-$C_2$)alkyl, —CSNHbenzyl, —$SO_2$Me, —$COCH_2$-morpholine, or —$COCH_2$piperazine, wherein the piperazine of said —$COCH_2$piperazine is optionally substituted at the 4 position by methyl;

In a preferred embodiment of the invention, $R^3$ is —$CONH_2$.

In another preferred embodiment of the invention, $R^4$ is hydrogen or methyl, more preferably hydrogen.

In an alternative embodiment of the invention, $R^3$ and $R^4$ together with the nitrogen to which they are attached form oxazolidinone, oxazolidinedione, imidazolidinone or imidazolidinedione.

Halo means fluoro, chloro, bromo or iodo. In a particular embodiment of the invention, halo is fluoro or chloro. Preferably, halo is fluoro.

The present invention relates to a compound of the formula (I),

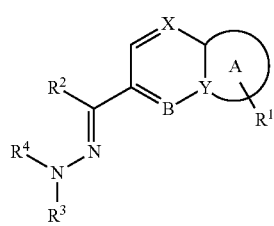

wherein
Y is C or N;
X is CH or N;
B is CH or N;
A is a ring;
such that when X is CH and B is N, ring A is ring Ai or ring Aii;

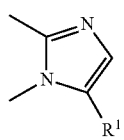

Ai

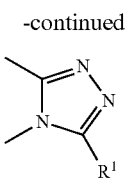

Aii when X is N and B is N, ring A is Aiii;

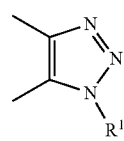

Aiii and when X is N and B is N, or X is N and B is CH, ring A is Ai;

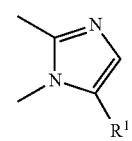

Ai $R^1$ is fluoroquinolinylmethyl-, fluoroquinolinylmethyl-d-, fluoroquinolinylmethyl-d2-, quinolinylmethyl-, difluoroquinolinylmethyl-, fluoroquinolinylhydroxymethyl-, quinolinylhydroxymethyl-, difluoroquinolinylhydroxymethyl-, fluoroquinolinylhydroxyethyl-, quinolinylhydroxyethyl-, fluoroquinolinylethyl-, quinolinylethyl-, 4,6-difluoro-1-methylindazolylethyl-, 4,6-difluoro-1-methylindazolylmethyl-, difluoro(quinolinyl)methyl-, quinolinylpropanyl-, difluoroquinolinylethyl-, quinolinylcyclopropyl-, 6-fluoro-1-methylindazolylethyl-, 6-fluoro-1-methyl-indazolylmethyl-, 1-methylindazolylmethyl-, or 1-methylindazolylethyl-;

$R^2$ is hydrogen, $NH_2$, ethyl or methyl;

$R^3$ is —$CONH_2$, ethyl, —CO($C_1$-$C_2$)alkyl, phenyl, pyridinyl, —CONHphenyl, —CONHchlorophenyl, $CONHCH_3$, benzoxazolyl, —$SO_2$Me, CSNH($C_1$-$C_2$)alkyl, CSNHbenzyl-, —$CSNH_2$, —$COCH_2$morpholine, —$COCH_2$(4-methylpiperazine), hydrogen, —$CO_2CH_3$, or —COpyridinyl, $R^4$ is hydrogen or methyl;

or $R^3$ and $R^4$ together with the nitrogen to which they are attached form oxazolidinone, oxazolidinedione, imidazolidinone or imidazolidinedione.

In a more preferred embodiment of the invention there is provided a compound of formula (I) wherein
B is N;
Y is C or N;
X is CH or N;
such that when X is CH, ring A is ring Ai or ring Aii

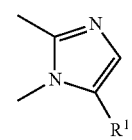

Ai

-continued

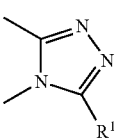

Aii and when X is N, ring A is Aiii;

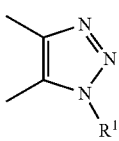

Aiii $R^1$ is i;

i $R^5$ is quinolinyl optionally substituted by one or two fluoro substituents;
$R^2$ is methyl;
$R^3$ is —$CONH_2$;
$R^4$ is hydrogen;
and either
$R^6$ and $R^7$ are both hydrogen;
$R^6$ and $R^7$ are both fluoro;
$R^6$ and $R^7$ are both deuterium; or
$R^6$ is methyl and $R^7$ is hydrogen, to form the S-enantiomer.

Various embodiments of the invention are described herein. It will be recognized that features specified in each embodiment may be combined with other specified features to provide further embodiments.

In a particular embodiment, the invention provides one or more compounds selected from the Example compounds disclosed herein, or a pharmaceutically acceptable salt thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans- configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration, such as for the asymmetric carbon atom which may be present within the $R^1$ group (i) defined herein. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Preferably for the asymmetric $R^1$ group (i) defined herein, the (S) enantiomer is in excess, in amounts as described above.

Substituents at atoms with unsaturated bonds may, if possible, be present in cis-(Z)- or trans-(E)-form. Preferably, the hydrazones of the present invention have the trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

As used herein, the term "pharmaceutically acceptable salts" refers to salts that retain the biological effectiveness and properties of the compounds of this invention and, which typically are not biologically or otherwise undesirable. The salt can be present alone or in mixture with free compound of the formula (I). In many cases, the compounds of the present invention are capable of forming acid salts by virtue of the presence of amino groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfomate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the present invention can be synthesized from a parent compound, a basic or acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). "Salts", or "salts thereof" or "or a salt thereof", can be present alone or in mixture with free compound of the formula (I).

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. Any formula given herein is intended to represent hydrates, solvates, and polymorphs of such compounds, and mixtures thereof.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the invention therefore include compounds of formula I, polymorphs, and isomers thereof (including optical, geometric and tautomeric isomers) and isotopically-labelled compounds of formula I, as defined herein. In preferred embodiments, which are preferred independently, collectively or in any combination or sub-combination, the invention relates to a compound of the formula (I), in free base form or in acid addition salt form, wherein the substituents are as defined herein.

The compounds of the present invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. [Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).]

Prodrugs can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of such prodrugs include:
(i) where the compound of formula (I) contains a carboxylic acid functionality (—COOH), an ester thereof, for example, replacement of the hydrogen with $(C_1-C_8)$alkyl;
(ii) where the compound of formula (I) contains an alcohol functionality (—OH), an ether thereof, for example, replacement of the hydrogen with $(C_1-C_6)$alkanoyloxymethyl; and
(iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Certain compounds of formula (I) may also themselves act as prodrugs of other compounds of formula (I).

The invention further relates to a pharmaceutically acceptable prodrug of a compound of formula (I). The invention further relates to a pharmaceutically acceptable metabolite of a compound of formula (I).

"C-Met tyrosine kinase mediated diseases" are especially such disorders that respond in a beneficial way (e.g. amelioration of one or more symptoms, delay of the onset of a disease, up to temporary or complete cure from a disease) to the inhibition of a protein tyrosine ki-nase, especially inhibition of a c-Met kinase. These disorders include proliferative diseases such as tumor diseases, in particular solid tumors and metastasis derived thereof, e.g. hereditary papillary renal cell carcinoma (PRCC), sporadic forms of PRCC, head and neck cancer, squamous cell carcinoma, gastric carcinoma, pancreatic carcinoma, lung cancer, bladder cancer, breast cancer, leiomyosarcoma, glioblastoma, melanoma, alveolar soft part sarcoma. These disorders further include inflammatory conditions, such as inflammatory conditions due to an infection.

"Combination" refers to either a fixed combination in one dosage unit form, or a kit of parts for the combined administration where a compound of the formula (I) and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The invention relates especially to a compound of the formula (I) as provided in the Examples, as well as the methods of manufacture described therein.

The compounds of formula (I) have valuable pharmacological properties, as described hereinbefore and hereinafter.

In another embodiment of the invention, there is provided a method for treating a c-Met related disorder or condition. The disorder or condition to be treated is preferably a proliferative disease such as a cancer or an inflammatory condition. Compounds of formula (I) are further useful for treating diseases associated with a c-Met-related condition.

A: Proliferative Diseases: Compounds of Formula (I) are Particular Useful for the Treatment of One or More of the Following Proliferative Diseases:

Compounds of formula (I) are useful in the treatment of cancer wherein the cancer is selected from the group consisting of brain cancer, stomach cancer, genital cancer, urinary cancer, prostate cancer, bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

Compounds of formula (I) are useful in the treatment of cancer wherein the cancer is stomach, colon, liver, genital, urinary, melanoma, or prostate. In a particular embodiment, the cancer is liver or esophageal.

Compounds of formula (I) are useful in the treatment of colon cancer, including metastases, e.g. in the liver, and of non-small-cell lung carcinoma.

Compounds of formula (I) may also be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrange-ments (e.g. TPR-MET; Cooper et al. Nature 311, 29-33, 1984; Park. et al. Cell 45, 895-904, 1986).

Compounds of formula (I) are further useful in the treatment of additional cancers and conditions as provided herein or known in the art.

B: Inflammatory Conditions: Compounds of Formula (I) are Particular Suitable for the Treatment of One or More Inflammatory Conditions.

In a further embodiment, the inflammatory condition is due to an infection. In one embodiment, the method of treatment would be to block pathogen infection. In a particular embodiment, the infection is a bacterial infection, e.g., a Listeria infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF.

Compounds of formula (I) are further useful in the treatment of additional inflammatory disorders and conditions as provided herein or known in the art.

C: Combination Therapy: in Certain Embodiments, any of the Above Methods Involve Further Administering a Chemotherapeutic Agent.

In a related embodiment, the chemotherapeutic agent is an anti-cancer agent. Specific combinations are provided throughout the application.

In a further related embodiment, any of the above methods involve further administering a pathway specific inhibitor. The pathway specific inhibitor may be a chemotherapeutic agent or may be a biologic agent, e.g., such as antibodies. Pathway specific inhibitors include, but are not limited to, inhibitors of EGFR, Her-2, Her-3, VEGFR, Ron, IGF-IR, PI-3K, mTOR, Raf.

In a further related embodiment to several of the above methods, following administering to the subject or contacting the cell, these methods can further involve observing amelioration or retardation of development or metastasis of the cancer.

Thus, in one embodiment, the invention relates to a method of treating a c-Met related disorder or condition which involves administering to a subject in need thereof an effective amount of a compound of formula (I).

In a further embodiment, the invention relates to a compound of formula (I) or a pharmaceutically acceptable salt thereof, for use as a medicament, in particular for the treatment of one or more C-Met tyrosine kinase mediated diseases.

In a further embodiment, the invention relates to the use of a compound of formula (I) or a pharmaceutically acceptable salt thereof, in the manufacture of a medicament for the treatment of one or more C-Met tyrosine kinase mediated diseases.

In a further embodiment, the invention relates to a method for the treatment of a disease or disorder which responds to an inhibition of C-Met tyrosine kinase, which comprises administering a compound of formula (I) or a pharmaceutically acceptable salt thereof, especially in a quantity effective against said disease, to a warm-blooded animal requiring such treatment.

In a further embodiment, the invention relates to a pharmaceutical composition comprising a compound of formula (I) as active ingredient in association with at least one pharmaceutical carrier or diluent.

In a further embodiment, the invention relates to a pharmaceutical composition comprising: (a) an effective amount of compound of formula (I) and pharmaceutically acceptable salts, pharmaceutically acceptable prodrugs, and/or pharmaceutically active metabolites thereof; and (b) one or more pharmaceutically acceptable excipients and/or diluents.

In a further embodiment, the invention relates to a pharmaceutical composition for treatment of a disease, e.g. of solid or liquid tumours in warm-blooded animals, including humans, comprising a dose effective in the treatment of said disease of a compound of the formula (I) as described above or a pharmaceutically acceptable salt of such a compound together with a pharmaceutically acceptable carrier (=carrier material).

In another embodiment of the invention, there is provided a pharmaceutical preparation (composition), comprising a compound of formula (I) as defined herein, or a pharmaceutically acceptable salt of such a compound, or a hydrate or solvate thereof, and at least one pharmaceutically acceptable carrier and/or diluents and optionally one or more further therapeutic agents.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by cMet or (ii) associated with cMet activity, or (iii) characterized by activity (normal or abnormal) of cMet; or (2) reducing or inhibiting the activity of cMet; or (3) reducing or inhibiting the expression of cMet. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of cMet; or at least partially reducing or inhibiting the expression of cMet.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention relates also to a pharmaceutical composition comprising an effective amount, especially an amount effective in the treatment of one of the above-mentioned diseases, disorders or conditions, of a compound of formula (I) or a pharmaceutically acceptable salt thereof, together with one or more pharmaceutically acceptable carriers that are suitable for topical, enteral, for example oral or rectal, or parenteral administration and that may be inorganic or organic, solid or liquid.

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula (I) or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In another embodiment of the invention, there is provided a combination of a compound of formula (I) with one or more other therapeutically active agents. Thus, a compound of formula (I) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents.

A compound of formula (I) can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula (I) may be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; kinesin spindle protein inhibitors; MEK inhibitors; leucovorin; EDG binders; antileukemia compounds; ribonucleotide reductase inhibittors; S-adenosylmethionine decarboxylase inhibitors; angiostatic steroids; corticosteroids; other chemotherapeutic compounds (as defined below); photosensitizing compounds.

Further, alternatively or in addition they may be used in combination with other tumor treatment approaches, including surgery, ionizing radiation, photodynamic therapy, implants, e.g. with corticosteroids, hormones, or they may be used as radiosensitizers.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), dauno-rubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, c-Met tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin kinase family inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

n) compounds targeting, decreasing or inhibiting the activity of the Ron receptor tyrosine kinase.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™ "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra). The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide (TEMODAL®), AUY922 from Novartis.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "antileukemic compounds" includes, for example, Ara-C, a pyrimidine analog, which is the 2"-alphahydroxy ribose (arabinoside) derivative of deoxycytidine. Also included is the purine analog of hypoxanthine, 6-mercaptopurine (6-MP) and fludarabine phosphate. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "kinesin spindle protein inhibitors" is known in the field and includes SB715992 or SB743921 from GlaxoSmithKline, pentamidine/chlorpromazine from CombinatoRx;

The term "MEK inhibitors" is known in the field and includes ARRY142886 from Array PioPharma, AZD6244 from AstraZeneca, PD181461 from Pfizer, leucovorin.

The term "ribonucleotide reductase inhibitors" includes, but is not limited to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF/VEGFR disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Corticosteroids" as used herein includes, but is not limited to compounds, such as e.g. fluocinolone, dexamethasone; in particular in the form of implants.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

A compound of formula (I) may also be used in combination with one or more further drug substances selected from the group of anti-inflammatory drug substances; antihistamine drug substances; bronchodilatatory drug substances, NSAID; antagonists of chemokine receptors. The compounds of the invention are also useful as co-therapeutic compounds for use in combination with such further drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with such other drug substance in a fixed pharmaceutical composition or it may be administered separately (i.e. before, simultaneously with or after the other drug substance). Accordingly, the invention includes a combination of a compound of formula (I) with one or more further drug substance selected from the group of anti-inflammatory drug substances; antihistamine drug substances; bronchodilatatory drug substances, NSAID antagonists of chemokine receptors; said compound of the formula (I) and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelu-kast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

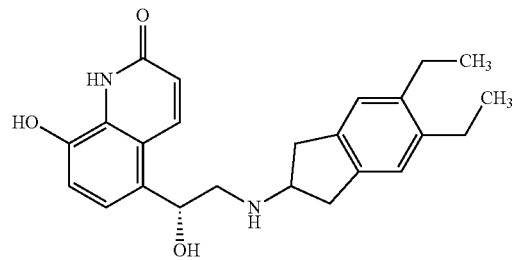 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable chemokine receptors include, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, an antibody against the ligand VEGF, or the PDGF receptor tyrosine kinase, e.g. STI571 (Glivec®), PI3K (such as BEZ235 from Novartis) and mToR inhibitors, such as rapamycin, RAD001, a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula (I), can be prepared and administered as described in the art, such as in the documents cited above.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides the use of a compound of formula (I) for treating a disease or condition mediated by cMet, wherein the medicament is prepared for administration with another therapeutic agent. The invention also provides the use of another therapeutic agent for treating a disease or condition mediated cMet, wherein the medicament is administered with a compound of formula (I).

Thus, the invention relates in a further embodiment to a combination, particularly a pharmaceutical composition) comprising a therapeutically effective amount of a compound of formula (I) in free form or in pharmaceutically acceptable salt form and a second therapeutically active agent, for simultaneous or sequential administration. The additional therapeutic agent is preferably selected from the group consisting of an anti-cancer agent; an anti-inflammatory agent.

The invention further relates to a method for the treatment of a disease or disorder which responds to a C-Met tyrosine kinase, especially a proliferative disorder or disease, in particular a cancer, said method comprises administration of an effective amount of a combination of pharmaceutical agents which comprise: (a) a compound of formula (I); and (b) one or more pharmaceutically active agents, to a subject in need thereof, especially human.

The invention further relates to the use of a combination of pharmaceutical agents which comprise: (a) a compound of formula (I); and (b) one or more pharmaceutically active agents for the treatment of a disease or disorder which responds to a C-Met tyrosine kinase, especially a proliferative disorder or disease, in particular a cancer.

The invention further relates to the use of a combination of pharmaceutical agents which comprise: (a) a compound of formula (I); and (b) one or more pharmaceutically active agents for the manufacture of a medicament for the treatment of a disease or disorder which responds to a C-Met tyrosine kinase, especially a proliferative disorder or disease, in particular a cancer.

The invention further relates to pharmaceutical compositions comprising (a) a compound of formula (I) and (b) a pharmaceutically active agent; and (c) a pharmaceutically acceptable carrier; wherein at least one pharmaceutically active agent is an anti-cancer therapeutic.

The present invention further relates to a commercial package or product comprising:

(a) a compound of formula (I); and (b) a pharmaceutical formulation of a pharmaceutically active agent for simultaneous, concurrent, separate or sequential use; wherein at least one pharmaceutically active agent is an anti-cancer therapeutic.

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The invention also provides the use of a compound of formula (I) for treating a disease or condition mediated by cMet, wherein the patient has previously (e.g. within 24 hours) been treated with another therapeutic agent. The invention also provides the use of another therapeutic agent for treating a disease or condition mediated by cMet, wherein the patient has previously (e.g. within 24 hours) been treated with a compound of formula (I).

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

The term "Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). A joint therapeutic effect can, inter alia, be determined by following the blood levels, showing that both compounds are present in the blood of the human to be treated at least during certain time intervals.

The term "Pharmaceutically effective" preferably relates to an amount that is therapeutically or in a broader sense also prophylactically effective against the progression of a disease or disorder as disclosed herein.

The term "a commercial package" or "a product", as used herein defines especially a "kit of parts" in the sense that the components (a) and (b) as defined above can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal effect) or the like.

In another embodiment of the invention, there is provided a method of manufacturing a compound of formula (I) and intermediates thereof. A compound of the formula (I) may be prepared by processes that, though not applied hitherto for the new compounds of the present invention where they thus form new processes, are known per se. The schemes provide a general overview of synthetic strategies to obtain a compound of formula (I). All methods described can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Thus, the invention relates in a further aspect to a manufacturing process (a method for manufacturing) a compound of formula (I) comprising at least one reaction step as disclosed herein, and intermediates thereof.

Scheme 1

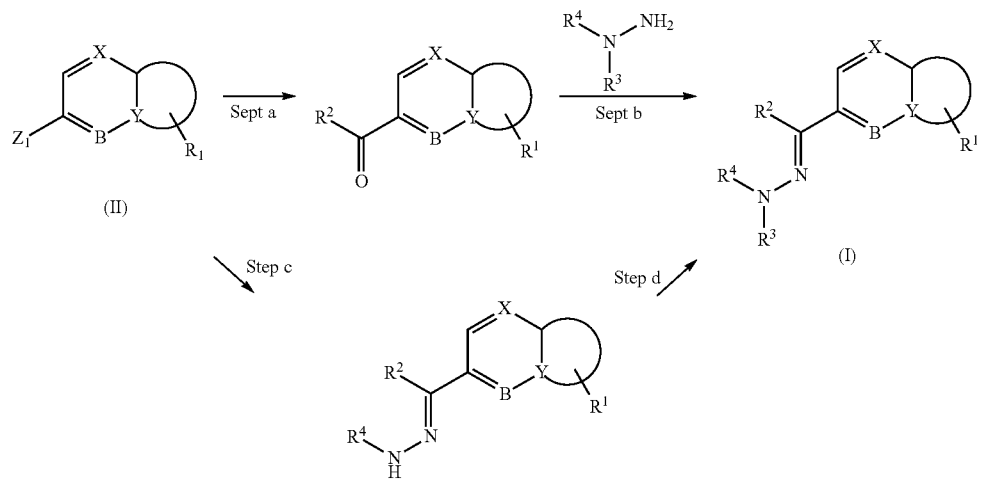

$Z_1$ is selected from Cl, Br and I

Scheme 2 provides details for a synthetic strategy to obtain preferred compounds of formula (IA, IB, IC) through (IIA, IIB and IIC)

Scheme 2

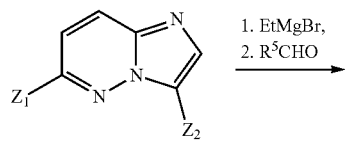

1. EtMgBr,
2. $R^5$CHO

35
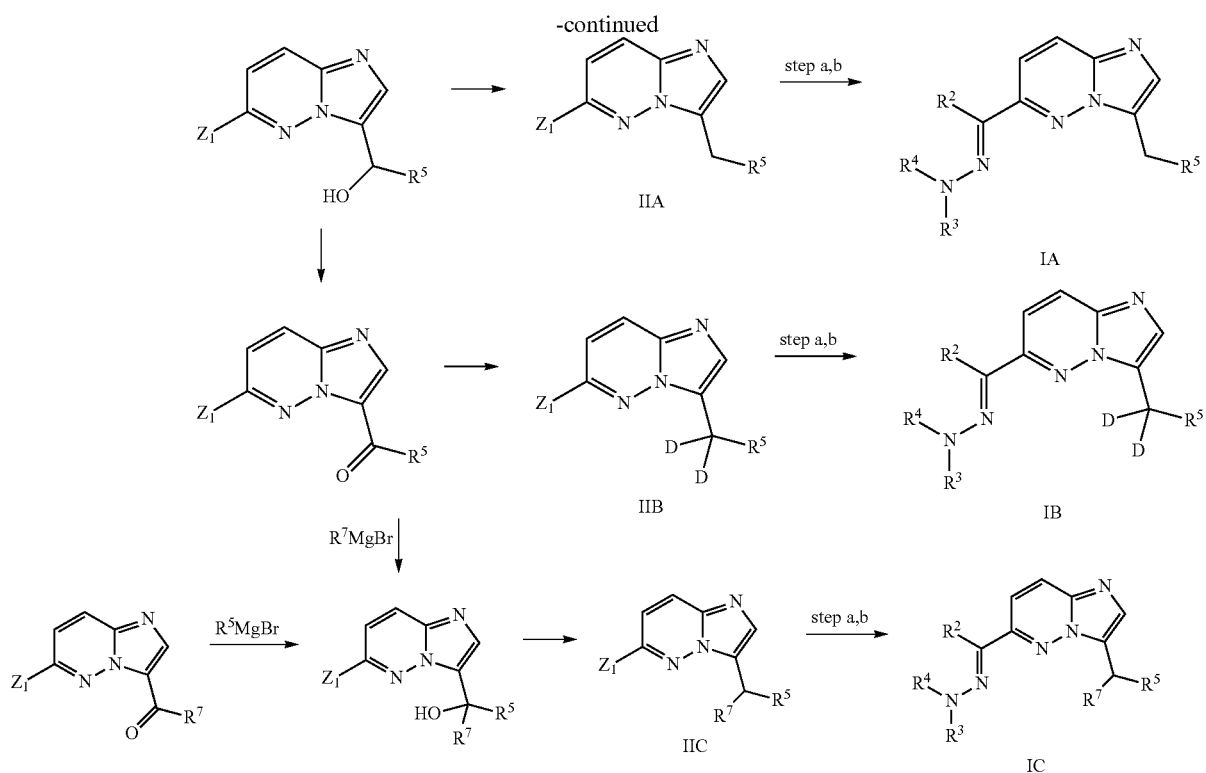
$Z_1$ and $Z_2$ are independently selected from Cl, Br and I
Scheme 3 provides details for an synthetic strategy to obtain preferred compounds of formula (ID) through (IID).
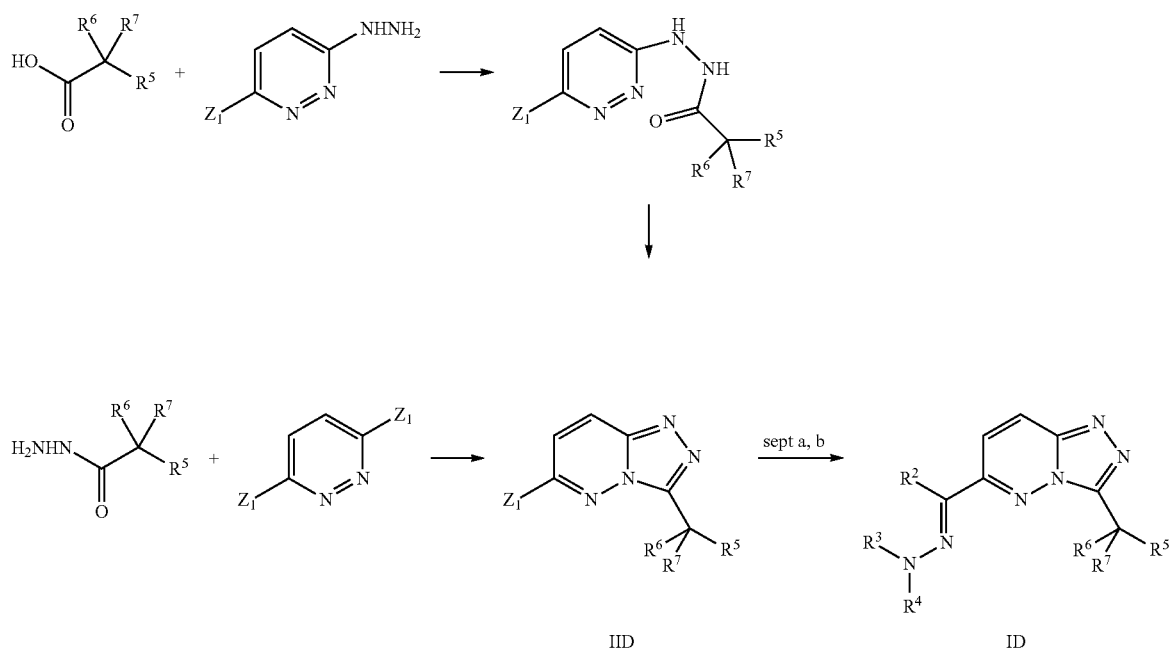
$Z_1$ is selected from Cl, Br and I
Scheme 4 provides details for an synthetic strategy to obtain preferred compounds of formula (IE) through (IIE).

Scheme 4

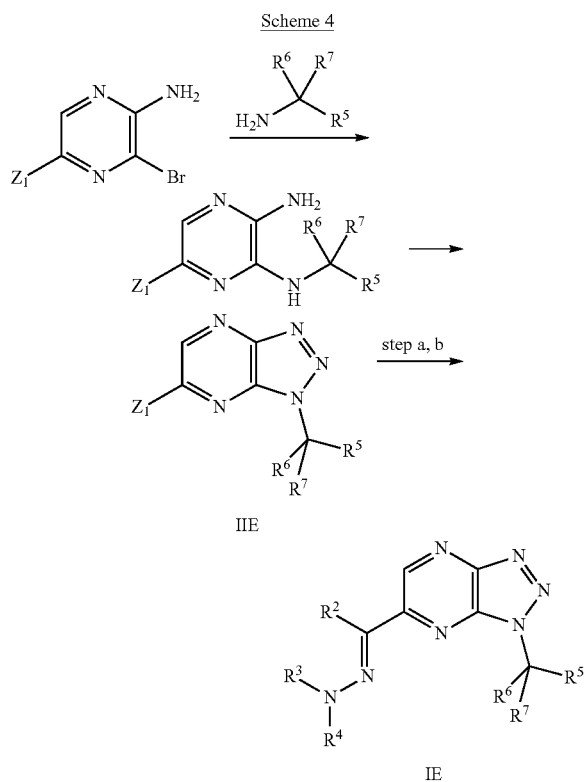

IE $Z_1$ is selected from Cl, Br and I

Scheme 5 provides details for an synthetic strategy to obtain preferred compounds of formula (IF) through (IIF).

Scheme 5

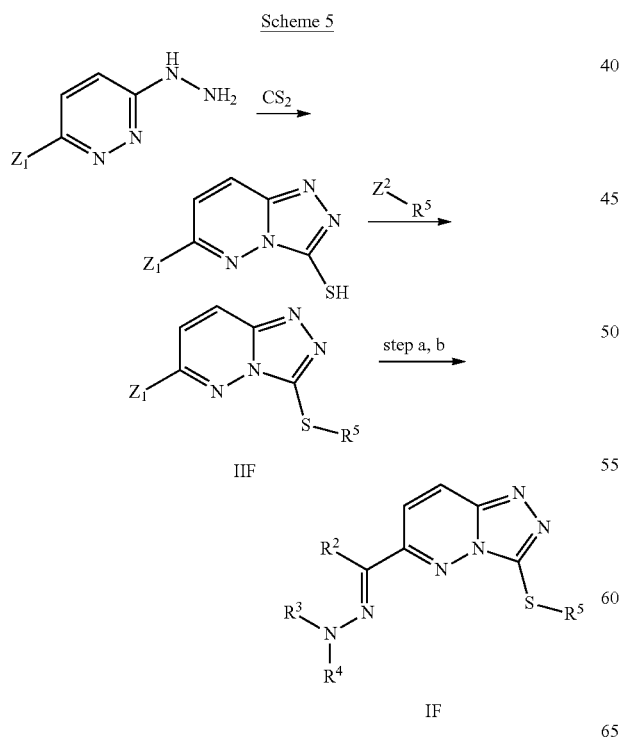

IF $Z_1$ and $Z_2$ are independently selected from Cl, Br and I

Oxidation using methods well known to the skilled person results in SO/SO$_2$ linkers Scheme 6 provides details for an synthetic strategy to obtain preferred compounds of formula (IG) through (IIG).

Scheme 6

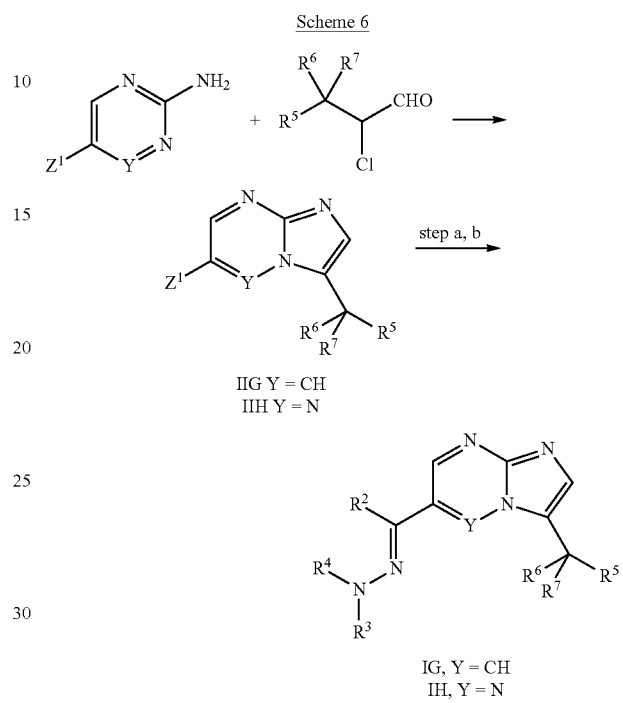

IIG Y = CH
IIH Y = N

IG, Y = CH
IH, Y = N $Z_1$ is selected from Cl, Br, or I

Scheme 7 provides alternative details for an synthetic strategy to obtain preferred compounds of formula (IH) through (IIH).

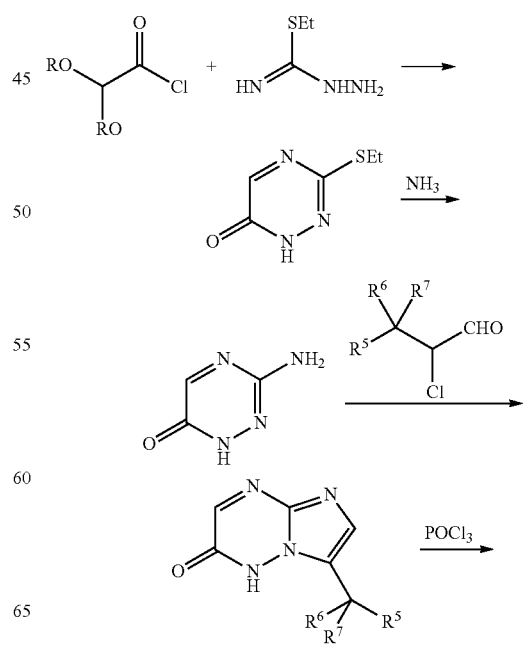

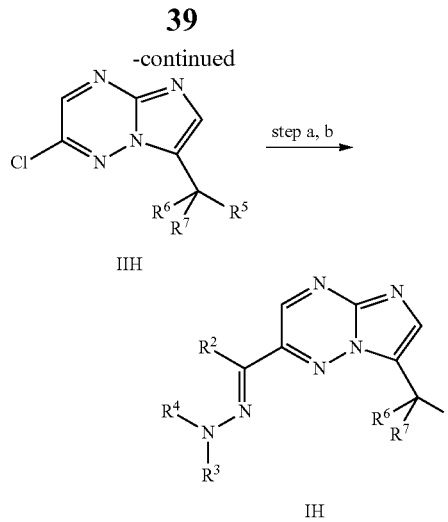

Scheme 8 provides details for an synthetic strategy to obtain preferred compounds of formula (IK) through (IIK).

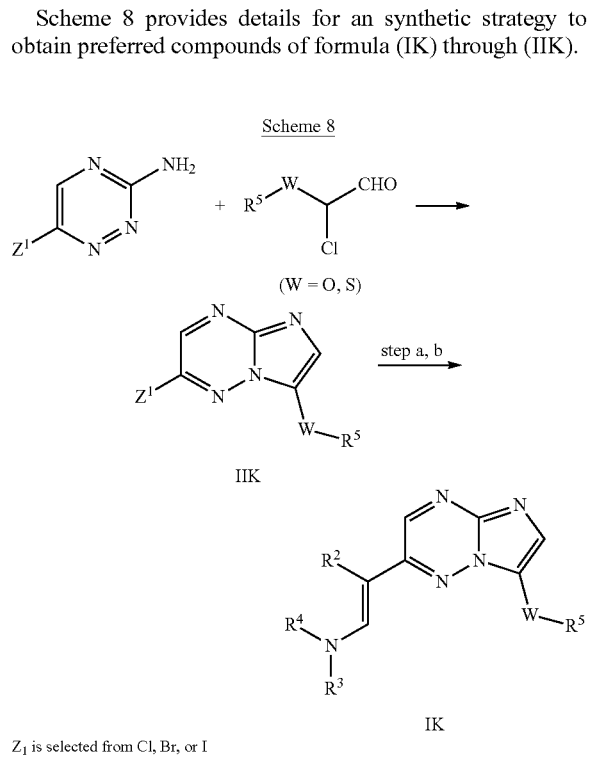

$Z_1$ is selected from Cl, Br, or I

The following examples illustrate the invention without limiting the scope thereof. In the examples provided, temperatures are measured in degrees Celsius. Unless otherwise indicated, the reactions take place at rt. Further, if not indicated otherwise, the analytical HPLC conditions are as follows:

Method A:
The flow is 0.5 mL/min of methanol and water (with 0.5% acetic acid)
0-4.0 min: 10% to 90% of methanol
4.0-6.0 min: 90% of methanol
Column: GP C18 3 μm 4.6×30 mm from Sepax.
Oven temperature: 30° C.
Method B:
The flow is 1.2 mL/min of methanol and water (with 0.5% acetic acid)
0-2.0 min: 10% to 90% of methanol
2.0-3.0 min 90% of methanol
Column: GP C18 3 μm 4.6×30 mm from Sepax.
Oven temperature: 30° C.
Method C:
The flow is 0.5 mL/min of methanol and water (with 0.5% acetic acid)
0-3.0 min: 60% to 90% of methanol
3.0-5.0 min: 90% of methanol
Column: GP C18 3 μm 4.6×30 mm from Sepax.
Oven temperature: 30° C.
Method D:
The flow is 0.5 mL/min of methanol and water (with 0.5% acetic acid)
0-3.0 min: 10% to 50% of methanol
3.0-4.0 min: 50% of methanol
Column: GP C18 3 μm 4.6×30 mm from Sepax.
Oven temperature: 30° C.
Method E:
The flow is 0.5 mL/min of methanol and water (with 0.5% acetic acid)
0-4.0 min: 10% to 90% of methanol
4.0-8.0 min: 90% of methanol
Column: GP C18 3 μm 4.6×30 mm from Sepax.
Oven temperature: 30° C.
Method F:
The flow is 1 mL/min of Hexane/Ethanol/Diethyleamine 60/40/0.1, v/v/v
Column: CHIRALPAK AD-H, 4.6×150 mm
Oven temperature: 35° C.
Method G:
The flow is 1 mL/min of Hexane/Isopropanol/Diethylamine 70/30/0.1, v/v/v
Column: CHIRALPAK AD-H, 4.6×150 mm
Oven temperature: 35° C.

In the following examples, the abbreviations given below are used:

| | |
|---|---|
| AcOH | acetic acid |
| atm. | atmosphere |
| BINAP | 2,2'-Bis-diphenylphosphanyl-[1,1']binaphthalenyl |
| Bn | benzyl |
| Boc | tert-butoxycarbonyl |
| DCM | dichloromethane |
| DME | 1,2-dimethoxyethane |
| $Et_2O$ | diethyl ether |
| EtOAc or EA | ethyl acetate |
| EtOH | ethanol |
| DCC | dicyclohexylcarbodiimide |
| DME | dimethyl ethylene glycol |
| DMF | N,N-dimethylformamide |
| DMSO | dimethyl sulfoxide |
| eq. | equivalent(s) |
| h | hour(s) |
| HATU | 2-(1H-7-Azabenzotriazol-1-yl)-1,1,3,3-tetramethyluronium hexafluorophosphate |
| HPLC | High Performance Liquid Chromatography |
| HV | high vacuum |
| IBX | 2-iodoxybenzoic acid |
| Isolute | Isolute ® HM-N by International Solvent Technology Ltd., U.K. |
| LAH | lithium aluminium hydride |
| LCMS | liquid chromatography coupled with mass spectrometry |
| LDA | lithium diisopropylamide |
| mL | milliliter(s) |
| min | minute(s) |
| MPLC | Medium Pressure Liquid Chromatography |
| MS-ES | electrospray mass spectrometry |
| MW | microwave |
| NBS | N-Bromosuccinimide |
| n-BuLi | n-Butyllithium |

| | |
|---|---|
| NMP | N-Methylpyrrolidinone |
| PdCl$_2$(dppf) | 1,1-Bis(diphenylphosphino)ferrocenedichloropalladium (II) |
| Pd$_2$(dba)$_3$ | Tris(dibenzylideneacetone)dipalladium (0) |
| PdCl$_2$(Ph$_3$)$_2$ | Dichlorobis(triphenylphosphine)palladium (II) |
| PL | PolymerLabs (cartridge supplier) |
| RM | reaction mixture |
| R$_f$ | ratio of fronts in TLC |
| SPE | Solid Phase Extraction |
| rt | room temperature |
| TBAF | tetrabutylammonium fluoride |
| TBME | methyl tert-butyl ether |
| TFA | trifluoroacetic acid |
| THF | tetrahydrofuran |
| TLC | thin layer chromatography |
| t$_R$ | retention time |
| UV | Ultraviolet |

SYNTHESIS OF INTERMEDIATES

Intermediate A

3-Bromo-6-chloroimidazo[1,2-b]pyridazine

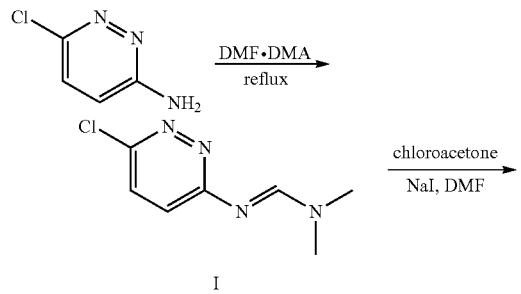

intermediate A

To a solution of 6-chloroimidazo[1,2-b]pyridazine (5 g, 32.6 mmol) in acetonitrile (300 ml) was added 1-bromopyrrolidine-2,5-dione (6.37 g, 35.8 mmol) and trifluoroacetic acid (0.75 mL). The resulting solution was allowed to stir at room temperature overnight. The solvent was removed under reduced pressure and the residue was dissolved in EtOAc, washed with NaHCO$_3$ solution, water and brine, dried over Na$_2$SO$_4$ and concentrated in vacuo to afford 7.2 g title compound in 92% yield as a light yellow solid. $^1$H-NMR (400 MHz, CDCl$_3$) δ ppm 7.91 (d, 1H), 7.79 (s, 1H), 7.12 (d, 1H). LCMS (method A): [MH]$^+$=232/234, t$_R$=4.48 min.

Intermediate B 1-(6-Chloro-imidazo[1,2-b]pyridazin-3-yl)-ethanone

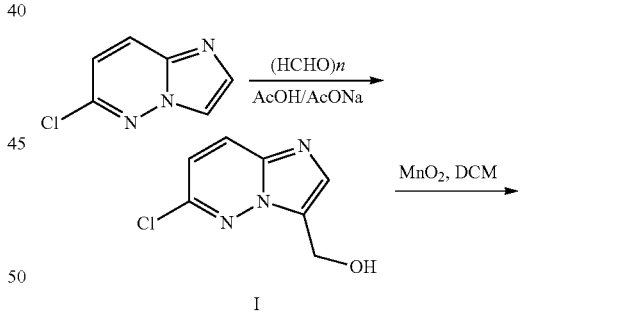

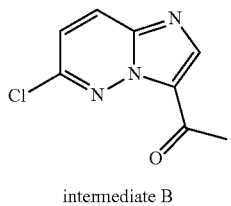

intermediate B

N'-(6-Chloro-pyridazin-3-yl)-N,N-dimethyl-formamidine (i)

A mixture of 3-amino-6-chloropyridazine (1.3 g, 10 mmol) and dimethylformamide dimethylacetal (1.35 ml, 10.2 mmol) was heated at reflux for 2 h and concentrated under vacuum to afford a brown solid. After recrystallization with EtOAc, 1.5 g of N'-(6-Chloro-pyridazin-3-yl)-N,N-dimethyl-formamidine was obtained in 81% yield.

1-(6-Chloro-imidazo[1,2-b]pyridazin-3-yl)-ethanone (Intermediate B)

To a solution of N'-(6-chloro-pyridazin-3-yl)-N,N-dimethyl-formamidine (1.3 g, 7 mmol) in DMF (60 mL) was added NaI (1 g, 6.7 mmol) and chloroacetone (1 mL, 12.6 mmol). The mixture was heated at 80° C. overnight and then concentrated under reduced pressure. The residue was purified by column chromatography to afford 1-(6-chloro-imidazo[1,2-b]pyridazin-3-yl)-ethanone (0.7 g) in 51% yield. $^1$H-NMR (400 MHz, CDCl$_3$) δ ppm 8.42 (s, 1H), 8.05 (d, 1H), 7.31 (d, 1H), 2.77 (s, 3H).

Intermediate C

6-Chloro-imidazo[1,2-b]pyridazine-3-carbaldehyde

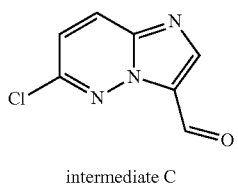

intermediate C (6-Chloro-imidazo[1,2-b]pyridazin-3-yl)-methanol (i)

To a solution of 6-chloroimidazo[1,2-b]pyridazine (1.5 g, 9.8 mmol) in AcOH (50 mL) was added NaOAc (1.4 g, 17.1 mmol) and paraformaldehyde (1.5 g). The mixture was heated at reflux overnight and then concentrated under reduced pressure. The residue was basified to pH=12. Then the mixture was filtered and the solid was washed with EtOH to afford (6-chloro-imidazo[1,2-b]pyridazin-3-yl)methanol (1.3 g) in 72% yield.

6-Chloro-imidazo[1,2-b]pyridazine-3-carbaldehyde (Intermediate C)

To a solution of (6-chloro-imidazo[1,2-b]pyridazin-3-yl)-methanol (1.3 g, 7.1 mmol) in DCM (50 mL) was added active $MnO_2$ (3 g, 34.5 mmol). The mixture was stirred at rt overnight and then filtered. The filtrate was concentrated under vacuum and the residue was washed with EtOAc to afford 6-chloro-imidazo[1,2-b]pyridazine-3-carbaldehyde (0.7 g) in 54% yield. $^1$H-NMR (400 MHz, $CDCl_3$) δ 10.36 (s, 1H), 8.42 (s, 1H), 8.08 (d, 1H), 7.38 (d, 1H).

Intermediate D

Quinolin-6-ylmethanamine

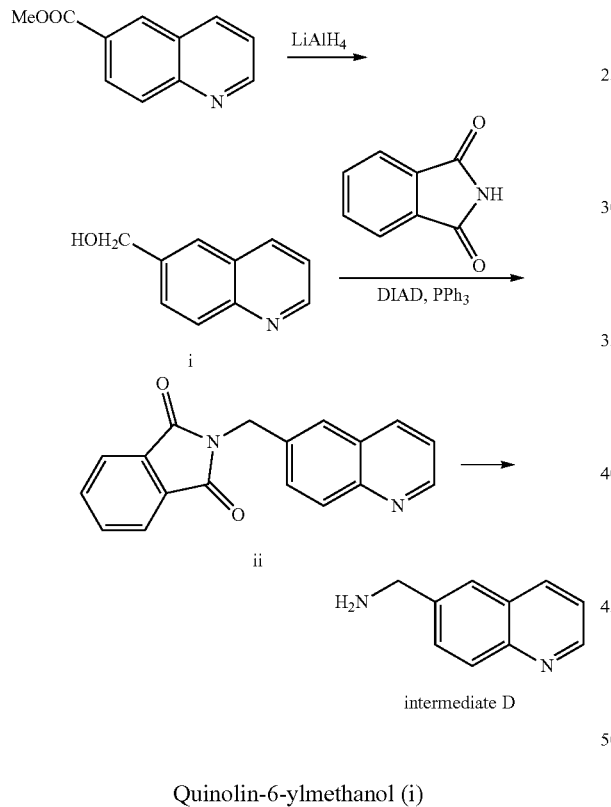

intermediate D

Quinolin-6-ylmethanol (i)

To a solution of methyl quinoline-6-carboxylate (14 g, 74.8 mmol) in THF (80 mL), was added $LiAlH_4$ (2.84 g, 74.8 mmol) in portions. Then water (2.84 mL) and NaOH (10%, 4.26 mL) was added dropwise to quench excess reducing agent. After stirring for additional 20 min, ether was added, and the resulting mixture was filtered through celite. The filtrate was concentrated to a residue, which was purified by silica gel with hexanes:EtOAc to afford quinolin-6-ylmethanol (7.6 g) in 64% yield.

2-(Quinolin-6-ylmethyl)isoindoline-1,3-dione (ii)

To a solution of isoindoline-1,3-dione (6.47 g, 44.0 mmol) and triphenylphosphine (11.53 g, 44.0 mmol) in THF (70 mL) at a 0° C., was added a solution of quinolin-6-ylmethanol (7 g, 44.0 mmol) in THF (30 mL) and (E)-diisopropyl diazene-1,2-dicarboxylate (8.89 g, 44.0 mmol) dropwise over a period of 30 min. The mixture was then heated to 30° C. for 20 h. The reaction was cooled to rt and concentrated in vacuo. The resulting residue was purified by Analogix silica gel with gradient hexanes:EtOAc to provide 2-(quinolin-6-ylmethyl)isoindoline-1,3-dione (12.04 g) in 95% yield. LCMS (method A): $[MH]^+$=2.99, $t_R$=4.89 min.

Quinolin-6-ylmethanamine (Intermediate D)

To a solution of 2-(quinolin-6-ylmethyl)isoindoline-1,3-dione (20 g, 69.4 mmol) in MeOH (100 mL), was added hydrazine hydrate (3.47 g, 69.4 mmol). The solution was heated to reflux for 3 h, then cooled to rt, filtered through celite. The filtrate was concentrated in vacuo and EtOAc was added to dilute the residue, filtered and concentrated in vacuo to afford 6-bromo-N2-(quinolin-6-ylmethyl)pyrazine-2,3-diamine (5 g) in 41% yield 41%. LCMS (method B): $[MH]^+$= 159, $t_R$=0.93 min.

Intermediate E and F

7-Fluoro-quinoline-6-carbaldehyde and 7-(7-Fluoro-quinolin-6-yl)-methylamine

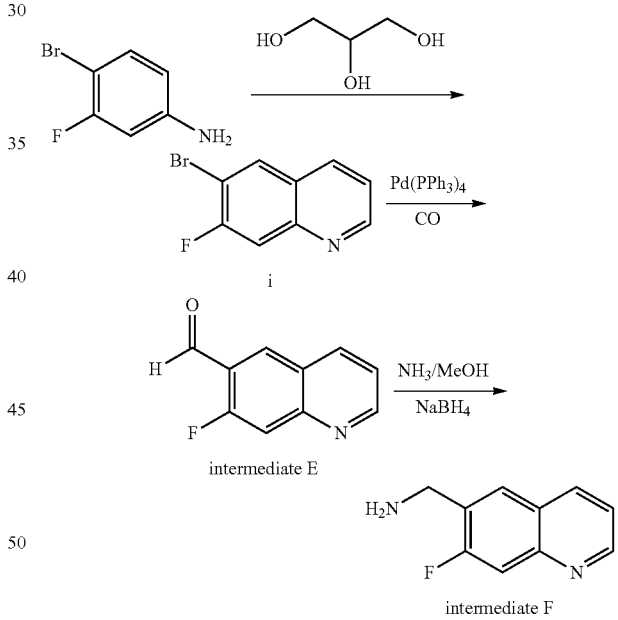

intermediate E intermediate F 6-bromo-7-fluoro quinoline (i)

To a suspension of 4-bromo-3-fluoro-phenylamine (100 g, 526 mmol) in concentrated sulfuric acid (290 mL) was added glycerol (220 g, 2.39 mol, 4.5 eq.) followed by ferrous sulfate (30 g, 0.2 eq.). The reaction mixture was heated at 130° C. for 14 h, cooled to rt and poured into ice-water. The solution was neutralized with saturated aqueous ammonium hydroxide to pH 8 and extracted with DCM (2 L×3). The combined organic layers were washed with brine (1 L×3), dried over sodium sulfate and concentrated under reduced pressure to afford the crude product as a brown solid, which was purified by column chromatography (Petroleum:Ethyl acetate=10:1) to give 6-bromo-7-fluoro quinoline as a white solid (45 g, 39%). $^1$H-NMR (400 MHz, DMSO-d$_6$) δ ppm 8.86 (s, 1H), 8.56 (m, 1H), 8.45 (m, 1H), 7.90 (d, 1H), 7.71 (m, 1H).

7-Fluoro-quinoline-6-carbaldehyde (Intermediate E)

To a suspension of Pd(PPh$_3$)$_4$ (1.27 g, 1.1 mmol) and sodium formate (13.8 g, 132 mmol, 6 e.q.) in acetonitrile (30 mL) was added a solution of 6-bromo-7-fluoro quinoline (5 g, 22 mmol) in DMSO (30 mL). The reaction mixture was heated at 120° C. under a CO atmosphere (1 MPa) for 4 h, cooled to rt and concentrated under reduced pressure. The residue was partitioned between water (100 mL) and ethyl acetate (150 mL). The organic layer was separated, washed with brine (100 mL), dried over Na$_2$SO$_4$ and concentrated under reduced pressure. The reside was purified by column choromatography, eluting with petroleum:ethyl acetate=10:1~3:1 to give the title compound as a white solid (400 mg, 10.4%). $^1$H-NMR (400 MHz, DMSO-d$_6$) δ ppm 8.95 (s, 1H), 8.46 (m, 1H), 8.20 (m, 1H), 7.75 (d, 1H), 7.53 (m, 1H).

7-(7-Fluoro-quinolin-6-yl)-methylamine (Intermediate F)

7-Fluoro-quinoline-6-carbaldehyde (500 mg, 2.85 mmol) was dissolved in ammonia solution (2 M in MeOH, 50 mL). After stirring at room temperature for 3 hour, NaBH$_4$ (108.0 mg, 2.85 mmol) was added in portions. The reaction mixture was stirred overnight, quenched with water in an ice-bath. Methanol was removed under reduced pressure, the residue was then diluted with water, the pH value of the solution was adjusted to around 8 with 1N HCl solution, then extracted with DCM three times. The combined organic layers were washed with water and dried over Na$_2$SO$_4$, filtered and concentrated in vacuo. The crude product purified by chromatography (DCM:MeOH=50:1) to give the title compound as a yellow solid (250.0 mg, 49%). $^1$H-NMR (400 MHz, DMSO-d$_6$) δ ppm 8.86 (dd, 1H), 8.36 (d, 1H), 8.07 (d, 1H), 7.68 (d, 1H), 7.49 (dd, 1H), 3.93 (s, 2H), 1.98 (s, 2H).

Intermediate G 1-(7-fluoroquinolin-6-yl)ethanamine

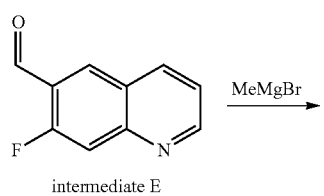

intermediate E

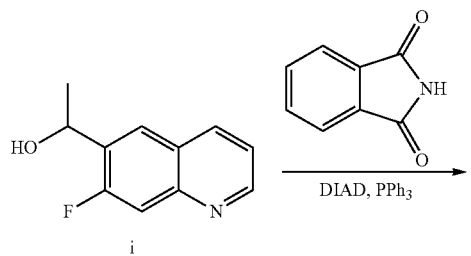

i

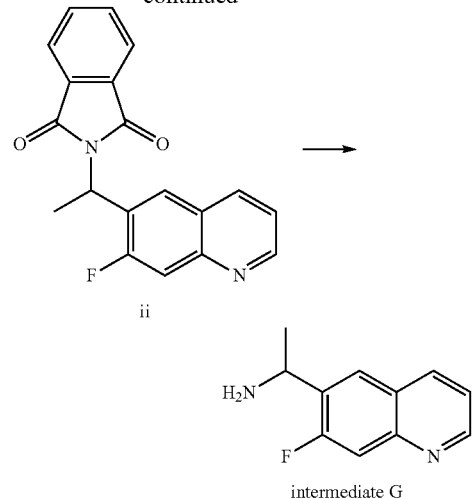

ii intermediate G 1-(7-fluoroquinolin-6-yl)ethanol (i)

To a solution of 7-fluoroquinoline-6-carbaldehyde (4.0 g, 22.84 mmol) in THF (30 ml) at 0° C., was added methylmagnesium bromide (2.85M in THF, 8 mL, 22.84 mmol) dropwise. The solution was stirred for 2 h, and NH$_4$Cl was added to quench the reaction. The resulting mixture was extracted with EtOAc and the organic layer was washed with saturated NaHCO$_3$ and NH$_4$Cl, and dried over Na$_2$SO$_4$, filtered and concentrated to give the crude product, which was purified with Analogix gel silica using hexanes:EtOAc to afford 1-(7-fluoroquinolin-6-yl)ethanol (i). LCMS (method B): [MH]$^+$= 192, t$_R$=1.84 min.

2-(1-(7-fluoroquinolin-6-yl)ethyl)isoindoline-1,3-dione (ii)

The title compound was prepared as a white solid in analogy to the synthesis of intermediate D from 1-(7-fluoroquinolin-6-yl)ethanol. LCMS (method B): [MNa]$^+$=353, t$_R$=1.95 min.

1-(7-fluoroquinolin-6-yl)ethanamine (intermediate G)

The title compound was prepared in analogy to the synthesis of intermediate D from 2-(1-(7-fluoroquinolin-6-yl)ethyl)isoindoline-1,3-dione.

Intermediate H 5,7-difluoro-quinoline-6-carbaldehyde

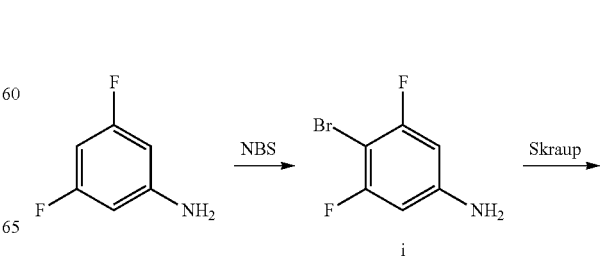

i

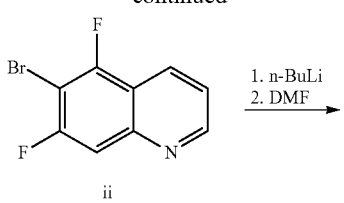

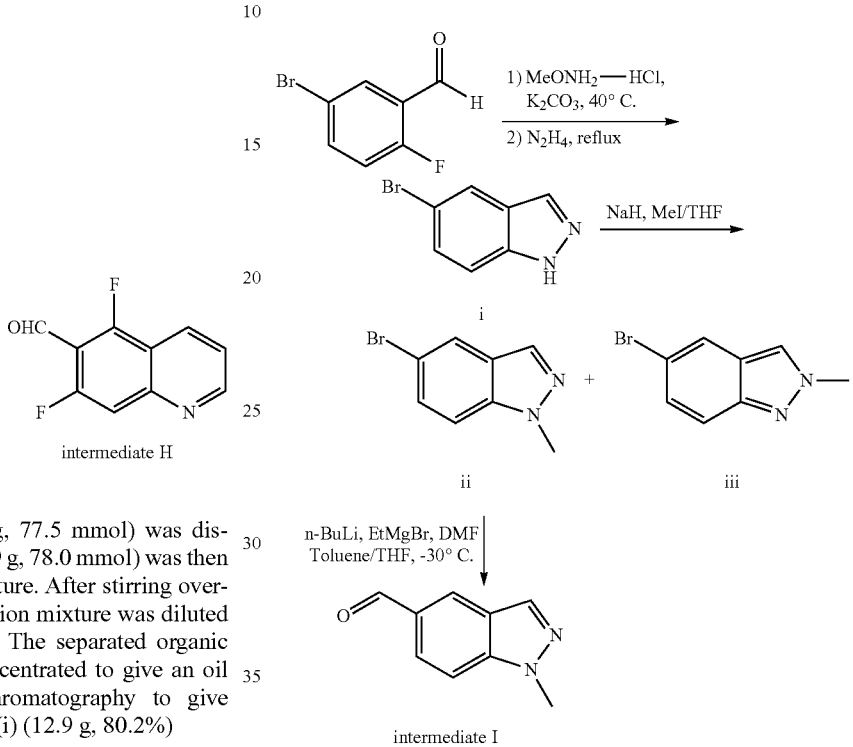

5,7-difluoro-phenylamine (10.0 g, 77.5 mmol) was dissolved in DMF (100 mL). NBS (13.9 g, 78.0 mmol) was then added portionwise at room temperature. After stirring overnight at room temperature, the reaction mixture was diluted with Et$_2$O and washed with brine. The separated organic phase was dried (Na$_2$SO$_4$) and concentrated to give an oil which is purified by column chromatography to give 4-bromo-3,5-difluoro-phenylamine (i) (12.9 g, 80.2%)

A mixture of 4-bromo-3,5-difluoro-phenylamine (i) (6.0 g, 28.8 mmole), 1.82 g ferrous sulfate, 8.6 mL glycerol, 1.79 mL nitrobenzene, and 5.0 mL concentrated sulfuric acid was heated gently. After the first vigorous reaction, the mixture was boiled for five hours. Nitrobenzene was removed by distillation in vacuo. The aqueous solution was acidified with glacial acetic acid, and dark brown precipitate separated, which was purified by flash chromatography (silica gel, petroleum/ethyl acetate=12/1) to give 6-bromo-5,7-difluoro-quinoline (ii) as a white solid (3.5 g, 49.8%).

To a solution of 6-bromo-5,7-difluoroquinoline (ii) (250 g, 1.02 mol) in anhydrous THF (2200 mL) at −78° C., was added a solution of n-BuLi in hexane (2.5 M, 408 ml, 1.02 mol) dropwise. The resulting mixture was stirred for additional 30 min at −78° C. Then, a solution of DMF (79 mL, 1.02 mol) in anhydrous THF (200 mL) was added while the temperature was kept lower than −70° C., and the mixture was stirred at the same temperature for 30 mins. The reaction mixture was warmed slowly to room temperature and diluted with aqueous saturated solution of NH$_4$Cl (1000 mL) and water (800 mL). The mixture was extracted with ethyl acetate twice, the combined organic layers were washed with water and brine, dried over anhydrous sodium sulfate and concentrated to give brown oil, which was purified by column chromatography on silica gel eluted with petroleum and ethyl acetate (10:1) to give 5,7-difluoro-quinoline-6-carbaldehyde (intermediate H)

as a yellow solid (100 g, 50%). $^1$H NMR (DMSO, 300 MH) δ (ppm): 10.38 (s, 1H), 9.10~9.12 (m, 1H), 8.62~8.66 (m, 1H), 7.68~7.78 (m, 2H)

Intermediate I

1-Methyl-1H-indazole-5-carbaldehyde

5-Bromo-1H-indazole (i)

A suspension of 5-bromo-2-fluorobenzaldehyde (10.15 g, 50 mmol), MeONH$_2$—HCl (4.07 g, 50 mmol) and K$_2$CO$_3$ (7.59 g, 55.0 mmol) in 100 mL DME was stirred at 40° C. for 5 hours. The mixture was filtered. The filtrate containing the oxime intermediate was concentrated in vacuo to give approximately 50 mL residue. To this concentrated oxime residue was added N$_2$H$_4$—H$_2$O (50 mL, 1.03 mol) and the mixture was refluxed overnight. After the reaction was finished, the reaction mixture was concentrated in vacuo. The residue was diluted with water and extracted with EtOAc twice. The organic layers were combined, dried over Na$_2$SO$_4$ and concentrated to a residue, which was purified by flash chromatography (hexane:EtOAc=10:1) to afford the title compound as a white solid (6.02 g, 61.2%). $^1$H-NMR (400 MHz, DMSO-d$_6$) δ ppm 13.24 (bs, 1H), 9.85 (s, 1H), 8.05 (s, 1H), 7.99 (s, 1H), 7.52 (d, 1H), 7.44 (dd, 1H). LCMS (method A): [MH]$^+$=197/199, t$_R$=4.94 min.

5-Bromo-1-methyl-1H-indazole (ii) and 5-Bromo-2-methyl-2H-indazole (iii)

To a solution of 5-bromo-1H-indazole (0.19 g, 0.94 mmol) in 3 mL THF at 0° C. was added NaH (0.04 g, 1.03 mmol). The reaction solution was stirred at this temperature for 1 hour before methyl iodide (0.09 mL, 1.41 mmol) was added at 0° C. The reaction was allowed to warm to room temperature slowly and stirred for 2 hours, quenched with water and concentrated in vacuo. The residue was diluted with water and extracted with DCM twice. The organic layers were combined, dried over $Na_2SO_4$ and concentrated. The crude product was purified by flash chromatography (hexane:EtOAc=10:1) to give the title compound II (88.7 mg, 42.5%) and iii (60.9 mg, 29%) as two white solids. ii: $^1$H-NMR (400 MHz, DMSO-$d_6$) δ ppm 8.02 (d, 1H), 7.99 (d, 1H), 7.64 (d, 1H), 7.50 (dd, 1H), 4.04 (s, 3H). LCMS (method A): $[MH]^+$=211/213, $t_R$=5.19 min. iii: $^1$H-NMR (400 MHz, DMSO-$d_6$) δ ppm 8.33 (s, 1H), 7.95 (d, 1H), 7.57 (d, 1H), 7.30 (dd, 1H), 4.16 (s, 3H). LCMS (method A): $[MH]^+$=211/213, $t_R$=4.95 min.

1-Methyl-1H-indazole-5-carbaldehyde (Intermediate I)

A suspension of n-BuLi (7.33 mL, 11.73 mmol) and ethylmagnesium bromide (5.76 mL, 5.76 mmol) in 30 mL toluene was stirred at −30° C. for 30 min, then 5-bromo-1-methyl-1H-indazole (2.25 g, 10.66 mmol) in 5 mL THF was added. After stirring at −10° C. for 1 hour, anhydrous DMF (4.95 mL, 64.0 mmol) was added at −10° C. The reaction was allowed to warm to room temperature and stirred for 2 hours. The reaction was quenched with 1N HCl and concentrated in vacuo. The residue was diluted with water, extracted with DCM twice. The organic layers were combined, dried over $Na_2SO_4$ and concentrated. The crude product was purified by flash chromatography (hexane:EtOAc=10:1) to give the title compound as a white solid (1.37 g, 76%). $^1$H-NMR (400 MHz, DMSO-$d_6$) δ ppm 10.02 (s, 1H), 8.41 (d, 1H), 8.31 (d, 1H), 7.86 (dd, 1H), 7.78 (d, 1H), 4.09 (s, 3H). LCMS (method A): $[MH]^+$=161, $t_R$=4.00 min.

Intermediate J

5-Bromo-6-fluoro-1-methyl-1H-indazole

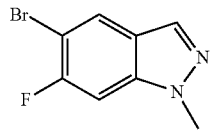

To a solution of 5-bromo-6-fluoro-1H-indazole (4 g, 18.60 mmol) in DMF (20 ml) was added potassium 2-methylpropan-2-olate (2.087 g, 18.60 mmol). The resulting mixture was stirred for 40 min. CH$_3$I (3.17 g, 22.32 mmol) was added dropwise. After stirring overnight, the reaction mixture was quenched with NH$_4$Cl(aq), extracted with EtOAc, washed with NH$_4$Cl(aq), dried over $Na_2SO_4$, filtered and concentrated in vacuo to give crude product. The crude product was purified with silica gel column chromatography with gradient Hexanes:EA to give light yellow solid 5-bromo-6-fluoro-1-methyl-1H-indazole (1.86 g, 42%).

Intermediate K

4,6-Difluoro-1-methyl-1H-indazole

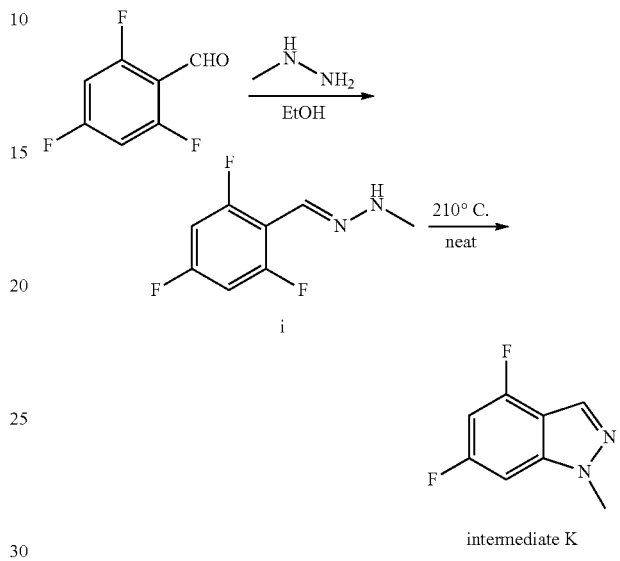

N-Methyl-N'-[1-(2,4,6-trifluoro-phenyl)-meth-(E)-ylidene]-hydrazine (i)

A solution of 2,4,6-Trifluoro-benzaldehyde (3 g, 18.74 mmol) and methyl hydrazine (40% in water, 2.6 ml, 18.74 mmol) in 20 ml anhydrous ethanol was stirred at room temperature for 1 hour. Solvent was evaporated to give the title compound as a white solid which was used in the next step without purification (3.95 g, 100%). LCMS (method B): $[MH]^+$=189, $t_R$=2.16 min.

4,6-Difluoro-1-methyl-1H-indazole (Intermediate K)

N-Methyl-N'-[1-(2,4,6-trifluoro-phenyl)-meth-(E)-ylidene]-hydrazine (3.85 g, 20.46 mmol) was heated in a seal tube at 210° C. for 2 hours. After cooled to room temperature, the black residue was dissolved in DCM and purified on flash chromatography (EtOAc:Hexane 10:90) to give the title compound as a light yellow crystal (1.926 g, 56%). $^1$H-NMR (400 MHz, MeOH-$d_4$) δ ppm 8.05 (s, 1H); 7.16 (d, 1H); 6.75 (t, 1H); 3.32 (s, 3H). LCMS (method B): $[MH]^+$=169, $t_R$=2.28 min.

Intermediate L

6-((6-Chloro-[1,2,4]-triazolo[4,3-b]pyridazin-3-yl)methyl)quinoline

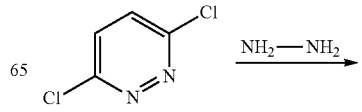

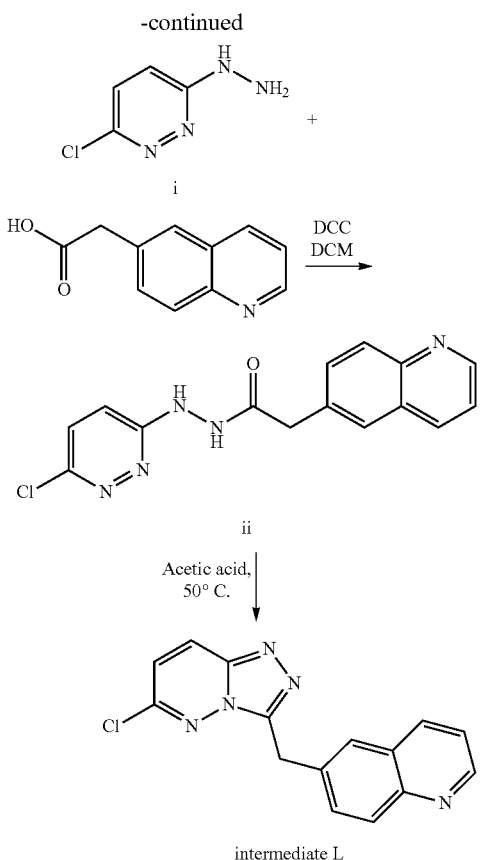

intermediate L the crude was used in the next step without purification (3.56 g, 100%). LCMS (method B): [MH]$^+$=145.1, $t_R$=0.57 min.

N'-(6-Chloropyridazin-3-yl)-2-(quinolin-6-yl)acetohydrazide (ii)

To a suspension of 3-chloro-6-hydrazinylpyridazine (3 g, 20.75 mmol) and 2-(quinolin-6-yl)acetic acid (4.27 g, 22.83 mmol) in 200 ml DCM was added DCC (5.14 g, 24.90 mmol). The solution was stirred at room temperature for overweekend. The title compound as a white solid containing dicyclohexyl urea was filtered and used in the next step without further purification (8 g, 100%). LCMS (method A): [MH]$^+$=314.1, $t_R$=2.85 min.

6-((6-Chloro-[1,2,4]triazolo[4,3-b]pyridazin-3-yl)methyl)quinoline (Intermediate L)

A solution of N'-(6-chloropyridazin-3-yl)-2-(quinolin-6-yl)acetohydrazide (8 g crude, 25.5 mmol) in 250 mL acetic acid was heated at 50° C. for 5 hours. After the reaction was completed, the solvent was evaporated and the crude was dissolved in EtOAc and filtered. The solid was mainly the impurity dicyclohexyl urea and the product dissolved in EtOAc. Solvent was evaporated and resulted the title compound as a yellow solid (4 g, 53%). $^1$H-NMR (400 MHz, MeOH-d$_4$) δ ppm 8.82 (d, 1H), 8.33 (d, 1H), 8.25 (d, 1H), 8.0 (d, 1H), 7.93 (s, 1H), 7.83 (d, 1H), 7.53 (m, 1H), 7.42 (d, 1H), 4.79 (s, 2H). LCMS (method A): [MH]$^+$=296.0, $t_R$=1.88 min.

Intermediate M

6-[(6-chloro-[1,2,4]triazolo[4,3-b]pyridazin-3-yl)-difluoro-methyl]-quinoline

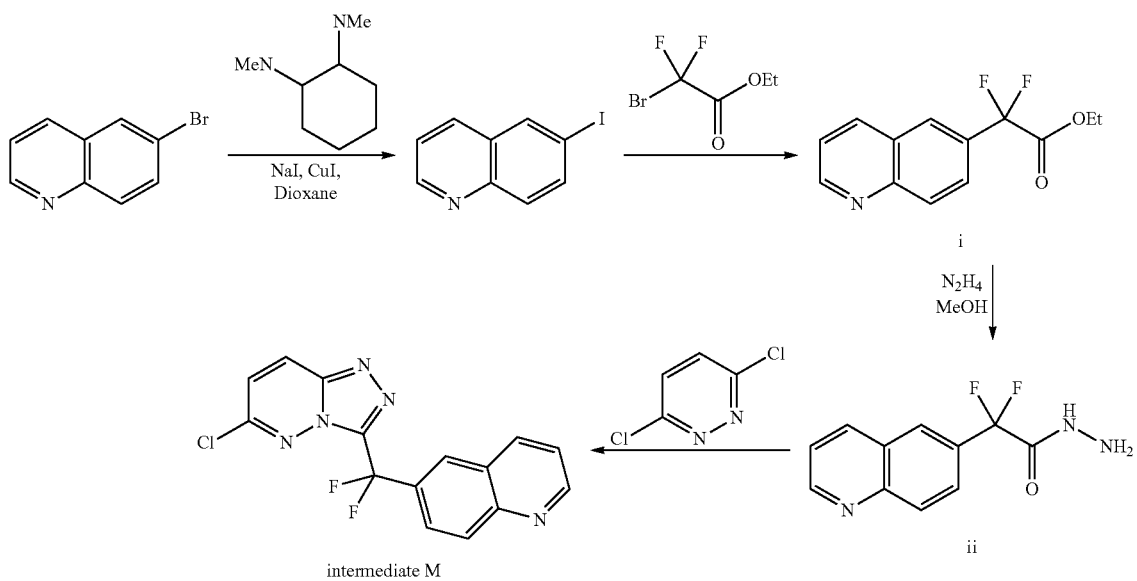

intermediate M

3-Chloro-6-hydrazinylpyridazine (i)

A mixture of 3,6-dichloropyridazine (3 g, 20.14 mmol) and hydrazine monohydride (1 g, 20.14 mmol) was heated in a sealed tube to 80° C. for 5 hours. Solvent was evaporated and Difluoro-quinolin-6-yl-acetic acid ethyl ester (i)

Sodium iodide (4.32 g, 28.8 mmol), copper (I) iodide (137 mg, 0.72 mmol), 6-bromo-quinoline (3 g, 14.4 mmol), N,N'-dimethyl-cyclohexane (0.227 ml, 1.44 mmol) and dioxane were charged in microwave tube (25 mL). The tube was flushed with nitrogen for 10 min and sealed with a Teflon septum. The reaction mixture was stirred at 110° C. for 15 hours. Then the suspension was allowed to cooled to rt, poured into ice-water and extracted with DCM. The crude was purified by silica gel column to give 6-iodo-quinoline as a little green solid (3.5 g, 92%).

To a suspension of 6-iodo-quinoline (i) (1.0 g, 4 mmol) and Cu (0) (559 mg, 8.8 mmol) in dry DMSO was added bromodifluoro-acetic acid ethyl ester (893 mg, 4.4 mmol). The reaction mixture was stirred under $N_2$ at 55° C. for 15 hours. The mixture was poured into the solution of $K_2CO_3$ and extracted with EtOAc. The organic layer was collected and dried with $MgSO_4$. The crude was purified by silica gel column to give difluoro-quinolin-6-yl-acetic acid ethyl ester as a red oil (310 mg, 30%). $^1$H-NMR (CDCl$_3$) δ ppm 1.33 (t, J=7.2, 3H); 4.334 (q, J=7.2, 2H); 7.52 (m, 1H); 7.93 (m, 1H); 8.15 (s, 1H); 8.20-8.23 (m, 2H); 9.03 (s, 1H).

Difluoro-quinolin-6-yl-acetic acid hydrazide (ii)

Difluoro-quinolin-6-yl-acetic acid ethyl ester (836 mg, 3.33 mmol) was dissolved in MeOH (13 ml). Hydrate hydrazine (1.5 ml, 16.8 mmol) was added in the reaction mixture. The mixture was heated to 45° C. for 30 min, cooled to room temperature, concentrated, and taken up in DCM. The organic layer was dried over $MgSO_4$, filtered and concentrated in vacuo to give the crude product, which was purified by silica gel column to give difluoro-quinolin-6-yl-acetic acid hydrazide as a light orange solid (400 mg, 51%), $^1$H-NMR (CDCl$_3$) δ ppm 3.99 (brs, 2H); 7.51 (m, 1H); 7.92 (m, 1H); 8.15 (s, 1H); 8.20-8.26 (q, 2H); 9.02 (m, 1H).

6-[(6-chloro-[1,2,4]triazolo[4,3-b]pyridazin-3-yl)-difluoro-methyl]-quinoline (Intermediate M)

3,6-dichloropyridazine (160 mg, 1.07 mmol) and difluoro-quinolin-6-yl-acetic acid hydrazide (254 mg, 1.07 mmol) were added in n-BuOH (20 mL). The reaction mixture was heated to 130° C. for 12 hours. The solvent was removed by vacuo. The crude was extracted by the solution of $K_2CO_3$ and EtOAc. The organic layer was collected and concentrated to give a solid, which was purified by silica gel column to give 6-[(6-chloro-[1,2,4]triazolo[4,3-b]pyridazin-3-yl)-difluoro-methyl]-quinoline as a black solid (190 mg, 53%). $^1$H-NMR (DMSO) δ ppm 7.62 (m, 2H); 7.90 (m, 1H); 8.22 (m, 1H); 8.35 (m, 1H); 8.65 (m, 2H); 9.02 (m, 1H).

Intermediate N

1-Methylhydrazinecarboxamide

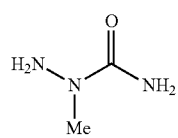

To a solution of sodium cyanate (13 g, 200 mmol) in water (70 mL) was added 40% aq. methylhydrazine (24 mL, 210 mmol) at 0° C., followed by dropwise addition of conc. hydrochloric acid (18 mL) at 0° C. The resulting mixture was stirred at rt overnight, and then filtered. The filtrate was concentrated and dried on lyophilizer to obtain 14 g of crude 2-methyl semicarbazide as white solid. This crude product was purified by flash chromatography (MeOH:DCM=1:4) to afford the title compound as white solid. $^1$H-NMR (400 MHz, DMSO-d$_6$) δ ppm 5.92 (s, 2H), 4.45 (s, 2H), 2.91 (s, 3H).

Intermediate O

N-methylhydrazinecarboxamide

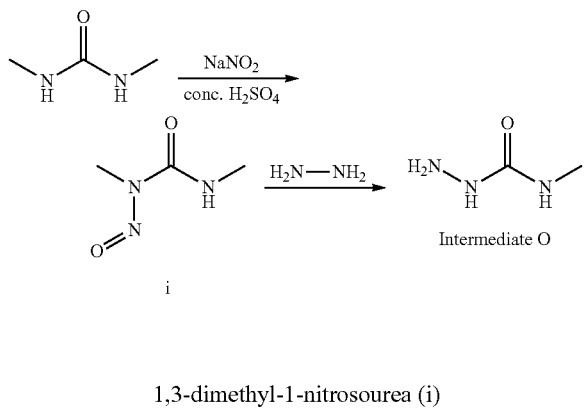

1,3-dimethyl-1-nitrosourea (i)

A solution of sulfuric acid (6.0 mL of conc. sulfuric acid, 113 mmol) in water (100 mL) was added dropwise over 1 h to a chilled solution of 1,3-dimethylurea (10 g, 113 mmol) and sodium nitrite (8.61 g, 125 mmol) in water (150 mL). A white solid was precipitated. After filtration, the filtrate cake was dried and recrystallized from carbon tetrachloride to afford 7.8 g of the title compounds as a pale yellow needle crystal solid. $^1$H-NMR (400 MHz, CDCl$_3$) δ ppm 6.93 (s, 1H), 3.21 (s, 3H), 3.08 (d, 3H).

N-methyl hydrazinecarboxamide (Intermediate O)

To a solution of 1,3-dimethyl-1-nitrosourea (1.0 g, 8.54 mmol) in water (10 mL) was added hydrazine monohydrate (2 mL, 64.3 mmol) at 0° C. The reaction mixture was stirred at rt overnight, and water was removed. The residue was dried on lyophilizer to afford 810 mg of the title compound as a white solid. $^1$H-NMR (400 MHz, DMSO-d$_6$) δ ppm 6.87 (s, 1H), 6.23 (s, 1H), 3.82 (s br, 2H), 2.56 (d, 3H).

Intermediate P

1-Ethylhydrazinecarboxamide

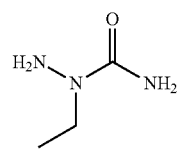

This title compound was prepared using the same procedure as described in the synthesis of intermediate N with ethylhydrazine $^1$H-NMR (400 MHz, DMSO-d$_6$) δ ppm 5.91 (s, 2H), 4.37 (s, 2H), 3.33 (q, 2H), 1.00 (t, 3H).

Example 1

(E)-2-(1-(3-((7-Fluoroquinolin-6-yl)methyl)imidazo[1,2-b]pyridazin-6-yl)ethylidene)-hydrazinecarboxamide

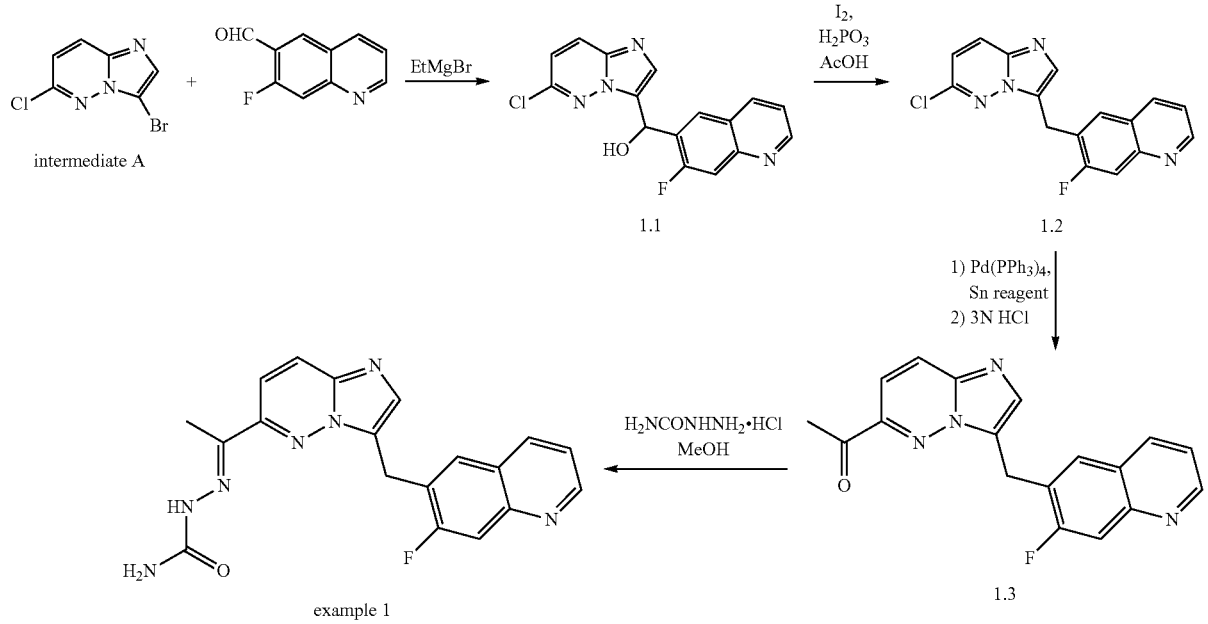

example 1

6-Chloro-imidazo[1,2-b]pyridazin-3-yl)-(7-fluoro-quinolin-6-yl)-methanol (1.1)

To a solution of 3-bromo-6-chloro-imidazo[1,2-b]pyridazine (13.27 g, 57.1 mmol) in 160 ml of THF was added EtMgBr (68.5 ml, 68.5 mmol) solution at room temperature. The reaction mixture was stirred for 30 min and a suspension of 7-Fluoro-quinoline-6-carbaldehyde (10 g, 57.1 mmol) in 40 ml of THF was added. The resulting mixture was stirred at room temperature for 3 hrs and quenched with 400 ml of water. After stirring for additional 1 hr, the precipitate was collected by filtration, washed with EtOAc and dried over vacuum oven overnight to afford 13 g (yield: 69%) of title compound. $^1$H-NMR (400 MHz, DMSO-$d_6$) δ ppm 8.91 (dd, 1H), 8.49 (d, 1H), 8.28 (d, 1H), 8.24 (d, 1H), 7.74 (d, 1H), 7.54 (q, 1H), 7.51 (s, 1H), 7.40 (d, 1H), 6.54 (m, 2H).

6-(6-Chloro-imidazo[1,2-b]pyridazin-3-ylmethyl)-7-fluoro-quinoline (1.2)

To a solution of 6-chloro-imidazo[1,2-b]pyridazin-3-yl)-(7-fluoro-quinolin-6-yl)-methanol (9.48 g, 28.8 mmol) in acetic acid (80 mL) was added phosphinic acid (50% aqueous solution, 15.73 ml, 144 mmol) and iodine (18.3 g, 72.1 mmol). The resulting solution was heated up to 110° C. and stirred overnight. The solvent was removed under reduced pressure. The residue was diluted with water and its pH was adjusted to 8~10 with 6N NaOH solution. The result solution was extracted with $CH_2Cl_2$ and the combined organice layers were washed with brine, dried over anhydrous $Na_2SO_4$ and concentrated in vacuo. The residue was purified by column chromatography (5% to 10% MeOH in $CH_2Cl_2$) to afford 5.8 g (yield: 64.3%) title compound. $^1$H-NMR (400 MHz, CDCl$_3$) δ ppm 8.91 (dd, 1H), 8.14 (d, 1H), 7.93 (d, 1H), 7.85 (d, 1H), 7.75 (d, 1H), 7.66 (s, 1H), 7.41 (q, 1H), 7.09 (d, 1H), 4.56 (s, 2H). LCMS (method B): [MH]$^+$=313, $t_R$=2.48 min.

1-[3-(7-Fluoro-quinolin-6-ylmethyl)-imidazo[1,2-b]pyridazin-6-yl]-ethanone (1.3)

A flask was charged with tetrakis-(triphenylphosphine)-palladium (1.7 g, 1.48 mmol) under nitrogen. A solution of 6-(6-Chloro-imidazo[1,2-b]pyridazin-3-ylmethyl)-7-fluoro-quinoline (5.8 g, 18.55 mmol) in DMF (150 mL) was added. The flask was purged with nitrogen gas three times and tributyl-(1-ethoxy-vinyl)-stannane (6.59 ml, 19.47 mmol) was added. The temperature was increased to 100° C. and stirred overnight. The reaction mixture was cooled to room temperature, 20 ml of 3N HCl was added and the mixture was stirred for additional 2 hrs. Water was added and the product was then extracted with EtOAc, dried over $Na_2SO_4$ and concentrated under reduced pressure. The residue was purified by column chromatography to afford 4.8 g (yield: 79%) title compound as a dark yellow solid. $^1$H-NMR (400 MHz, MeOH-$d_4$) δ ppm 8.82 (dd, 1H), 8.31 (d, 1H), 8.10 (d, 1H), 7.98 (d, 1H), 7.85 (s, 1H), 7.78 (d, 1H), 7.72 (d, 1H), 7.50 (q, 1H), 4.72 (s, 2H), 2.68 (S, 3H). LCMS (method A): [MH]$^+$= 321, $t_R$=5.07 min.

(E)-2-(1-(3-((7-Fluoroquinolin-6-yl)methyl)imidazo[1,2-b]pyridazin-6-yl)ethylidene)-hydrazinecarboxamide (Example 1)

To a solution of 1-[3-(7-fluoro-quinolin-6-ylmethyl)-imidazo[1,2-b]pyridazin-6-yl]-ethanone (320 mg, 1 mmol) in methanol (30 mL) was added semicarbazide hydrochloride (334 mg, 3.0 mmol). Triethyl amine was added dropwise to the reaction mixture to adjust the pH to 5~6. The reaction mixture was stirred at room temperature overnight. The precipitate was collected by filtration and dried over vacuum pump to afford 250 mg (yield: 66%) title compound as a white solid. ¹H-NMR 400 MHz, DMSO-d₆) δ ppm 9.69 (s, 1H), 8.85 (dd, 1H), 8.30 (d, 1H), 8.21 (d, 1H), 7.98 (d, 1H), 7.94 (d, 1H), 7.77 (d, 1H), 7.66 (s, 1H), 7.47 (q, 1H), 6.73 (b, 2H), 4.56 (s, 2H), 2.23 (s, 3H). LCMS (method A): [MH]⁺=378, $t_R$=4.64 min.

Example 2

(E)-6-((6-(1-(2-Ethylhydrazono)ethyl)imidazo[1,2-b]pyridazin-3-yl)methyl)-7-fluoroquinoline

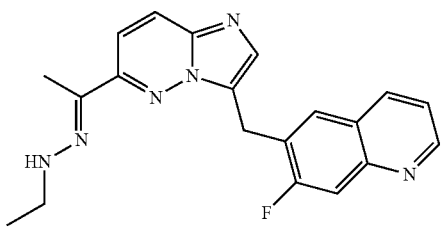 [SMILES: CCN/N=C(\C)c1ccc2ncc(Cc3cc4cccnc4cc3F)n2n1]

The title compound was prepared from ethyl hydrazine and 1-[3-(7-fluoro-quinolin-6-ylmethyl)-imidazo[1,2-b]pyridazin-6-yl]-ethanone in analogy to the synthesis of example 1 in 32% yield. ¹H-NMR (400 MHz, MeOH -d₄) δ ppm 8.81 (dd, 1H), 8.27 (d, 1H), 7.92 (d, 1H), 7.88 (d, 1H), 7.78 (d, 1H), 7.69 (d, 1H), 7.54 (s, 1H), 7.47 (q, 1H), 4.59 (s, 2H), 3.38 (q, 2H), 2.13 (s, 3H), 1.22 (t, 3H). LCMS (method A): [MH]⁺=363, $t_R$=5.32 min.

Example 3

(E)-N'-(1-(3-((7-Fluoroquinolin-6-yl)methyl)imidazo[1,2-b]pyridazin-6-yl)ethylidene)-acetohydrazide

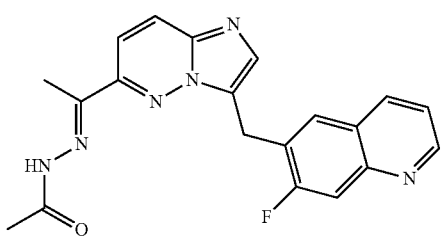 [SMILES: CC(=O)N/N=C(\C)c1ccc2ncc(Cc3cc4cccnc4cc3F)n2n1]

The title compound was prepared from acetic hydrazide and 1-[3-(7-fluoro-quinolin-6-ylmethyl)-imidazo[1,2-b]pyridazin-6-yl]-ethanone in analogy to the synthesis of example 1 in 75% yield as a white solid. ¹H-NMR (400 MHz, DMSO-d₆) δ ppm 8.86 (d, 1H), 8.83 (d, 1H), 8.07 (d, 1H), 7.95 (d, 1H), 7.79 (m, 2H), 7.70 (s, 1H), 7.47 (q, 1H), 4.58 (s, 2H), 2.28 (s, 3H). LCMS (method A): [MH]⁺=377, $t_R$=4.83 min.

Example 4

(E)-7-Fluoro-6-((6-(1-(2-phenylhydrazono)ethyl)imidazo[1,2-b]pyridazin-3-yl)methyl)-quinoline

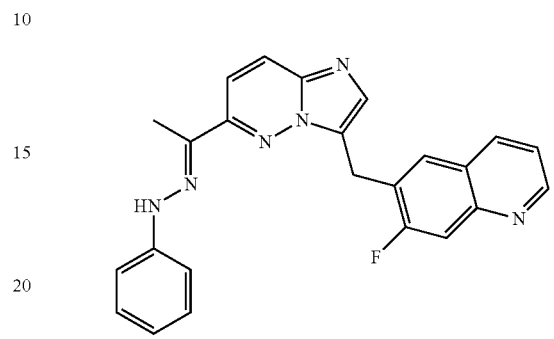

The title compound was prepared from phenyl hydrazine and 1-[3-(7-fluoro-quinolin-6-ylmethyl)-imidazo[1,2-b]pyridazin-6-yl]-ethanone in analogy to the synthesis of example 1 in 32% yield as a yellow solid. ¹H-NMR (400 MHz, DMSO-d₆) δ ppm 9.78 (s, 1H), 8.86 (dd, 1H), 8.32 (d, 1H), 7.98 (m, 3H), 7.78 (d, 1H), 7.61 (s, 1H), 7.47 (q, 1H), 7.30 (m, 4H), 6.83 (t, 1H), 4.57 (s, 2H), 2.31 (s, 3H). LCMS (method C): [MH]⁺=411, $t_R$=4.57 min.

Example 5

(E)-7-Fluoro-6-((6-(1-(2-(pyridin-2-yl)hydrazono)ethyl)imidazo[1,2-b]pyridazin-3-yl)methyl)quinoline

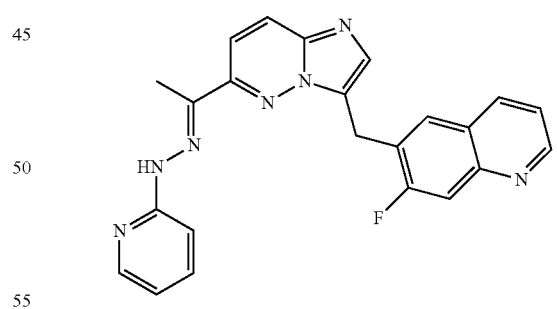

The title compound was prepared from pyridin-2-yl-hydrazine and 1-[3-(7-fluoro-quinolin-6-ylmethyl)-imidazo[1,2-b]pyridazin-6-yl]ethanone in analogy to the synthesis of example 1 in 48% yield as a white solid. ¹H-NMR (400 MHz, DMSO-d₆) δ ppm 10.27 (s, 1H), 8.86 (dd, 1H), 8.31 (d, 1H), 8.19 (d, 1H), 7.97 (m, 3H), 7.78 (d, 1H), 7.70 (t, 1H), 7.65 (s, 1H), 7.47 (q, 1H), 7.40 (d, 1H), 6.87 (dd, 1H), 4.58 (s, 2H), 2.36 (s, 3H). LCMS (method A): [MH]⁺=412, $t_R$=4.78 min.

Example 6

(E)-2-(1-(3-((7-Fluoroquinolin-6-yl)methyl)imidazo[1,2-b]pyridazin-6-yl)ethylidene)-N-phenylhydrazinecarboxamide

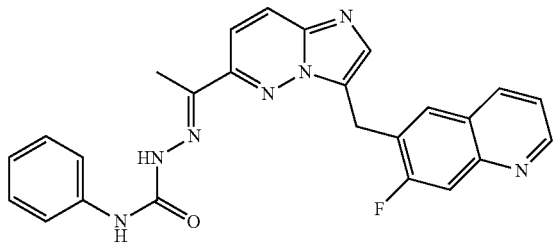 [SMILES: C/C(=N\NC(=O)Nc1ccccc1)c1ccc2ncc(Cc3cc4cccnc4cc3F)n2n1]

The title compound was prepared from N-phenylhydrazine carboxamide and 1-[3-(7-fluoro-quinolin-6-ylmethyl)-imidazo[1,2-b]pyridazin-6-yl]-ethanone in analogy to the synthesis of example 1 in 36% yield. ¹H-NMR (400 MHz, DMSO-d₆) δ ppm 10.13 (s, 1H), 9.06 (s, 1H), 8.86 (dd, 1H), 8.30 (t, 2H), 8.06 (d, 1H), 7.96 (d, 1H), 7.78 (d, 1H), 7.69 (s, 1H), 7.60 (d, 2H), 7.48 (q, 1H), 7.31 (t, 2H), 7.04 (t, 1H), 4.58 (s, 2H), 2.32 (s, 3H). LCMS (method C): [MH]⁺=454, $t_R$=3.89 min.

Example 7

(E)-N-(4-Chlorophenyl)-2-(1-(3-((7-fluoroquinolin-6-yl)methyl)imidazo[1,2-b]pyridazin-6-yl)ethylidene)hydrazinecarboxamide

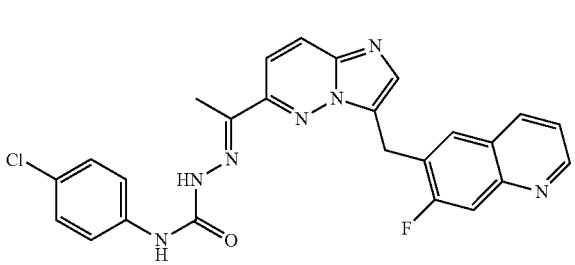 [SMILES: C/C(=N\NC(=O)Nc1ccc(Cl)cc1)c1ccc2ncc(Cc3cc4cccnc4cc3F)n2n1]

The title compound was prepared from N-p-chlorophenylhydrazine carboxamide and 1-[3-(7-fluoro-quinolin-6-ylmethyl)-imidazo[1,2-b]pyridazin-6-yl-]ethanone in analogy to the synthesis of example 1. ¹H-NMR (400 MHz, DMSO-d₆) δ ppm 10.20 (s, 1H), 9.18 (s, 1H), 8.86 (dd, 1H), 8.31 (m, 2H), 8.07 (d, 1H), 7.96 (d, 1H), 7.78 (d, 1H), 7.67 (m, 3H), 7.48 (q, 1H), 7.36 (d, 2H), 4.58 (s, 2H), 2.32 (s, 3H). LCMS (method C): [MH]⁺=489, $t_R$=4.35 min.

Example 8

(E)-2-(1-(3-((7-Fluoroquinolin-6-yl)methyl)imidazo[1,2-b]pyridazin-6-yl)ethylidene)-1-methylhydrazinecarboxamide

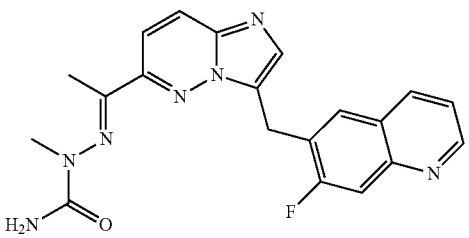

The title compound was prepared from 1-methylhydrazine carboxamide and 1-[3-(7-fluoro-quinolin-6-ylmethyl)-imidazo[1,2-b]pyridazin-6-yl]-ethanone in analogy to the synthesis of example 1 in 21% yield. ¹H-NMR (400 MHz, DMSO-d₆) δ ppm 8.86 (dd, 1H), 8.31 (d, 1H), 8.05 (s, 2H), 7.97 (d, 1H), 7.77 (d, 1H), 7.72 (s, 1H), 7.47 (q, 1H), 6.54 (s, 2H), 4.58 (s, 2H), 3.19 (s, 3H), 2.37 (s, 3H). LCMS (method A): [MH]⁺=392, $t_R$=4.76 min.

Example 9

(E)-2-(1-(3-((7-Fluoroquinolin-6-yl)methyl)imidazo[1,2-b]pyridazin-6-yl)ethylidene)-N,1-dimethylhydrazinecarboxamide

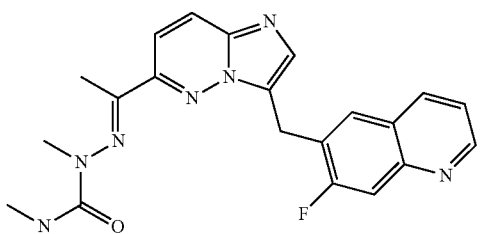

The title compound was prepared from N,1-dimethylhydrazine carboxamide and 1-[3-(7-fluoro-quinolin-6-ylmethyl)-imidazo[1,2-b]pyridazin-6-yl]-ethanone in analogy to the synthesis of example 1 in 21% yield. ¹H-NMR (400 MHz, DMSO-d₆) δ ppm 8.86 (dd, 1H), 8.31 (d, 1H), 8.06 (m, 2H), 7.97 (d, 1H), 7.77 (d, 1H), 7.73 (s, 1H), 7.47 (q, 1H), 6.90 (q, 1H), 4.59 (s, 2H), 3.19 (s, 3H), 2.68 (d, 3H), 2.37 (s, 3H). LCMS (method B): [MH]+=406, t$_R$=2.27 min.

Example 10

(E)-3-(1-(3-((7-Fluoroquinolin-6-yl)methyl)imidazo[1,2-b]pyridazin-6-yl)ethylidene-amino)oxazolidin-2-one

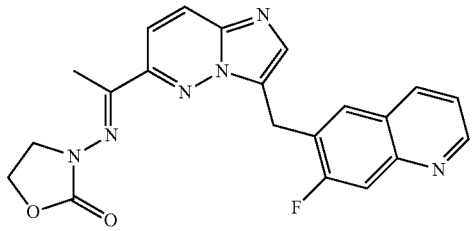 [SMILES: C/C(=N\N1CCOC1=O)c1ccc2ncc(Cc3cc4cccnc4cc3F)n2n1]

The title compound was prepared from 3-aminooxazolidin-2-one and 1-[3-(7-fluoro-quinolin-6-ylmethyl)-imidazo[1,2-b]pyridazin-6-yl]-ethanone in analogy to the synthesis of example 1 in 24% yield. $^1$H-NMR (400 MHz, CDCl$_3$) δ ppm 8.85 (dd, 1H), 8.02 (d, 1H), 7.88 (m, 2H), 7.71 (m, 3H), 7.33 (q, 1H), 4.58 (s, 2H), 4.51 (t, 2H), 4.01 (t, 2H), 2.49 (s, 3H). LCMS (method A): [MH]+=405, t$_R$=4.76 min.

Example 11

(E)-1-(1-(3-((7-Fluoroquinolin-6-yl)methyl)imidazo[1,2-b]pyridazin-6-yl)ethylidene-amino)imidazolidine-2,4-dione

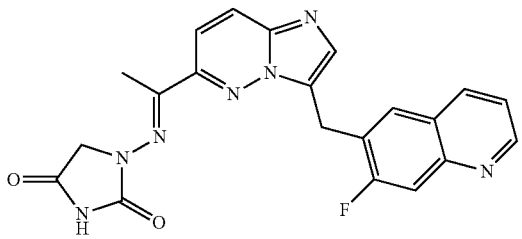 [SMILES: C/C(=N\N1CC(=O)NC1=O)c1ccc2ncc(Cc3cc4cccnc4cc3F)n2n1]

The title compound was prepared from 1-aminoimidazolidine-2,4-dione hydrochloride and 1-[3-(7-fluoro-quinolin-6-ylmethyl)-imidazo[1,2-b]pyridazin-6-yl]-ethanone in analogy to the synthesis of example 1 in 39% yield. $^1$H-NMR (400 MHz, DMSO-d$_6$) δ ppm 11.39 (s, 1H), 8.91 (dd, 1H), 8.40 (d, 1H), 8.24 (d, 1H), 8.04 (d, 1H), 7.94 (m, 2H), 7.82 (d, 1H), 7.55 (q, 1H), 4.64 (s, 2H), 4.50 (s, 2H), 2.40 (s, 3H). LCMS (method A): [MH]+=418, t$_R$=4.62 min.

Example 12

(E)-2-(2-(1-(3-((7-Fluoroquinolin-6-yl)methyl)imidazo[1,2-b]pyridazin-6-yl)ethylidene)-hydrazinyl)benzo[d]oxazole

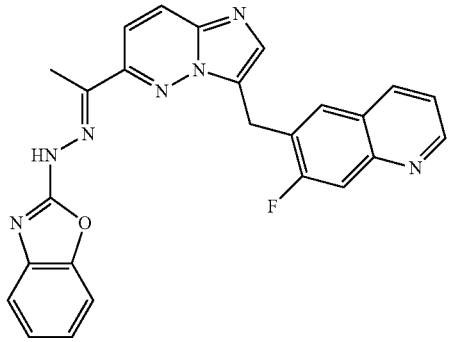 [SMILES: C/C(=N\Nc1nc2ccccc2o1)c1ccc2ncc(Cc3cc4cccnc4cc3F)n2n1]

The title compound was prepared from 2-hydrazinylbenzo[d]oxazole and 1-[3-(7-fluoro-quinolin-6-ylmethyl)-imidazo[1,2-b]pyridazin-6-yl]-ethanone in analogy to the synthesis of example 1 in 74% yield. $^1$H-NMR (400 MHz, DMSO-d$_6$) δ ppm 11.8-11.5 (m, 1H), 8.87 (dd, 1H), 8.4-7.9 (m, 4), 7.8-7.6 (m, 2H), 7.6-7.1 (m, 5H), 4.58 (s, 2H), 2.49 (s, 3H). LCMS (method C): [MH]+=452, t$_R$=4.42 min.

Example 13

(E)-N'-(1-(3-((7-Fluoroquinolin-6-yl)methyl)imidazo[1,2-b]pyridazin-6-yl)ethylidene)-methanesulfonohydrazide

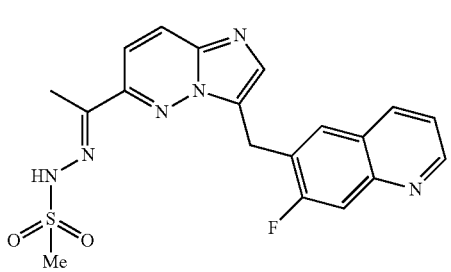 [SMILES: C/C(=N\NS(C)(=O)=O)c1ccc2ncc(Cc3cc4cccnc4cc3F)n2n1]

The title compound was prepared from methanesulfonohydrazide and 1-[3-(7-fluoro-quinolin-6-ylmethyl)-imidazo[1,2-b]pyridazin-6-yl]-ethanone in analogy to the synthesis of example 1 in 60% yield. $^1$H-NMR (400 MHz, DMSO-d$_6$) δ ppm 10.63 (s, 1H), 8.85 (dd, 1H), 8.30 (d, 1H), 8.09 (d, 1H), 7.94 (d, 1H), 7.75 (m, 3H), 7.47 (q, 1H), 4.58 (s, 2H), 3.10 (s, 3H), 2.26 (s, 3H). LCMS (method A): [MH]⁺=413, $t_R$=4.57 min.

Example 14

(E)-N-ethyl-2-(1-(3-((7-Fluoroquinolin-6-yl)methyl) imidazo[1,2-b]pyridazin-6-yl)ethylidene)hydrazin-ecarbothioamide

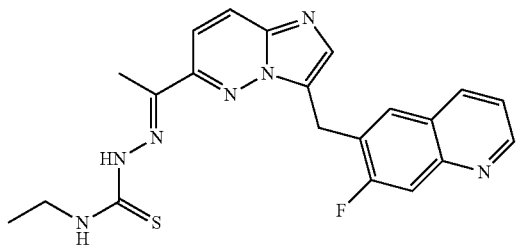 [SMILES: CCNC(=S)N/N=C(\C)c1ccc2ncc(Cc3cc4cccnc4cc3F)n2n1]

The title compound was prepared from N-ethylhydrazine carbothioamide and 1-[3-(7-fluoro-quinolin-6-ylmethyl)-imidazo[1,2-b]pyridazin-6-yl]-ethanone in analogy to the synthesis of example 1 in 53% yield. ¹H-NMR (400 MHz, MeOH-d₄) δ ppm 8.83 (d, 1H), 8.30 (d, 1H), 8.24 (d, 1H), 7.93 (m, 2H), 7.69 (m, 2H), 7.48 (q, 1H), 4.67 (s, 2H), 3.74 (q, 2H), 2.39 (s, 3H), 1.26 (t, 3H). LCMS (method A): [MH]⁺=422, $t_R$=5.43 min.

Example 15

(E)-N-Benzyl-2-(1-(3-((7-fluoroquinolin-6-yl)me-thyl)imidazo[1,2-b]pyridazin-6-yl)ethylidene)hydra-zinecarbothioamide

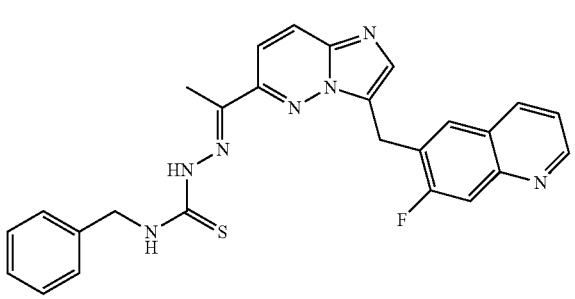 [SMILES: C/C(=N\NC(=S)NCc1ccccc1)c1ccc2ncc(Cc3cc4cccnc4cc3F)n2n1]

The title compound was prepared from N-benzylhydrazine carbothioamide and 1-[3-(7-fluoro-quinolin-6-ylmethyl)-imidazo[1,2-b]pyridazin-6-yl]-ethanone in analogy to the synthesis of example 1 in 80% yield. ¹H-NMR (400 MHz, DMSO-d₆) δ ppm 10.58 (s, 1H), 9.30 (t, 1H), 8.86 (dd, 1H), 8.30 (m, 2H), 8.05 (d, 1H), 7.95 (d, 1H), 7.77 (d, 1H), 7.69 (s, 1H), 7.47 (q, 1H), 7.32 (m, 4H), 7.23 (m, 1H), 4.89 (d, 2H), 4.58 (s, 2H), 2.39 (s, 3H). LCMS (method C): [MH]⁺=484, $t_R$=4.18 min.

Example 16

(E)-2-(1-(3-((7-Fluoroquinolin-6-yl)methyl)imidazo[1,2-b]pyridazin-6-yl)ethylidene)-hydrazinecarboth-ioamide

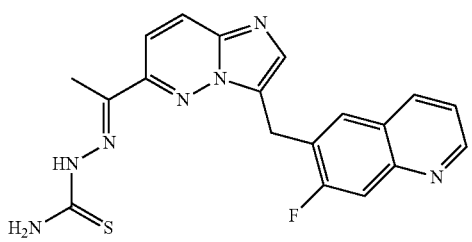 [SMILES: C/C(=N\NC(N)=S)c1ccc2ncc(Cc3cc4cccnc4cc3F)n2n1]

The title compound was prepared from hydrazine carboth-ioamide hydrochloride and 1-[3-(7-fluoro-quinolin-6-ylm-ethyl)-imidazo[1,2-b]pyridazin-6-yl]-ethanone in analogy to the synthesis of example 1 in 60% yield as a white solid. ¹H-NMR (400 MHz, DMSO-d₆) δ ppm 10.53 (s, 1H), 8.88 (dd, 1H), 8.53 (s, 1H), 8.47 (d, 1H), 8.34 (m, 2H), 8.10 (d, 1H), 7.99 (d, 1H), 7.85 (s, 1H), 7.79 (d, 1H), 7.50 (q, 1H), 4.59 (s, 2H), 2.34 (s, 3H). LCMS (method A): [MH]⁺=394, $t_R$=4.91 min.

Example 17

(E)-2-(1-(3-((7-Fluoroquinolin-6-yl)methyl-d)imi-dazo[1,2-b]pyridazin-6-yl)ethylidene)-hydrazinecar-boxamide

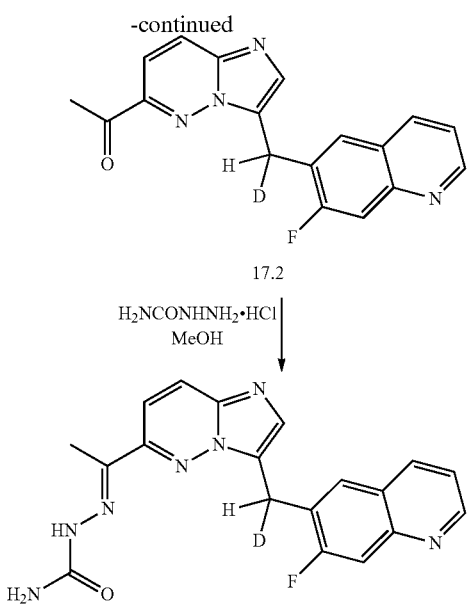

example 17

6-(6-Chloro-imidazo[1,2-b]pyridazin-3-ylmethyl-d)-7-fluoro-quinoline (17.1)

To a sealed tube was added (6-chloro-imidazo[1,2-b]pyridazin-3-yl)-(7-fluoro-quinolin-6-yl)-methanol (150 mg, 0.46 mmol), triethyl silane-d (0.5 mL), trifluoroacetic acid-d (0.5 mL) and 1.5 ml of dichloromethane. The reaction mixture was stirred at 40° C. for 5 days. Then the reaction mixture was quenched with water and neutralized with NaHCO$_3$ solution. The product was extracted with CH$_2$Cl$_2$ and the combined organic layers were washed with brine, dried over Na$_2$SO$_4$ and concentrated under reduced pressure. The residue was purified by column chromatography to afford title compound. LCMS (method B): [MH]$^+$=314, t$_R$=2.39 min.

1-[3-(7-Fluoro-quinolin-6-ylmethyl-d)-imidazo[1,2-b]pyridazin-6-yl]-ethanone (17.2)

In a flask was charged with tetrakis-(triphenylphosphine)-palladium (21 mg, 0.018 mmol) under nitrogen. A solution of 6-(6-Chloro-imidazo[1,2-b]pyridazin-3-ylmethyl-d)-7-fluoro-quinoline in CH$_2$Cl$_2$ (5 mL) was added. The system was purged with nitrogen gas three times and tributyl-(1-ethoxy-vinyl)-stannane (0.063 mL, 0.19 mmol) was added. The temperature was increased to 100° C. and stirred overnight. The reaction mixture was cooled to room temperature, 5 mL of 3N HCl was added and the mixture was stirred for additional 2 hrs. Water was added and the product was extracted with EtOAc, dried over Na$_2$SO$_4$ and concentrated under reduced pressure. The residue was purified by column chromatography (3% to 10% MeOH in CH$_2$Cl$_2$) to afford title compound as a yellow solid. LCMS (method B): [MH]$^+$=322, t$_R$=2.24 min.

(E)-2-(1-(3-((7-Fluoroquinolin-6-yl)methyl-d)imidazo[1,2-b]pyridazin-6-yl)ethylidene)-hydrazinecarboxamide (Example 17)

To a solution of 1-[3-(7-Fluoro-quinolin-6-ylmethyl-d)-imidazo[1,2-b]pyridazin-6-yl]-ethanone in methanol (15 mL) was added semicarbazide hydrochloride (27 mg, 0.25 mmol). Triethyl amine was added dropwise to adjust the pH to 5-6. The reaction mixture was stirred at room temperature overnight. The precipitate was collected by filtration and dried over vacuum pump to afford title compound as a white solid. $^1$H-NMR (400 MHz, DMSO-d$_6$) δ ppm 9.70 (s, 1H), 8.86 (dd, 1H), 8.30 (d, 1H), 8.21 (d, 1H), 7.96 (m, 2H), 7.77 (d, 1H), 7.66 (s, 1H), 7.47 (q, 1H), 6.71 (b, 2H), 4.54 (s, 1H), 2.23 (s, 3H). LCMS (method A): [MH]$^+$=379, t$_R$=4.25 min.

Example 18

(E)-2-(1-(3-((7-Fluoroquinolin-6-yl)methyl-d2)imidazo[1,2-b]pyridazin-6-yl)ethylidene)-hydrazinecarboxamide

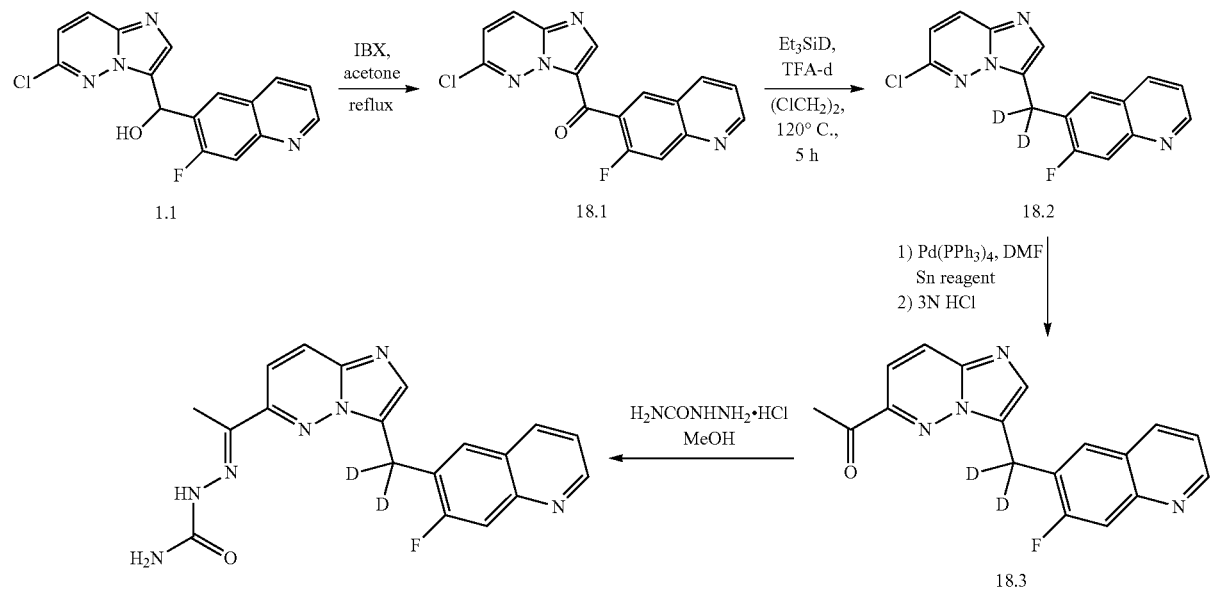

example 18

(6-Chloroimidazo[1,2-b]pyridazin-3-yl)(7-fluoro-quinolin-6-yl)methanone (18.1)

To a suspension of (6-chloro-imidazo[1,2-b]pyridazin-3-yl)-(7-fluoro-quinolin-6-yl)-methanol (1.8 g, 5.48 mmol) in acetone (200 mL) was added 2-iodoxybenzoic acid (8.52 g, 45%, 13.69 mmol) and the reaction mixture was stirred at reflux for 1 day. The solvent was removed under reduced pressure and the residue was dissolved in 200 mL of water. The solution was basified by 3N NaOH solution and the precipitate was collected, washed with water and dried over vacuum oven to afford 1.7 g (yield: 95%) title compound as a gray solid. $^1$H-NMR (400 MHz, DMSO-$d_6$) δ ppm 9.04 (dd, 1H), 8.56 (d, 1H), 8.47 (m, 2H), 8.41 (s, 1H), 7.92 (d, 1H), 7.75 (d, 1H), 7.64 (q, 1H). LCMS (method B): [MH]$^+$=327, $t_R$=2.03 min.

6-(6-Chloro-imidazo[1,2-b]pyridazin-3-ylmethyl-d2)-7-fluoro-quinoline (18.2)

To a microwave tube was added (6-chloroimidazo[1,2-b]pyridazin-3-yl)(7-fluoroquinolin-6-yl)methanone (90 mg, 0.28 mmol), triethyl silane-d (0.7 mL), trifluoroacetic acid-d (0.7 ml) and 2 ml of 1,2-dichloroethane. The reaction mixture was stirred at 120° C. for 5 hrs in microwave reactor. The reaction mixture was quenched with water and neutralized with NaHCO$_3$ solution. The resulting mixture was extracted with CH$_2$Cl$_2$ and the combined organic layers was washed with brine, dried over Na$_2$SO$_4$ and concentrated under reduced pressure. The residue was purified by column chromatography (5% to 10% MeOH in CH$_2$Cl$_2$) to afford 30 mg (yield: 20%) title compound as a yellow solid. $^1$H-NMR (400 MHz, CDCl$_3$) δ ppm 8.88 (dd, 1H), 8.09 (d, 1H), 7.91 (d, 1H), 7.77 (d, 1H), 7.72 (d, 1H), 7.64 (s, 1H), 7.36 (q, 1H), 7.05 (d, 1H). LCMS (method B): [MH]$^+$=315, $t_R$=2.39 min.

1-[3-(7-Fluoro-quinolin-6-ylmethyl-d2)-imidazo[1,2-b]pyridazin-6-yl]-ethanone (18.3)

In a flask was charged with tetrakis-(triphenylphosphine)-palladium (21 mg, 0.018 mmol) under nitrogen. A solution of 6-(6-chloro-imidazo[1,2-b]pyridazin-3-ylmethyl-d2)-7-fluoro-quinoline in CH$_2$Cl$_2$ (10 mL) was added. The system was purged with nitrogen gas three times and then tributyl-(1-ethoxy-vinyl)-stannane (0.063 ml, 0.19 mmol) was added. The temperature was increased to 100° C. and stirred overnight. Then the reaction mixture was cooled to room temperature, 5 mL of 3N HCl was added and the mixture was stirred for additional 2 hrs. Water was added and the mixture was then extracted with EtOAc, dried over Na$_2$SO$_4$ and concentrated under reduced pressure. The residue was purified by column chromatography (3% to 10% MeOH in CH$_2$Cl$_2$) to afford title compound as a dark yellow solid. LCMS (method B): [MH]$^+$=323, $t_R$=2.24 min.

(E)-2-(1-(3-((7-Fluoroquinolin-6-yl)methyl-d2)imidazo[1,2-b]pyridazin-6-yl)ethylidene)-hydrazinecarboxamide (Example 18)

To a solution of 1-[3-(7-fluoro-quinolin-6-ylmethyl-d2)-imidazo[1,2-b]pyridazin-6-yl]-ethanone in methanol (10 mL) was added semicarbazide hydrochloride (29 mg, 0.25 mmol). Triethyl amine was then added dropwise to adjust the pH to 5-6. The reaction mixture was stirred at room temperature overnight. The precipitate was collected by filtration and dried over vacuum pump to afford the title compound as a light yellow solid. $^1$H-NMR (400 MHz, DMSO-$d_6$) δ ppm 9.70 (s, 1H), 8.86 (s, 1H), 8.30 (d, 1H), 8.21 (d, 1H), 7.96 (m, 2H), 7.77 (d, 1H), 7.66 (s, 1H), 7.47 (q, 1H), 6.73 (b, 2H), 2.23 (s, 3H). LCMS (method A): [MH]$^+$=380, $t_R$=4.18 min.

Example 19

(E)-2-(1-(3-(Quinolin-6-ylmethyl)imidazo[1,2-b]pyridazin-6-yl)ethylidene)-hydrazine-carboxamide

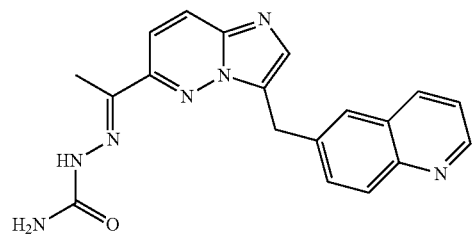 [SMILES: C/C(=N\NC(N)=O)c1ccc2ncc(Cc3ccc4ncccc4c3)n2n1]

The title compound was prepared in analogy to the synthesis of example 1 as a white solid. $^1$H-NMR (400 MHz, DMSO-$d_6$) δ ppm 9.70 (s, 1H), 8.83 (dd, 1H), 8.29 (d, 1H), 8.19 (d, 1H), 7.95 (m, 3H), 7.75 (d, 1H), 7.68 (s, 1H), 7.47 (q, 1H), 6.74 (b, 2H), 4.53 (s, 2H), 2.25 (s, 3H). LCMS (method A): [MH]$^+$=360, $t_R$=3.84 min.

Example 20

(E)-2-(1-(3-((5,7-Difluoroquinolin-6-yl)methyl)imidazo[1,2-b]pyridazin-6-yl)ethylidene)-hydrazinecarboxamide

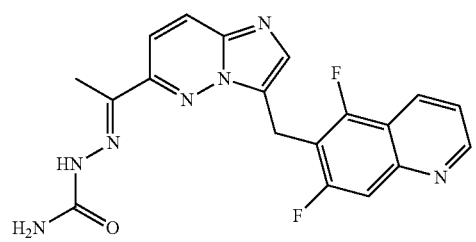 [SMILES: C/C(=N\NC(N)=O)c1ccc2ncc(Cc3c(F)cc4ncccc4c3F)n2n1]

The title compound was prepared in analogy to the synthesis of example 1 as a white solid. $^1$H-NMR (400 MHz, DMSO-$d_6$) δ ppm 9.69 (s, 1H), 8.96 (d, 1H), 8.46 (d, 1H), 8.19 (d, 1H), 7.95 (d, 1H), 7.70 (d, 1H), 7.63 (s, 1H), 7.60 (q, 1H), 6.67 (b, 2H), 4.57 (s, 2H), 2.24 (s, 3H). LCMS (method A): [MH]$^+$=396, $t_R$=5.08 min.

Example 21

(E)-2-(1-(3-((5,7-Difluoroquinolin-6-yl)methyl)imidazo[1,2-b]pyridazin-6-yl)ethylidene)-1-methylhydrazinecarboxamide

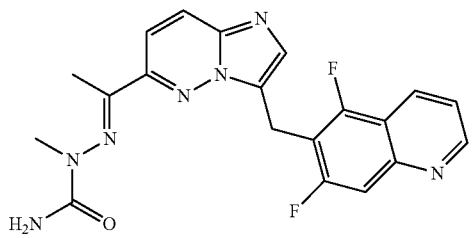 [SMILES: C/C(=N\N(C)C(N)=O)c1ccc2ncc(Cc3c(F)cc4ncccc4c3F)n2n1]

The title compound was prepared in analogy to the synthesis of example 8. $^1$H-NMR (400 MHz, DMSO-d$_6$) δ ppm 8.96 (d, 1H), 8.47 (d, 1H), 8.01 (s, 2H), 7.69 (m, 2H), 7.61 (q, 1H), 6.54 (s, 2H), 4.60 (s, 2H), 3.19 (s, 3H), 2.37 (s, 3H). LCMS (method A): [MH]$^+$=410, $t_R$=5.19 min.

Example 22

(E)-2-(1-(3-((7-Fluoroquinolin-6-yl)(hydroxy)methyl)imidazo[1,2-b]pyridazin-6-yl)ethylidene)hydrazinecarboxamide

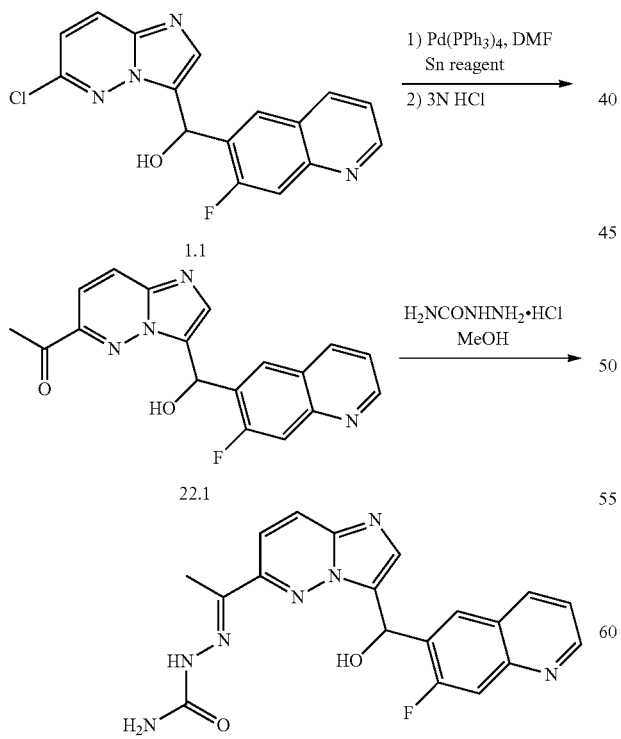

example 22

1-(3-((7-Fluoroquinolin-6-yl)(hydroxy)methyl)imidazo[1,2-b]pyridazin-6-yl)ethanone (22.1)

A flask was charged with tetrakis-(triphenylphosphine)-palladium (176 mg, 0.15 mmol) under nitrogen. A solution of (6-chloroimidazo[1,2-b]pyridazin-3-yl)(7-fluoroquinolin-6-yl)methanol (500 mg, 1.52 mmol) in CH$_2$Cl$_2$ (20 mL) was added. The system was purged with nitrogen gas three times and tributyl-(1-ethoxy-vinyl)-stannane (0.54 ml, 1.59 mmol) was added. The temperature was increased to 100° C. and stirred overnight. The reaction mixture was cooled to room temperature, 3N HCl was added and the mixture was stirred for additional 4 hrs. Water was added and the mixture was then extracted with EtOAc, dried over Na$_2$SO$_4$ and concentrated under reduced pressure. The residue was purified by column chromatography (3% to 10% MeOH in CH$_2$Cl$_2$) to afford 500 mg (yield: 88%) title compound. LCMS (method B): [MH]$^+$=337, $t_R$=1.88 min.

(E)-2-(1-(3-((7-Fluoroquinolin-6-yl)(hydroxy)methyl)imidazo[1,2-b]pyridazin-6-yl)ethylidene)hydrazinecarboxamide (Example 22)

To a solution of 1-(3-((7-fluoroquinolin-6-yl)(hydroxy)methyl)imidazo[1,2-b]pyridazin-6-yl)ethanone (100 mg, 0.27 mmol) in methanol (15 mL) was added semicarbazide hydrochloride (45 mg, 0.41 mmol). Triethyl amine was added dropwise to adjust the pH to 5-6. The reaction mixture was stirred at room temperature overnight. The precipitate was collected by filtration and dried over vacuum pump to afford 50 mg (yield: 47%) title compound as a white solid. $^1$H-NMR (400 MHz, DMSO-d$_6$) δ ppm 9.68 (s, 1H), 8.89 (dd, 1H), 8.45 (d, 1H), 8.25 (m, 2H), 7.99 (d, 1H), 7.72 (d, 1H), 7.57 (s, 1H), 7.52 (q, 1H), 6.67 (b, 2H), 6.62 (s, 1H), 6.47 (b, 1H), 2.19 (s, 3H). LCMS (method A): [MH]$^+$=394, $t_R$=3.95 min.

Example 23

(E)-2-(1-(3-(Hydroxy(quinolin-6-yl)methyl)imidazo[1,2-b]pyridazin-6-yl)ethylidene)-hydrazinecarboxamide

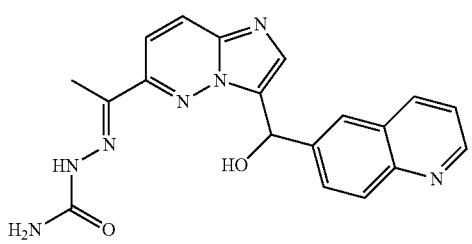 [SMILES: C/C(=N\NC(N)=O)c1ccc2ncc(C(O)c3ccc4ncccc4c3)n2n1]

The title compound was prepared in analogy to the synthesis of example 22 as a white solid. $^1$H-NMR (400 MHz, DMSO-d$_6$) δ ppm 9.69 (s, 1H), 8.86 (dd, 1H), 8.37 (d, 1H), 8.20 (d, 1H), 8.12 (s, 1H), 7.98 (d, 2H), 7.85 (d, 1H), 7.65 (s, 1H), 7.52 (q, 1H), 6.70 (b, 2H), 6.44 (s, 1H), 6.34 (b, 1H), 2.24 (s, 3H). LCMS (method A): [MH]⁺=376, $t_R$=3.25 min.

Example 24

(E)-2-(1-(3-((7-Fluoroquinolin-6-yl)(hydroxy)methyl)imidazo[1,2-b]pyridazin-6-yl)ethylidene)-1-methylhydrazinecarboxamide

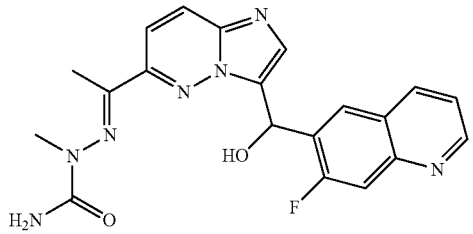 [SMILES: C/C(=N\N(C)C(N)=O)c1ccc2ncc(C(O)c3cc4cccnc4cc3F)n2n1]

The title compound was prepared in analogy to the synthesis of example 22. ¹H-NMR (400 MHz, DMSO-d₆) δ ppm 8.88 (d, 1H), 8.46 (d, 1H), 8.30 (d, 1H), 8.04 (s, 2H), 7.72 (d, 1H), 7.61 (s, 1H), 7.52 (q, 1H), 6.64 (d, 1H), 6.55 (s, 2H), 6.51 (d, 1H), 3.19 (s, 3H), 2.33 (s, 3H). LCMS (method A): [MH]⁺= 408, $t_R$=4.16 min.

Example 25

(E)-2-(1-(3-((5,7-Difluoroquinolin-6-yl)(hydroxy)methyl)imidazo[1,2-b]pyridazin-6-yl)ethylidene)hydrazinecarboxamide

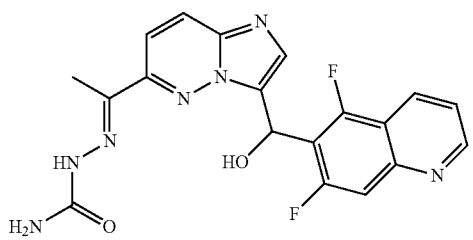 [SMILES: C/C(=N\NC(N)=O)c1ccc2ncc(C(O)c3c(F)cc4ncccc4c3F)n2n1]

The title compound was prepared in analogy to the synthesis of example 22 as a white solid. ¹H-NMR (400 MHz, DMSO-d₆) δ ppm 9.63 (s, 1H), 8.97 (dd, 1H), 8.47 (d, 1H), 8.16 (d, 1H), 7.96 (d, 1H), 7.84 (s, 1H), 7.66 (d, 1H), 7.60 (q, 1H), 6.75 (d, 1H), 6.70 (b, 2H), 6.65 (d, 1H), 2.06 (s, 3H). LCMS (method A): [MH]⁺=412, $t_R$=4.09 min.

Example 26

(E)-2-(1-(3-((5,7-Difluoroquinolin-6-yl)(hydroxy)methyl)imidazo[1,2-b]pyridazin-6-yl)ethylidene)-1-methylhydrazinecarboxamide

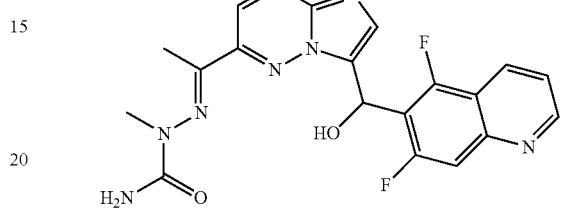

The title compound was prepared in analogy to the synthesis of example 22. ¹H-NMR (400 MHz, DMSO-d₆) δ ppm 8.97 (d, 1H), 8.48 (d, 1H), 8.00 (m, 2H), 7.90 (s, 1H), 7.66 (d, 1H), 7.60 (q, 1H), 6.74 (m, 2H), 6.51 (s, 2H), 3.14 (s, 3H), 2.19 (s, 3H). LCMS (method A): [MH]⁺=426, $t_R$=4.29 min.

Example 27

(E)-2-(1-(3-(1-(7-Fluoroquinolin-6-yl)-1-hydroxyethyl)imidazo[1,2-b]pyridazin-6-yl)ethylidene)hydrazinecarboxamide

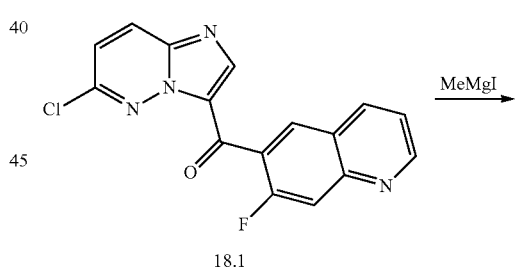

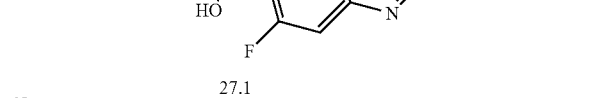

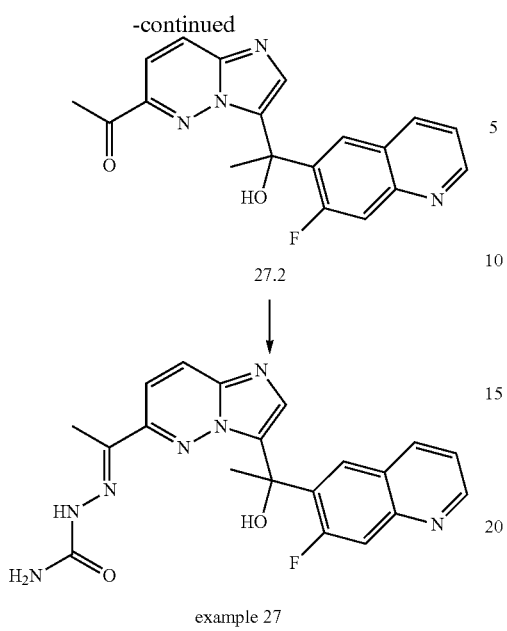

example 27

1-(6-Chloroimidazo[1,2-b]pyridazin-3-yl)-1-(7-fluoroquinolin-6-yl)ethanol (27.1)

To a solution of (6-chloroimidazo[1,2-b]pyridazin-3-yl)(7-fluoroquinolin-6-yl)methanone (2.93 g, 6.73 mmol) in THF (80 mL) was added MeMgI solution (4.48 mL, 13.45 mmol). The resulting solution was allowed to stir at reflux for 5 hrs. Then the reaction mixture was cooled to room temperature, quenched with water, washed with NH$_4$Cl solution and extracted by CH$_2$Cl$_2$. The combined organic layers were dried over Na$_2$SO$_4$ and concentrated under reduced pressure to afford 2.2 g (yield: 95%) title compound which was used to next step without further purification. LCMS (method B): [MH]$^+$=343, t$_R$=2.05 min.

1-(3-(1-(7-Fluoroquinolin-6-yl)-1-hydroxyethyl)imidazo[1,2-b]pyridazin-6-yl)ethanone (27.2)

In a flask was charged with tetrakis-(triphenylphosphine)-palladium (51 mg, 0.044 mmol) under nitrogen. A solution of 1-(6-chloroimidazo[1,2-b]pyridazin-3-yl)-1-(7-fluoroquinolin-6-yl)ethanol (150 mg, 0.44 mmol) in DMF (10 mL) was added. The system was purged with nitrogen gas three times and tributyl-(1-ethoxy-vinyl)-stannane (0.16 ml, 0.46 mmol) was added. The temperature was increased to 100° C. and stirred overnight. The reaction mixture was cooled to room temperature, 3N HCl was added and the mixture was stirred for additional 4 hrs. Water was added and the mixture was then extracted with EtOAc, dried over Na$_2$SO$_4$ and concentrated under reduced pressure. The residue was purified by column chromatography (3% to 10% MeOH in CH$_2$Cl$_2$) to afford 70 mg (yield: 41%) title compound. LCMS (method B): [MH]$^+$=351, t$_R$=2.01 min.

(E)-2-(1-(3-(1-(7-Fluoroquinolin-6-yl)-1-hydroxyethyl)imidazo[1,2-b]pyridazin-6-yl)ethylidene)hydrazinecarboxamide (Example 27)

To a solution of 1-(3-(1-(7-fluoroquinolin-6-yl)-1-hydroxyethyl)imidazo[1,2-b]pyridazin-6-yl)ethanone (35 mg, 0.09 mmol) in methanol (20 mL) was added semicarbazide hydrochloride (20 mg, 0.18 mmol). Triethyl amine was added dropwise to adjust the pH to 5-6. The reaction mixture was stirred at room temperature overnight. The solution was concentrated in reduced pressure and the residue was purified by column chromatography (3%-50% MeOH in CH$_2$Cl$_2$) to afford 23 mg (yield: 62%) title compound. $^1$H-NMR (400 MHz, DMSO-d$_6$) δ ppm 9.47 (s, 1H), 8.87 (d, 1H), 8.52 (m, 2H), 8.06 (d, 1H), 7.92 (d, 1H), 7.85 (s, 1H), 7.54 (m, 2H), 6.62 (b, 2H), 6.24 (s, 1H), 2.13 (s, 3H), 1.53 (s, 3H). LCMS (method A): [MH]$^+$=408, t$_R$=4.03 min.

Example 28

(E)-2-(1-(3-(1-Hydroxy-1-(quinolin-6-yl)ethyl)imidazo[1,2-b]pyridazin-6-yl)ethylidene)hydrazinecarboxamide

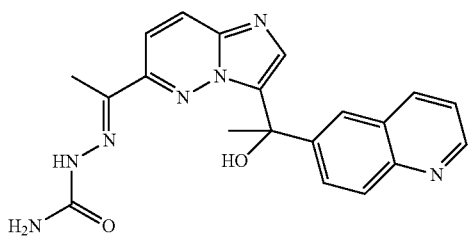 [SMILES: C/C(=N\NC(N)=O)c1ccc2ncc(C(C)(O)c3ccc4ncccc4c3)n2n1]

The title compound was prepared in analogy to the synthesis of example 27 as a yellow solid. $^1$H-NMR (400 MHz, DMSO-d$_6$) δ ppm 9.52 (s, 1H), 8.82 (d, 1H), 8.33 (d, 1H), 8.09 (m, 2H), 7.91 (m, 3H), 7.73 (d, 1H), 7.47 (q, 1H), 6.64 (b, 2H), 6.60 (s, 1H), 2.12 (s, 3H), 1.85 (s, 3H). LCMS (method B): [MH]$^+$=390, t$_R$=1.55 min.

Example 29

(E)-2-(1-(3-(1-(7-Fluoroquinolin-6-yl)ethyl)imidazo[1,2-b]pyridazin-6-yl)ethylidene)-hydrazinecarboxamide

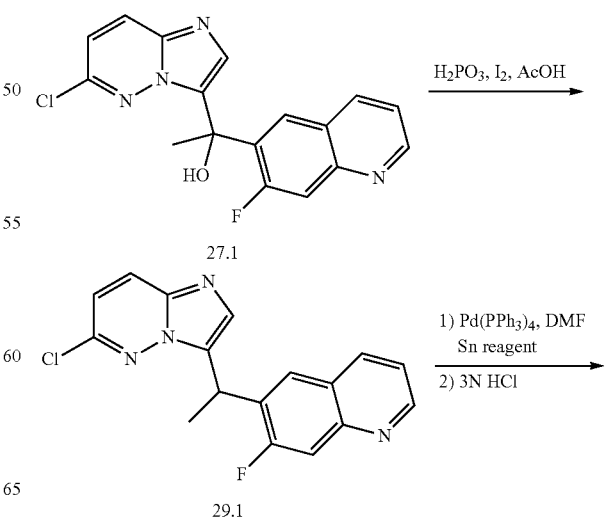

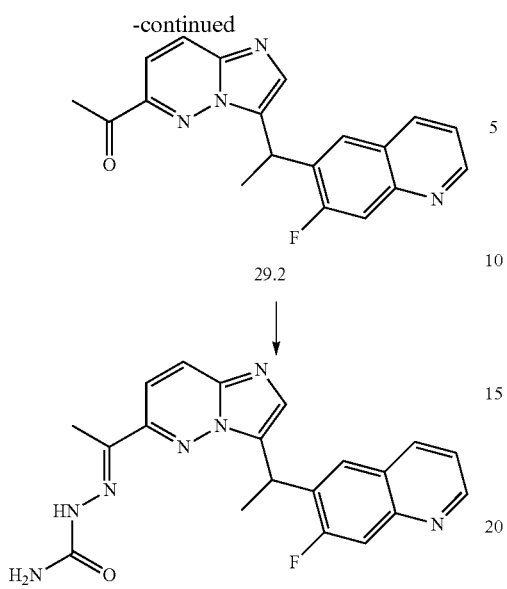

example 29

6-(1-(6-Chloroimidazo[1,2-b]pyridazin-3-yl)ethyl)-7-fluoroquinoline (29.1)

To a solution of 1-(6-chloroimidazo[1,2-b]pyridazin-3-yl)-1-(7-fluoroquinolin-6-yl)ethanol (420 mg, 1.10 mmol) in acetic acid (20 mL) was added phosphinic acid (50% aqueous solution, 0.60 ml, 5.51 mmol) and iodine (700 mg, 2.76 mmol). The resulting solution was heated at 110° C. overnight and the solvent was removed. The residue was diluted with water and pH was adjusted to 8-10 with 6N NaOH solution. The mixture was then extracted by $CH_2Cl_2$, washed with brine, dried over anhydrous $Na_2SO_4$ and concentrated in vacuo. The residue was purified by column chromatography (3% to 10% MeOH in $CH_2Cl_2$) to afford 260 mg (yield: 72%) title compound. LCMS (method B): $[MH]^+=327$, $t_R=2.52$ min.

1-(3-(1-(7-Fluoroquinolin-6-yl)ethyl)imidazo[1,2-b]pyridazin-6-yl)ethanone (29.2)

In a flask was charged with tetrakis-(triphenylphosphine)-palladium (46 mg, 0.040 mmol) under nitrogen. A solution of 6-(1-(6-chloroimidazo[1,2-b]pyridazin-3-yl)ethyl)-7-fluoroquinoline (130 mg, 0.40 mmol) in DMF (5 mL) was added. The system was purged with nitrogen gas three times and tributyl-(1-ethoxy-vinyl)-stannane (0.14 mL, 0.42 mmol) was added. The temperature was increased to 100° C. and stirred for 2 hrs. Then the reaction mixture was cooled to room temperature, 3N HCl was added and the mixture was stirred for additional 4 hrs. Water was added and the mixture was then extracted with EtOAc, dried over $Na_2SO_4$ and concentrated under reduced pressure. The residue was purified by column chromatography (3% to 10% MeOH in $CH_2Cl_2$) to afford 120 mg (yield: 90) of title compound. LCMS (method B): $[MH]^+=335$, $t_R=2.41$ min.

(E)-2-(1-(3-(1-(7-Fluoroquinolin-6-yl)ethyl)imidazo[1,2-b]pyridazin-6-yl)ethylidene)-hydrazinecarboxamide (Example 29)

To a solution of 1-(3-(1-(7-fluoroquinolin-6-yl)ethyl)imidazo[1,2-b]pyridazin-6-yl)ethanone (60 mg, 0.18 mmol) in methanol (10 ml) was added semicarbazide hydrochloride (40 mg, 0.36 mmol). Triethyl amine was added dropwise to adjust the pH to 5-6. The reaction mixture was stirred at room temperature overnight. The precipitate was collected by filtration and dried over vacuum pump to afford 38 mg (yield: 54%) title compound as a white solid. $^1$H-NMR (400 MHz, DMSO-$d_6$) δ ppm 9.62 (s, 1H), 8.84 (d, 1H), 8.26 (d, 1H), 8.15 (d, 1H), 7.96 (d, 1H), 7.77 (m, 3H), 7.44 (q, 1H), 6.69 (b, 2H), 5.03 (t, 1H), 2.07 (s, 3H), 1.83 (d, 3H). LCMS (method A): $[MH]^+=392$, $t_R=4.88$ min.

Example 30 and 30*

(E)-2-(1-(3-(1-(Quinolin-6-yl)ethyl)imidazo[1,2-b]pyridazin-6-yl)ethylidene)hydrazine-carboxamide

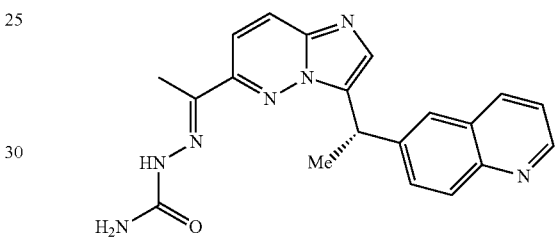

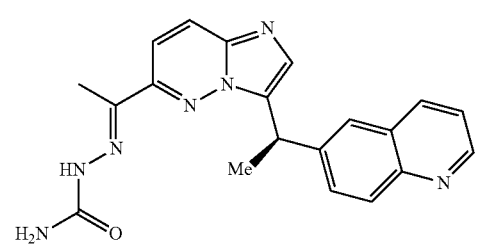

example 30 and example 30*

The title compound as a racemic mixture was prepared in analogy to the synthesis of example 29 as a white solid. $^1$H-NMR (400 MHz, DMSO-$d_6$) δ ppm 9.65 (s, 1H), 8.82 (dd, 1H), 8.27 (d, 1H), 8.15 (d, 1H), 7.93 (t, 2H), 7.88 (d, 1H), 7.80 (s, 1H), 7.74 (dd, 1H), 7.47 (q, 1H), 6.72 (b, 2H), 4.81 (q, 1H), 2.13 (s, 3H), 1.82 (d, 3H). LCMS (method A): $[MH]^+=374$, $t_R=4.37$ min. Chiral separation (method F) provided enantiomeric pure compounds example 30 and 30*.

Example 31

(E)-2-(1-(3-(1-(4,6-Difluoro-1-methyl-1H-indazol-5-yl)ethyl)imidazo[1,2-b]pyridazin-6-yl)ethylidene)hydrazinecarboxamide

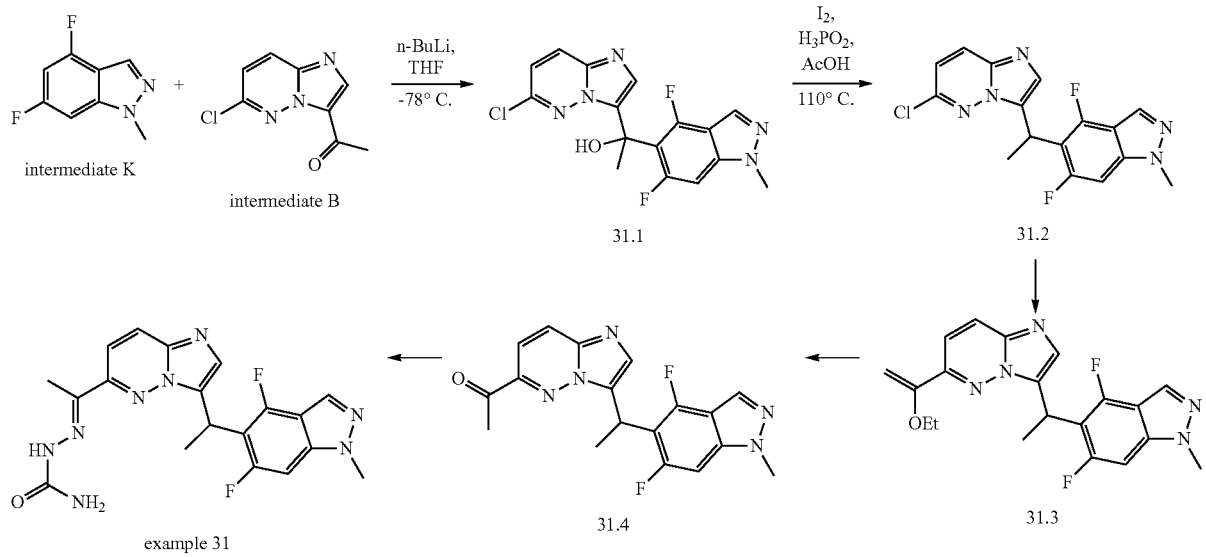

example 31

1-(6-Chloro-imidazo[1,2-b]pyridazin-3-yl)-1-(4,6-difluoro-1-methyl-1H-indazol-5-yl)-ethanol (31.1)

To a solution of 4,6-difluoro-1-methyl-1H-indazole (600 mg, 3.57 mmol) in 20 mL of anhydrous THF at −78° C. was added n-BuLi (1.6M solution in hexane, 2.56 mL, 4.1 mmol). The solution was stirred at this temperature for 1 hour and then a solution of 1-(6-Chloro-imidazo[1,2-b]pyridazin-3-yl)-ethanone (698 mg, 3.57 mmol) in 10 mL of anhydrous THF was added at −78° C. dropwise. The resulting solution was stirred at this temperature for 3 hours and slowly warmed up to room temperature and stirred overnight. The reaction mixture was quenched with water, extracted with EtOAc for three times. The organic layers were combined and washed with brine, dried over Na$_2$SO$_4$. The crude product was purified with flash chromatography (CH$_2$Cl$_2$:MeOH 95:5) to give the title compound as a yellow oil (530 mg, 41%). $^1$H-NMR (400 MHz, CDCl$_3$) δ ppm 8.05 (d, 1H), 8.0 (s, 1H), 7.85 (s, 1H), 7.1 (d, 1H), 6.85 (d, 1H), 4.0 (s, 3H), 2.3 (s, 3H). LCMS (method B): [MH]$^+$=363.9, $t_R$=2.15 min.

6-Chloro-3-[1-(4,6-difluoro-1-methyl-1H-indazol-5-yl)-ethyl]-imidazo[1,2-b]pyridazine (31.2)

A solution of 1-(6-chloro-imidazo[1,2-b]pyridazin-3-yl)-1-(4,6-difluoro-1-methyl-1H-indazol-5-yl)-ethanol (530 mg, 1.457 mmol), Iodine (925 mg, 3.64 mmol) and phosphinic acid (50%, 0.556 mL) in 20 mL acetic acid was heated at 110° C. for 2 hours. Solvent was evaporated and the residue was dissolved in water, neutralized with sat. NaHCO$_3$ solution and extracted with CH$_2$Cl$_2$ for three times. Organic layers were combined and washed with brine, dried over Na$_2$SO$_4$. Solvent was then evaporated and the crude was purified on flash chromatography (Hexane:EtOAc 1:2) to give the title compound as a light yellow solid (320 mg, 63.2%). $^1$H-NMR (400 MHz, MeOH-d$_4$) δ ppm 8.03 (s, 1H), 8.0 (d, 1H), 7.8 (s, 1H), 7.23 (d, 1H), 7.19 (d, 1H), 5.1 (q, 1H), 4.0 (s, 3H), 1.92 (d, 3H). LCMS (method B): [MH]$^+$=347.9, $t_R$=2.69 min.

3-[1-(4,6-Difluoro-1-methyl-1H-indazol-5-yl)-ethyl]-6-(1-ethoxy-vinyl)-imidazo[1,2-b]pyridazine (31.3)

A solution of 6-chloro-3-[1-(4,6-difluoro-1-methyl-1H-indazol-5-yl)-ethyl]-imidazo[1,2-b]pyridazine (80 mg, 0.23 mmol) and tributyl(1-ethoxyvinyl)stannane (0.234 mL, 0.69 mmol) in 15 mL DMF was purged with N$_2$ for 30 min and then tetrakis-(triphenylphosphine)-palladium (80 mg, 0.069 mmol) was added, and the solution was heated at 95° C. for overnight. Then the reaction was quenched with water, extracted with EtOAc for three times. The organic layers were combined, washed with KF solution and brine, dried over Na$_2$SO$_4$. Solvent was evaporated and the crude product (80 mg, 90%) was used in the next step without further purification. LCMS (method C): [MH]$^+$=384.0, $t_R$=4.67 min 1-(3-(1-(4,6-Difluoro-1-methyl-1H-indazol-5-yl)ethyl)imidazo[1,2-b]pyridazin-6-yl)ethanone (31.4)

2 mL of 3N HCl solution was added to a solution of 3-[1-(4,6-Difluoro-1-methyl-1H-indazol-5-yl)-ethyl]-6-(1-ethoxy-vinyl)-imidazo[1,2-b]pyridazine in 10 ml MeOH. The reaction solution was stirred at room temperature for 3 hours and then neutralized with sat. NaHCO$_3$ solution. Solvent was evaporated and the residue was purified on chromatography (CH$_2$Cl$_2$:MeOH 10:1) to give the title compound as a yellow solid (30 mg, 41%). LCMS (method C): [MH]$^+$= 355.9, $t_R$=3.75 min (E)-2-(1-(3-(1-(4,6-Difluoro-1-methyl-1H-imidazol-5-yl)ethyl)imidazo[1,2-b]pyridazin-6-yl)ethylidene)hydrazinecarboxamide (Example 31)

A solution of 1-(3-(1-(4,6-difluoro-1-methyl-1H-indazol-5-yl)ethyl)imidazo[1,2-b]pyridazin-6-yl)ethanone (22 mg, 0.062 mmol) and hydrazinecarboxamide hydrochloride (16 mg, 0.14 mmol) in 8 mL MeOH was stirred at room temperature for overnight. The solution was then neutralized with sat. NaHCO$_3$ solution, extracted with EtOAc. Organic layers were combined and washed with brine, dried over Na$_2$SO$_4$. Solvent was evaporated and the crude product was purified on HPLC (basic with 0.05% NH$_4$OH) to give the title compound as a white solid (10 mg, 35%). $^1$H-NMR (400 MHz, MeOH-d$_4$) δ ppm 8.10 (d, 1H), 8.02 (s, 1H), 7.89 (d, 1H), 7.79 (m, 1H), 7.15 (d, 1H), 5.15 (q, 1H), 3.99 (s, 3H), 2.18 (s, 3H), 1.96 (d, 3H). LCMS (method B): [MH]$^+$=413.0, t$_R$=2.41 min.

Example 32

(E)-2-(1-(3-((4,6-Difluoro-1-methyl-1H-indazol-5-yl)methyl)imidazo[1,2-b]pyridazin-6-yl)ethylidene)hydrazinecarboxamide 1-(3-((4,6-Difluoro-1-methyl-1H-indazol-5-yl)methyl)imidazo[1,2-b]pyridazin-6-yl)ethanone (32.3)

The title compound as a light yellow solid (350 mg, 0.769 mmol, 71.3%) was synthesized from 6-chloro-3-((4,6-difluoro-1-methyl-1H-indazol-5-yl)methyl)imidazo[1,2-b]pyridazine (360 mg, 1.079 mmol), tributyl(1-ethoxyvinyl)stannane (1.095 ml, 3.24 mmol) and tetrakis-(triphenylphosphine)-palladium (374 mg, 0.324 mmol) using the same procedure as described in the synthesis of compound 31.4. $^1$H-NMR (400 MHz, MeOH-d$_4$) δ ppm 8.09 (s, 1H), 8.07 (s, 1H), 7.78 (d, 1H), 7.71 (s, 1H), 7.26 (d, 1H), 4.59 (s, 2H), 4.02 (s, 3H), 2.74 (s, 3H). LCMS (method B): [MH]$^+$= 342.0, t$_R$=2.39 min.

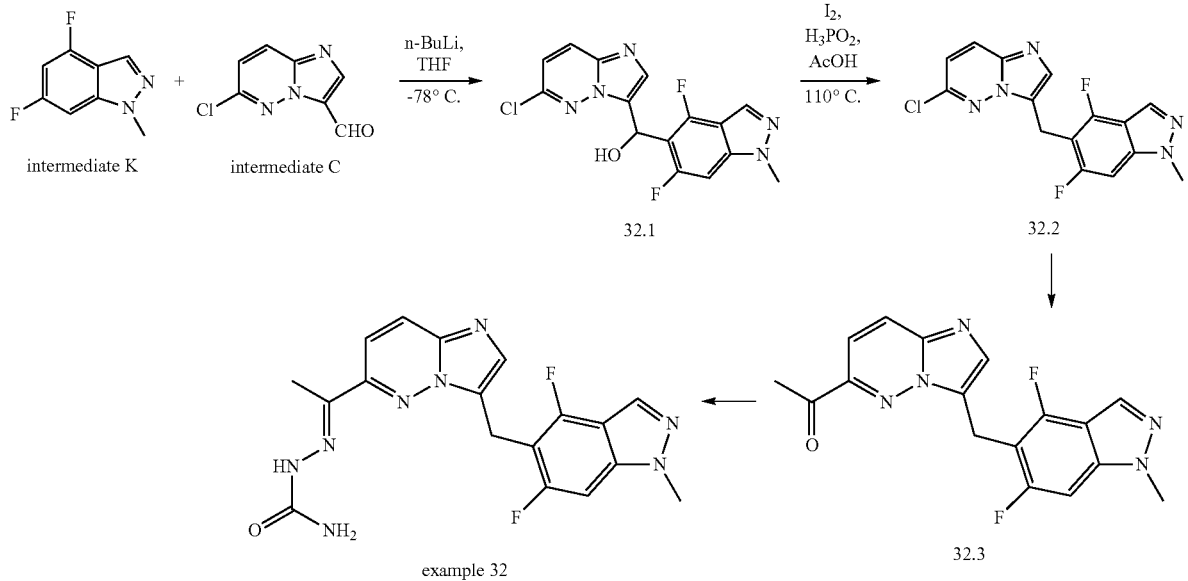

example 32

(6-Chloroimidazo[1,2-b]pyridazin-3-yl)(4,6-difluoro-1-methyl-1H-indazol-5-yl)methanol (32.1)

The title compound as a yellow solid (60 mg, 0.172 mmol, 41%) was synthesized from intermediate 4,6-Difluoro-1-methyl-1H-indazole (70 mg, 0.416 mmol) and 6-chloroimidazo[1,2-b]pyridazine-3-carbaldehyde (76 mg, 0.416 mmol) using the same procedure as described in the synthesis of compound 31.1. $^1$H-NMR (400 MHz, MeOH-d$_4$) δ ppm 8.08 (s, 1H), 8.03 (d, 1H), 7.85 (s, 1H), 7.26 (q, 2H), 6.76 (s, 1H), 4.03 (s, 3H). LCMS (method B): [MH]$^+$=349.9, t$_R$=2.12 min.

6-Chloro-3-((4,6-difluoro-1-methyl-1H-indazol-5-yl)methyl)imidazo[1,2-b]pyridazine (32.2)

The title compound as a light yellow solid (370 mg, 1.109 mmol, 78%) was synthesized from (6-chloroimidazo[1,2-b]pyridazin-3-yl)(4,6-difluoro-1-methyl-1H-indazol-5-yl)methanol (500 mg, 1.43 mmol), Iodine (907 mg, 3.57 mmol) and phosphinic acid (50%, 0.55 mL) using the same procedure as described in the synthesis of compound 31.2. $^1$H-NMR (400 MHz, MeOH-d$_4$) δ ppm 8.07 (s, 1H), 8.01 (d, 1H), 7.44 (s, 1H), 7.29 (d, 1H), 7.27 (d, 1H), 4.46 (s, 2H), 4.04 (s, 3H). LCMS (method B): [MH]$^+$=333.9, t$_R$=2.68 min.

(E)-2-(1-(3-((4,6-Difluoro-1-methyl-1H-indazol-5-yl)methyl)imidazo[1,2-b]pyridazin-6-yl)ethylidene)hydrazinecarboxamide (Example 32)

A solution of 1-(3-((4,6-difluoro-1-methyl-1H-indazol-5-yl)methyl)imidazo[1,2-b]pyridazin-6-yl)ethanone (45 mg, 0.099 mmol, 75% pure) and hydrazinecarboxamide hydrochloride (22 mg, 0.198 mmol) in 10 mL MeOH was stirred at room temperature overnight. Solvent was evaporated and the residue was dissolved in a small amount of MeOH. Precipitates formed and was filtered to give the title compound as a white solid (25 mg, 0.062 mmol). $^1$H-NMR (400 MHz, DMSO-d$_6$) δ ppm 9.95 (s, 1H), 8.62 (d, 1H), 8.20 (s, 1H), 8.17 (s, 1H), 8.0 (s, 1H), 7.54 (d, 1H), 6.85 (broad, 2H), 4.48 (s, 2H), 4.0 (s, 3H), 2.3 (s, 3H). LCMS (method B): [MH]$^+$= 398.9, t$_R$=2.17 min.

Example 33

(E)-2-(1-(3-(Difluoro(quinolin-6-yl)methyl)-[1,2,4]triazolo[4,3-b]pyridazin-6-yl)ethylidene)-hydrazinecarboxamide

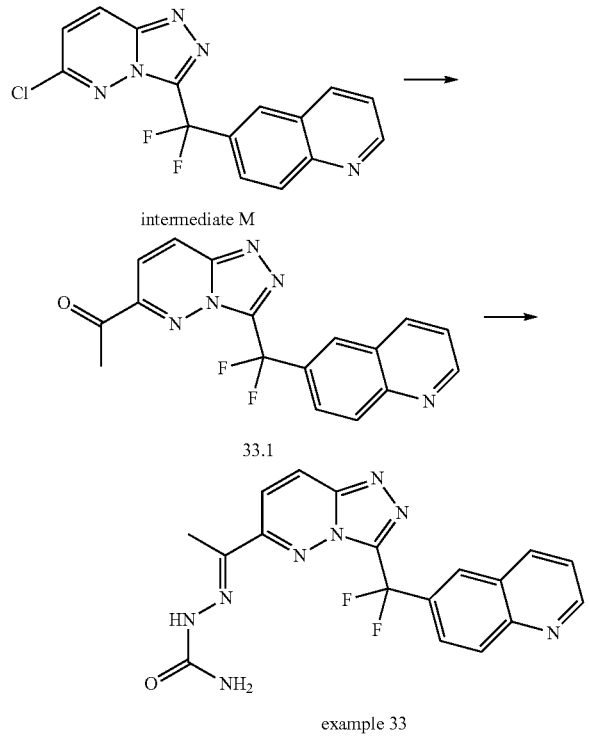

intermediate M 33.1 example 33

1-(3-(Difluoro(quinolin-6-yl)methyl)-[1,2,4]triazolo[4,3-b]pyridazin-6-yl)ethanone (33.1)

The title compound as a light yellow oil (180 mg, 30%, 80% pure) was synthesized from 6-((6-chloro-[1,2,4]triazolo[4,3-b]pyridazin-3-yl)difluoromethyl)quinoline (500 mg, 1.507 mmol), tributyl(1-ethoxyvinyl)stannane (2.55 ml, 7.54 mmol) and $PdCl_2(PPh_3)_2$ (106 mg, 0.151 mmol) in 1,4-dioxane using the same procedure as described in the synthesis of compound 31.4. $^1$H-NMR (400 MHz, MeOH-$d_4$) δ ppm 9.17 (s, 1H), 8.91 (d, 1H), 8.65 (s, 1H), 8.43 (d, 1H), 8.28 (q, 2H), 7.96 (d, 1H), 7.92 (m, 1H), 2.61 (s, 3H). LCMS (method B): $[MH]^+=340.1$, $t_R=2.16$ min.

(E)-2-(1-(3-(Difluoro(quinolin-6-yl)methyl)-[1,2,4]triazolo[4,3-b]pyridazin-6-yl)ethylidene)-hydrazinecarboxamide (Example 33)

A solution of 1-(3-(difluoro(quinolin-6-yl)methyl)-[1,2,4]triazolo[4,3-b]pyridazin-6-yl)ethanone (100 mg, 0.295 mmol) and hydrazinecarboxamide hydrochloride (44.3 mg, 0.589 mmol) in MeOH was stirred at room temperature for overnight. Solvent was evaporated and the residue was dissolved in a small amount of MeOH. Solid was filtered and dried to give the title compound as a white solid (90 mg, 75%). $^1$H-NMR (400 MHz, DMSO-$d_6$) δ ppm 9.90 (s, 1H), 9.06 (d, 1H), 8.62 (d, 1H), 8.49 (m, 2H), 8.34 (d, 1H), 8.20 (d, 1H), 8.03 (d, 1H), 7.70 (m, 1H), 6.82 (broad, 2H), 2.07 (s, 3H). LCMS (method B): $[MH]^+=397.1$, $t_R=2.08$ min.

Example 34

(E)-1-(1-(3-(Difluoro(quinolin-6-yl)methyl)-[1,2,4]triazolo[4,3-b]pyridazin-6-yl)ethylideneamino)imidazolidine-2,4-dione

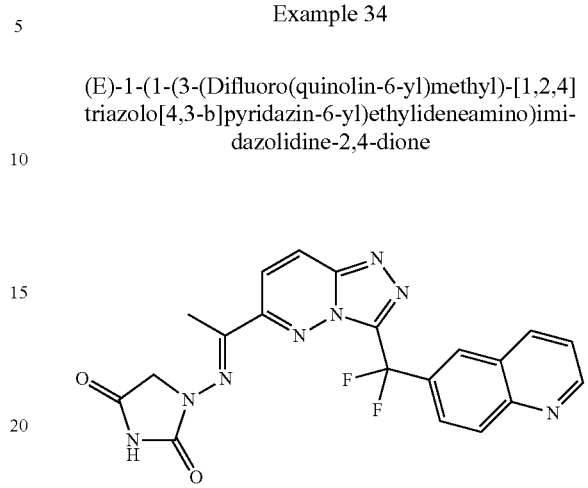

A solution of 1-(3-(difluoro(quinolin-6-yl)methyl)-[1,2,4]triazolo[4,3-b]pyridazin-6-yl)ethanone (20 mg, 0.059 mmol) and 1-aminoimidazolidine-2,4-dione (13.6 mg, 0.12 mmol) was stirred in MeOH at room temperature over a weekend. Light yellow solid was filtered to give the title compound (6 mg, 0.014 mmol). The filtrate was purified on HPLC (acidic with 0.05% TFA) to give the title compound as TFA salt (8 mg, 0.0145 mmol). The combined yield was 48%. $^1$H-NMR (400 MHz, DMSO-$d_6$) δ ppm 11.46 (s, 1H), 9.02 (d, 1H), 8.55 (d, 1H), 8.48 (s, 1H), 8.46 (s, 1H), 8.18 (d, 1H), 8.0 (s, 1H), 7.98 (s, 1H), 7.65 (d, 1H), 4.54 (s, 2H), 2.24 (s, 3H). LCMS (method B): $[MH]^+=437.1$, $t_R=2.06$ min.

Example 35

(E)-1-(1-(3-(Difluoro(quinolin-6-yl)methyl)-[1,2,4]triazolo[4,3-b]pyridazin-6-yl)ethylideneamino)imidazolidin-2-one

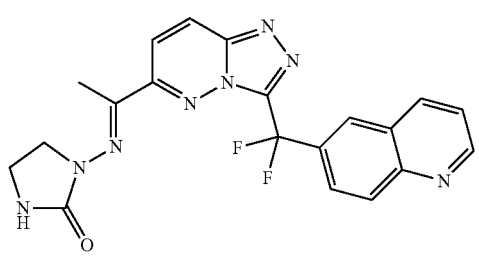 [SMILES: C/C(=N\N1CCNC1=O)c1ccc2nnc(C(F)(F)c3ccc4ncccc4c3)n2n1]

A solution of 1-(3-(difluoro(quinolin-6-yl)methyl)-[1,2,4]triazolo[4,3-b]pyridazin-6-yl)ethanone (20 mg, 0.059 mmol) and 1-aminoimidazolidin-2-one (12 mg, 0.12 mmol) in MeOH was stirred at room temperature for overnight. Solvent was evaporated and the crude product was purified on flash chromatography ($CH_2Cl_2$:MeOH 9:1) to give the title compound as a white solid (8 mg, 32%). $^1$H-NMR (400 MHz, MeOH-$d_4$) δ ppm 8.98 (s, 1H), 8.52 (d, 1H), 8.43 (s, 1H), 8.26

(d, 2H), 8.19 (m, 1H), 8.06 (d, 1H), 7.66 (d, 1H), 3.55 (t, 2H), 3.38 (t, 2H), 2.30 (s, 3H). LCMS (method A): [MH]⁺=423.0, $t_R$=4.63 min.

Example 36

(E)-N'-(1-(3-(Difluoro(quinolin-6-yl)methyl)-[1,2,4]triazolo[4,3-b]pyridazin-6-yl)ethylidene)-2-morpholinoacetohydrazide

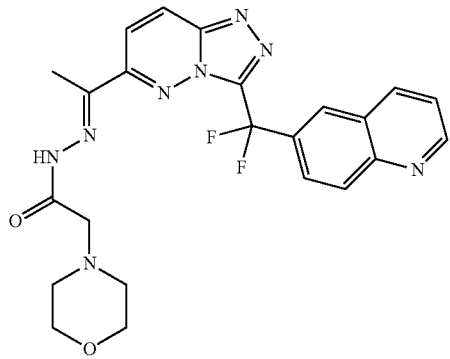 [SMILES: C/C(=N\NC(=O)CN1CCOCC1)c1ccc2nnc(C(F)(F)c3ccc4ncccc4c3)n2n1]

1-(3-(difluoro(quinolin-6-yl)methyl)[1,2,4]triazolo[4,3-b]pyridazin-6-yl)ethanone (25 mg, 0.074 mmol) and 2-morpholinoacetohydrazide (12 mg, 0.075 mmol) were dissolved in MeOH and the pH of the reaction solution was adjusted to 5. The solution was then stirred at 45° C. for 3 hours. Solvent was evaporated and the crude product was purified on HPLC (neutralized to free base) to give the title compound as a white solid (18 mg, 50%). ¹H-NMR (400 MHz, DMSO-d₆) δ ppm 9.02 (s, 1H), 8.55 (d, 1H), 8.43 (d, 2H), 8.17 (d, 1H), 8.01 (m, 2H), 7.65 (d, 1H), 3.59 (m, 4H), 2.13 (m, 4H). LCMS (method B): [MH]⁺=481.1, $t_R$=1.66 min.

Example 37

(E)-2-(1-(3-(Quinolin-6-ylmethyl)-[1,2,4]triazolo[4,3-b]pyridazin-6-yl)ethylidene)-hydrazinecarboxamide (37)

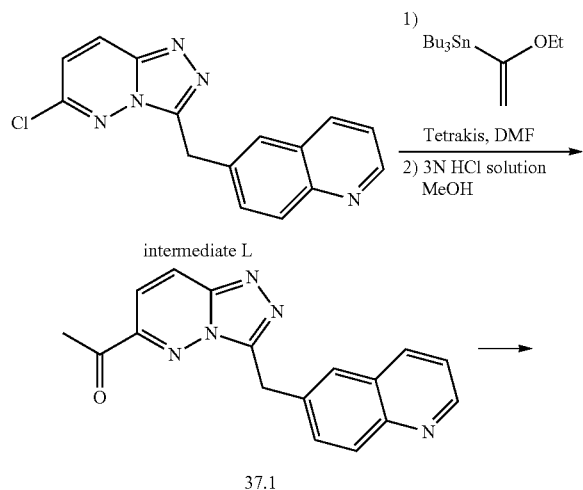

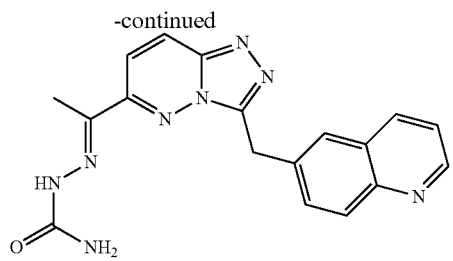

example 37

1-(3-(Quinolin-6-ylmethyl)-[1,2,4]triazolo[4,3-b]pyridazin-6-yl)ethanone (37.1)

The title compound as a light yellow solid (500 mg, 51%) was synthesized from 6-((6-chloro-[1,2,4]triazolo[4,3-b]pyridazin-3-yl)methyl)quinoline (950 mg, 3.21 mmol), tributyl (1-ethoxy-vinyl)stannane (1.142 ml, 3.37 mmol) and tetrakis-(triphenylphosphine)-palladium (186 mg, 0.161 mmol) in DMF using the same procedure as described in the synthesis of compound 31.4. LCMS (method B): [MH]⁺=304.1, $t_R$=1.71 min.

(E)-2-(1-(3-(Quinolin-6-ylmethyl)-[1,2,4]-triazolo[4,3-b]pyridazin-6-yl)ethylidene)-hydrazinecarboxamide (Example 37)

A solution of 1-(3-(quinolin-6-ylmethyl)-[1,2,4]triazolo[4,3-b]pyridazin-6-yl)ethanone (35 mg, 0.115 mmol) and hydrazinecarboxamide hydrochloride (17.32 mg, 0.231 mmol) in MeOH was stirred at room temperature for overnight. Solid was filtered and dried to provide the title compound as a light yellow solid (35 mg, 84%). ¹H-NMR (400 MHz, DMSO-d₆) δ ppm 9.90 (s, 1H), 9.10 (d, 1H), 8.79 (d, 1H), 8.37 (d, 1H), 8.17 (m, 3H), 8.03 (d, 1H), 7.83 (m, 1H), 6.85 (broad, 2H), 4.84 (s, 2H), 2.24 (s, 3H). LCMS (method A): [MH]⁺=361.1, $t_R$=3.58 min.

Example 38

(E)-1-(1-(3-(Quinolin-6-ylmethyl)-[1,2,4]-triazolo[4,3-b]pyridazin-6-yl)ethylideneamino)-imidazolidine-2,4-dione

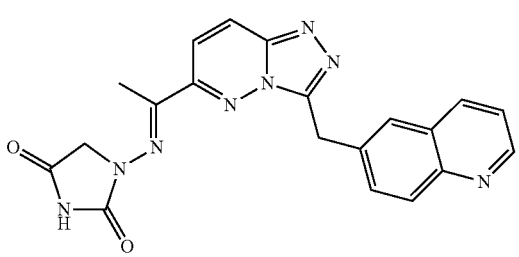 [SMILES: C/C(=N\N1CC(=O)NC1=O)c1ccc2nnc(Cc3ccc4ncccc4c3)n2n1]

The title compound (20 mg, 51%) was synthesized from 1-(3-(quinolin-6-ylmethyl)-[1,2,4]triazolo[4,3-b]pyridazin-6-yl)ethanone (30 mg, 0.1 mmol) and 1-aminoimidazolidine-2,4-dione (22.77 mg, 0.198 mmol) using the same procedure as described in the synthesis of example 37. ¹H-NMR (400 MHz, DMSO-d₆) δ ppm 11.44 (s, 1H), 9.05 (d, 1H), 8.70 (d, 1H), 8.32 (d, 1H), 8.12 (d, 2H), 7.98 (d, 1H), 7.87 (d, 1H), 7.77 (m, 1H), 4.83 (s, 2H), 4.54 (s, 2H), 2.40 (s, 3H). LCMS (method B): [MH]⁺=401.1, $t_R$=1.64 min.

Example 39

(E)-1-Methyl-2-(1-(3-(quinolin-6-ylmethyl)-[1,2,4]-triazolo[4,3-b]pyridazin-6-yl)ethylidene)hydrazinecarboxamide

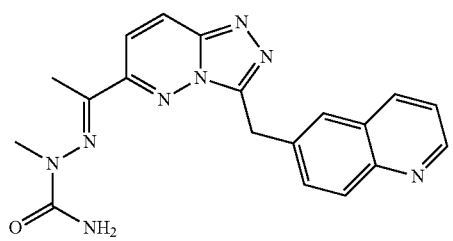 [SMILES: C/C(=N\N(C)C(N)=O)c1ccc2nnc(Cc3ccc4ncccc4c3)n2n1]

The title compound (27 mg, 55%) was synthesized from 1-(3-(quinolin-6-ylmethyl)-[1,2,4]triazolo[4,3-b]pyridazin-6-yl)ethanone (40 mg, 0.132 mmol) and 1-methylhydrazinecarboxamide (23.5 mg, 0.264 mmol) using the same procedure as described in the synthesis of 37. $^1$H-NMR (400 MHz, DMSO-$d_6$) δ ppm 9.06 (d, 1H), 8.73 (d, 1H), 8.17 (m, 4H), 8.00 (d, 1H), 7.79 (m, 1H), 6.69 (s, 2H), 4.82 (s, 2H), 3.27 (s, 3H), 2.32 (s, 3H). LCMS (method A): [MH]$^+$=375.0, $t_R$=3.79 min.

Example 40

(E)-2-(1-(3-((5,7-Difluoroquinolin-6-yl)methyl)-[1,2,4]triazolo[4,3-b]pyridazin-6-yl)ethylidene)hydrazinecarboxamide

(5,7-Difluoro-quinolin-6-yl)-acetic acid hydrazide (40.1)

To a solution of (5,7-difluoro-quinolin-6-yl)-acetic acid methyl ester (1.023 g, 4.32 mmol) in ethanol (15 mL) was added hydrazine monohydrate (2 mL) and the mixture was stirred at 30° C. for 24 h. The solvent was removed in vacuo to afford 1.024 g of the title compound as white solid, which was used without further purification. $^1$H-NMR (400 MHz, DMSO-$d_6$) δ ppm 9.33 (s, 1H), 8.97 (d, 1H), 8.46 (d, 1H), 7.67 (d, 1H), 7.61 (dd, 1H), 4.27 (s, 2H). LCMS (method B): [MH]$^+$=238, $t_R$=3.24 min. (5,7-difluoroquinolin-6-yl)-acetic acid methyl ester was synthesized using the method described in WO2008/144767 p 108 (intermediate 2), followed by the method described for Intermediate 12, step 1 WO2008/144767 p 114.

6-(6-Chloro-[1,2,4]triazolo[4,3-b]pyridazin-3-ylmethyl)-5,7-difluoro-quinoline (40.2)

A solution of (5,7-difluoro-quinolin-6-yl)-acetic acid hydrazide (1.024 g, 4.32 mmol) and 3,6-dichloropyridazine (0.772 g, 5.18 mmol) in 60 mL of butan-1-ol was heated at 135° C. in a sealed tube for 16 h. The solvent was removed in vacuo, and the residue was purified by flash chromatography to afford 842 mg of the title compound as gray solid. $^1$H-NMR (400 MHz, DMSO-$d_6$) δ ppm 8.96 (dd, 1H), 8.26 (d, 1H), 7.60-7.66 (m, 2H), 7.45 (d, 1H), 4.81 (s, 2H). LCMS (method B): [MH]$^+$=332, $t_R$=4.88 min.

6-[6-(1-Ethoxy-vinyl)-[1,2,4]triazolo[4,3-b]pyridazin-3-ylmethyl]-5,7-difluoro-quinoline (40.3)

A solution of 6-(6-chloro-[1,2,4]triazolo[4,3-b]pyridazin-3-ylmethyl)-5,7-difluoro-quinoline (58 mg, 0.175 mmol) in

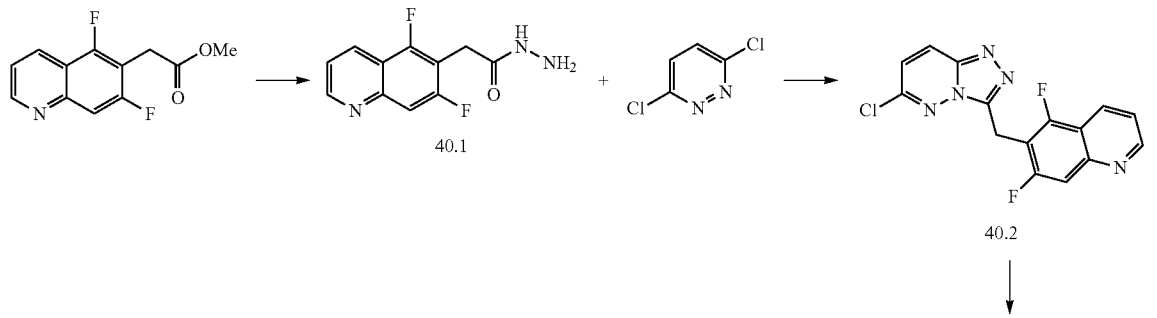

40.1

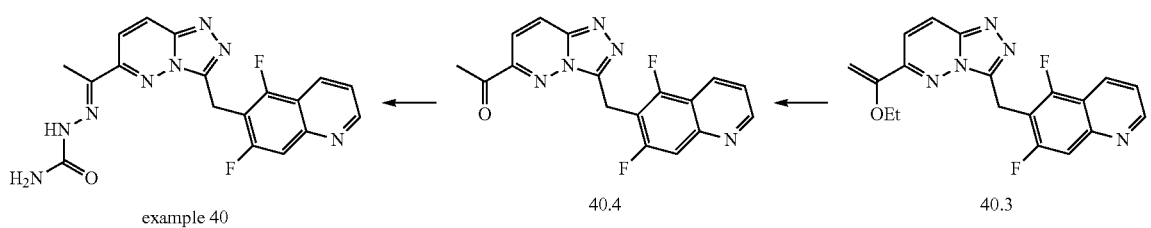

example 40   40.4   40.3 dioxane (5 mL) was purged with argon for 1 min. Tributyl-(1-ethoxy-vinyl)stannane (0.2 mL, 0.53 mmol) was then added, followed by addition of PdCl$_2$(PPh$_3$)$_2$ (14.4 mg, 0.021 mmol). The reaction mixture was purged with argon for another half min. The reaction mixture was stirred at 80-85° C. for 4 h; LC/MS showed the reaction was complete. The reaction mixture was diluted with EtOAc, and 15 mL of aqueous KF solution was added. The mixture was extracted with EtOAc, dried over anhydrous Na$_2$SO$_4$, concentrated to give the crude title compound, which was used without further purification. LCMS (method A): [MH]$^+$=368, t$_R$=5.39 min.

1-[3-(5,7-Difluoro-quinolin-6-ylmethyl)-[1,2,4]-triazolo[4,3-b]pyridazin-6-yl]ethanone (40.4)

Aqueous 3N HCl (0.2 mL, 0.6 mmol) was added to a solution of 6-[6-(1-ethoxy-vinyl)-[1,2,4]triazolo[4,3-b]pyridazin-3-ylmethyl]-5,7-difluoro-quinoline (87 mg, 0.237 mmol) in HOAc (2 mL). The reaction mixture was stirred at 40° C. for 6 h. LC/MS showed reaction was complete. The solvent was removed in vacuo, and the residue dissolved in EtOAc was neutralized, and extracted with EtOAc. The organic layer was dried, concentrated and purified by flash chromatography to afford 40 mg of the title compound as pale yellow solid. $^1$H-NMR (400 MHz, MeOH-d$_4$) δ ppm 8.95 (dd, 1H), 8.56 (d, 1H), 8.29 (d, 1H), 7.85 (d, 1H), 7.60-7.67 (m, 2H), 4.94 (s, 2H), 2.67 (s, 3H). LCMS (method A): [MH]$^+$=339, t$_R$=4.88 min.

(E)-2-(1-(3-((5,7-Difluoroquinolin-6-yl)methyl)-[1,2,4]triazolo[4,3-b]pyridazin-6-yl)ethylidene)hydrazinecarboxamide (Example 40)

A mixture of 1-[3-(5,7-difluoro-quinolin-6-ylmethyl)-[1,2,4]triazolo[4,3-b]pyridazin-6-yl]-ethanone (38 mg, 0.112 mmol), semicarbazide (37.5 mg, 0.336 mmol) and sodium bicarbonate (40 mg, 0.67 mmol) in methanol (3 mL) was stirred at 40° C. for 20 h. LC/MS showed the reaction was complete, and the suspension was filtered. The filtrate cake was washed successively with cold water and methanol, and then dried to afford 36.3 mg (82% yield) of the title compound as white solid. $^1$H-NMR (400 MHz, DMSO-d$_6$) δ ppm 9.85 (s, 1H), 8.99 (dd, 1H), 8.49 (d, 1H), 8.35 (d, 1H), 8.18 (d, 1H), 7.73 (d, 1H), 7.62 (dd, 1H), 6.82 (s br, 2H), 4.75 (s, 2H), 2.19 (s, 3H). LCMS (method A): [MH]$^+$=397, t$_R$=4.43 min.

Example 41

(E)-2-(1-(3-((5,7-Difluoroquinolin-6-yl)methyl)-[1,2,4]triazolo[4,3-b]pyridazin-6-yl)ethylidene)-N,1-dimethylhydrazinecarboxamide

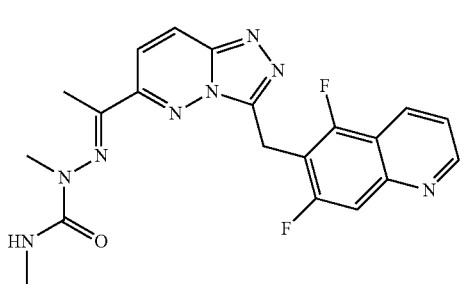 [SMILES: CNC(=O)N(C)/N=C(\C)c1ccc2nnc(Cc3c(F)cc4ncccc4c3F)n2n1]

The title compound was prepared using the same procedure as described in the synthesis of example 40. $^1$H-NMR (400 MHz, DMSO-d$_6$) δ ppm 8.99 (d, 1H), 8.49 (d, 1H), 8.27 (d, 1H), 8.19 (d, 1H), 7.74 (d, 1H), 7.62 (dd, 1H), 7.03-7.05 (m, 1H), 4.78 (s, 2H), 3.26 (s, 3H), 2.70 (d, 3H), 2.34 (s, 3H). LCMS (method A): [MH]$^+$=425, t$_R$=4.74 min.

Example 42

(E)-2-(1-(3-((5,7-Difluoroquinolin-6-yl)methyl)-[1,2,4]triazolo[4,3-b]pyridazin-6-yl)ethylidene)-1-methylhydrazinecarboxamide

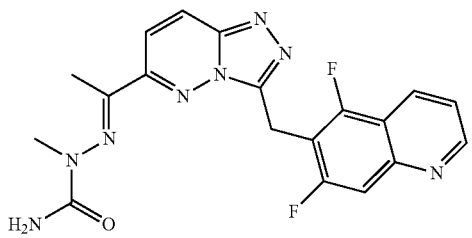

The title compound was prepared using the same procedure as described in the synthesis of example 40. $^1$H-NMR (400 MHz, DMSO-d$_6$) δ ppm 9.00 (dd, 1H), 8.50 (d, 1H), 8.17-8.25 (m, 2H), 7.75 (d, 1H), 7.64 (dd, 1H), 6.70 (s, 2H), 4.79 (s, 2H), 3.27 (s, 3H), 2.35 (s, 3H). LCMS (method A): [MH]$^+$=411, t$_R$=4.60 min.

Example 43

(E)-2-(1-(3-((5,7-Difluoroquinolin-6-yl)methyl)-[1,2,4]triazolo[4,3-b]pyridazin-6-yl)ethylidene)-1-ethylhydrazinecarboxamide

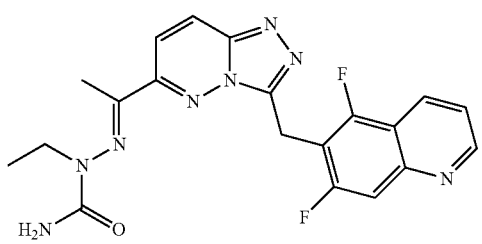 [SMILES: CCN(/N=C(\C)c1ccc2nnc(Cc3c(F)cc4ncccc4c3F)n2n1)C(N)=O]

The title compound was prepared using the same procedure as described in the synthesis of example 40. $^1$H-NMR (400 MHz, CDCl$_3$) δ ppm 8.95 (dd, 1H), 8.38 (dd, 1H), 8.05 (d, 1H), 7.86 (d, 1H), 7.64 (d, 1H), 7.44 (dd, 1H), 5.42 (s br, 2H), 4.84 (s, 2H), 3.95 (q, 2H), 2.46 (s, 3H), 1.18 (t, 3H). LCMS (method A): [MH]⁺=425, $t_R$=4.75 min.

Example 44

(E)-3-(1-(3-((5,7-Difluoroquinolin-6-yl)methyl)-[1,2,4]triazolo[4,3-b]pyridazin-6-yl)ethylideneamino)oxazolidin-2-one

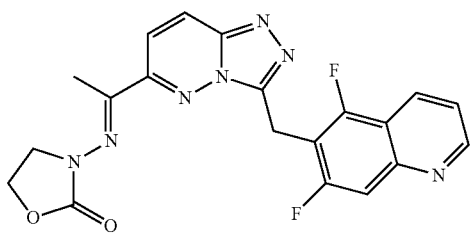 [SMILES: C/C(=N\N1CCOC1=O)c1ccc2nnc(Cc3c(F)cc4ncccc4c3F)n2n1]

The title compound was prepared from 3-aminooxazolidin-2-one and 1-(3-((5,7-difluoroquinolin-6-yl)methyl)-[1,2,4]triazolo[4,3-b]pyridazin-6-yl)ethanone in 86% yield as white solid using the same procedure as described in the synthesis of example 40. ¹H-NMR (400 MHz, DMSO-d₆) δ ppm 9.00 (d, 1H), 8.50 (d, 1H), 8.33 (d, 1H); 7.87 (d, 1H), 7.75 (d, 1H), 7.63 (dd, 1H), 4.81 (s, 2H), 4.49 (t, 2H), 4.05 (t, 2H), 2.33 (s, 3H). LCMS (method A): [MH]⁺=424, $t_R$=4.54 min.

Example 45

(E)-2-(1-(3-((7-Fluoroquinolin-6-yl)methyl)-[1,2,4]-triazolo[4,3-b]pyridazin-6-yl)ethylidene)hydrazinecarboxamide 6-(6-Chloro-[1,2,4]triazolo[4,3-b]pyridazin-3-ylmethyl)-7-fluoro-quinoline (45.1)

The title compound was prepared using the same procedure as described in the synthesis of 40.2. ¹H-NMR (400 MHz, MeOH-d₄) δ ppm 8.85 (d, 1H), 8.33 (d, 1H), 8.26 (d, 1H), 7.96 (d, 1H), 7.72 (d, 1H), 7.51 (dd, 1H), 7.43 (d, 1H), 4.79 (s, 2H). LCMS (method A): [MH]⁺=314, $t_R$=4.61 min.

6-[6-(1-Ethoxy-vinyl)-[1,2,4]-triazolo[4,3-b]pyridazin-3-ylmethyl]-7-fluoro-quinoline (45.2)

The title compound was prepared using the same procedure as described in the synthesis of 40.3. LCMS (method B): [MH]⁺=350, $t_R$=2.40 min.

1-[3-(7-Fluoro-quinolin-6-ylmethyl)-[1,2,4]-triazolo[4,3-b]pyridazin-6-yl]-ethanone (45.3)

The title compound was prepared using the same procedure as described in the synthesis of 40.4. ¹H-NMR (400 MHz, CDCl₃) δ ppm 8.90 (dd, 1H), 8.18 (d, 1H), 8.05-8.13 (m, 1H), 7.75-7.87 (m, 3H), 7.37 (dd, 1H), 4.89 (s, 2H), 2.72 (s, 3H). LCMS (method A): [MH]⁺=322, $t_R$=1.97 min.

(E)-2-(1-(3-((7-Fluoroquinolin-6-yl)methyl)-[1,2,4]-triazolo[4,3-b]pyridazin-6-yl)ethylidene)hydrazinecarboxamide (Example 45)

The title compound was prepared using the same procedure as described in the synthesis of example 40. ¹H-NMR (400 MHz, DMSO-d₆) δ ppm 9.87 (s, 1H), 8.89 (dd, 1H), 8.31-8.39 (m, 2H), 8.20 (d, 1H), 8.04 (d, 1H), 7.78 (d, 1H), 7.50 (dd, 1H), 6.80 (s br, 1H), 4.75 (s, 2H), 2.21 (s, 3H). LCMS (method A): [MH]⁺=379, $t_R$=5.80 min.

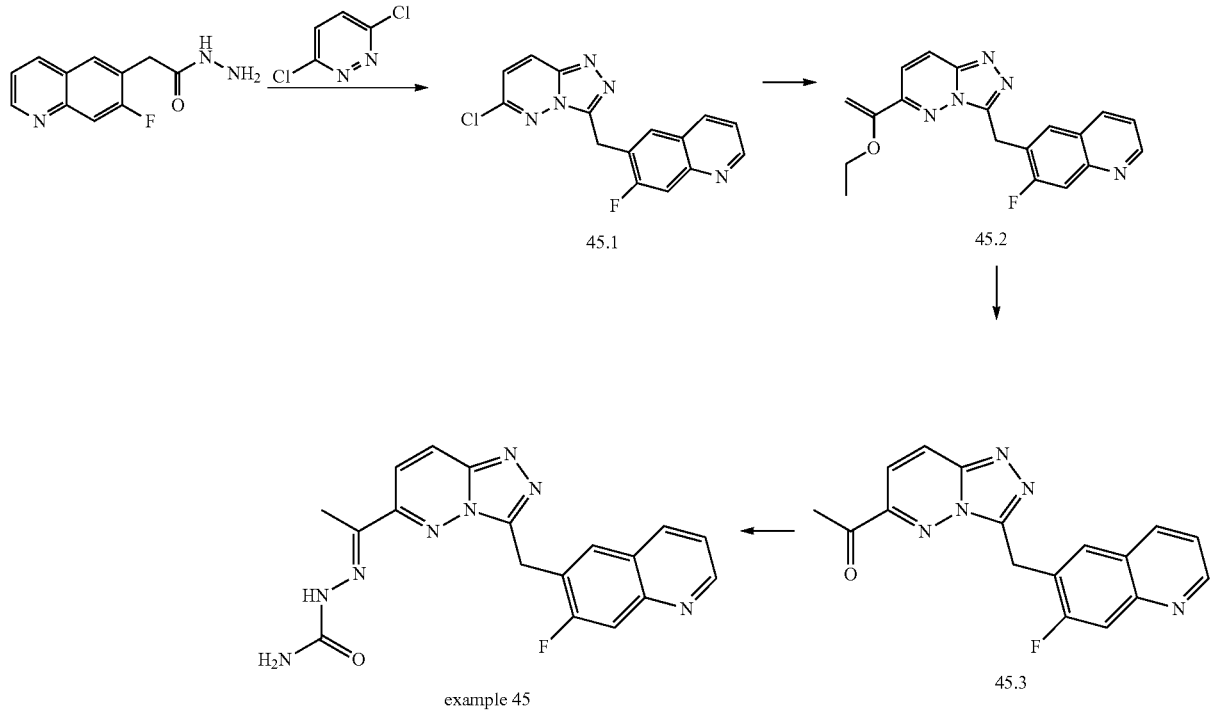

example 45

Example 46 and 46*

(E)-2-(1-(3-(1-(Quinolin-6-yl)ethyl)-[1,2,4]triazolo[4,3-b]pyridazin-6-yl)ethylidene)-hydrazinecarboxamide

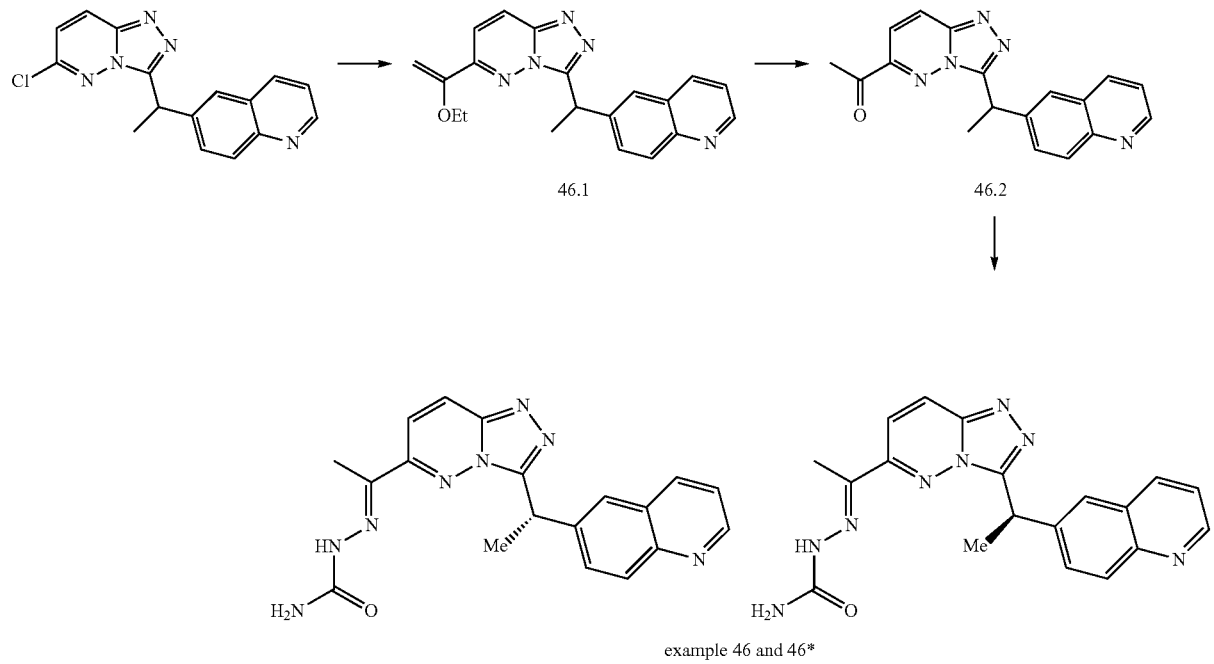

example 46 and 46*

6-{1-[6-(1-Ethoxy-vinyl)-[1,2,4]triazolo[4,3-b]pyridazin-3-yl]-ethyl}-quinoline (46.1)

The title compound was prepared using the same procedure as described in the synthesis of 40.3. LCMS (method A): [MH]$^+$=346, $t_R$=5.18 min.

1-[3-(1-Quinolin-6-yl-ethyl)-[1,2,4]triazolo[4,3-b]pyridazin-6-yl]-ethanone (46.2)

The title compound was prepared using the same procedure as described in the synthesis of 40.4. $^1$H-NMR (400 MHz, CDCl$_3$) δ ppm 8.89 (dd, 1H), 8.05-8.17 (m, 3H), 7.78-7.84 (m, 2H), 7.71 (d, 1H), 7.39 (dd, 1H), 5.05 (q, 1H), 2.62 (s, 3H), 2.11 (d, 3H). LCMS (method A): [MH]$^+$=318, $t_R$=3.88 min.

(E)-2-(1-(3-(1-(Quinolin-6-yl)ethyl)-[1,2,4]triazolo[4,3-b]pyridazin-6-yl)ethylidene)-hydrazinecarboxamide (Example 46 and 46*)

The title compound as a recemic mixture was prepared using the same procedure as described in the synthesis of example 40. $^1$H-NMR (400 MHz, DMSO-d$_6$) δ ppm 9.83 (s, 1H), 8.83 (dd, 1H), 8.28-8.33 (m, 2H), 8.16 (d, 1H), 7.92-7.97 (m, 2H), 7.78 (dd, 1H), 7.49 (dd, 1H), 6.78 (s br, 2H), 5.03 (q, 1H), 2.15 (s, 3H), 1.92 (d, 3H). LCMS (method A): [MH]$^+$= 375, $t_R$=3.99 min. Chiral separation (method G) provided enantiomeric pure compounds example 46 and 46*.

Example 47

(E)-2-(1-(3-(2-(Quinolin-6-yl)propan-2-yl)-[1,2,4]triazolo[4,3-b]pyridazin-6-yl)ethylidene)hydrazinecarboxamide

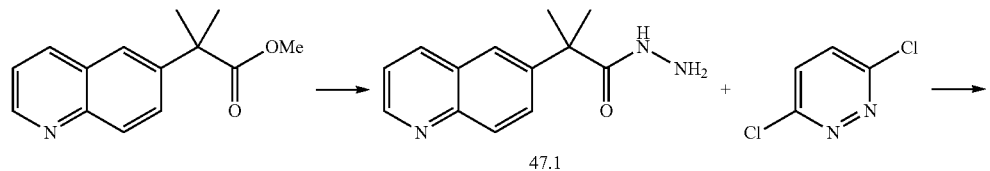

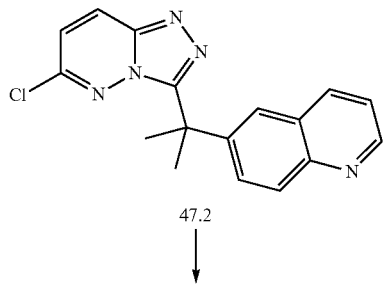

2-Methyl-2-quinolin-6-yl-propionic acid hydrazide (47.1)

The title compound was prepared using the same procedure as described in the synthesis of 40.1. LCMS (method A): [MH]⁺=230, t_R=2.71 min.

6-[1-(6-Chloro-[1,2,4]triazolo[4,3-b]pyridazin-3-yl)-1-methyl-ethyl]-quinoline (47.2)

The title compound was prepared using the same procedure as described in the synthesis of 40.2. $^1$H-NMR (400 MHz, CDCl$_3$) δ ppm 8.89 (dd, 1H), 8.03-8.17 (m, 3H), 7.86 (s, 1H), 7.83 (d, 1H), 7.41 (dd, 1H), 7.06 (d, 1H), 5.00 (q, 1H), 2.05 (d, 3H). LCMS (method A): [MH]⁺=310, t_R=3.93 min.

1-[3-(1-Methyl-1-quinolin-6-yl-ethyl)-[1,2,4]-triazolo[4,3-b]pyridazin-6-yl]-ethanone (47.3)

The title compound was prepared using the same procedure as described in the synthesis of 40.4. $^1$H-NMR (400 MHz, CDCl$_3$) δ ppm 8.88 (dd, 1H), 8.05-8.15 (m, 2H), 8.00 (d, 1H), 7.79 (d, 1H), 7.62 (d, 1H), 7.59 (dd, 1H), 7.40 (dd, 1H), 2.22 (s, 3H), 2.18 (s, 6H). LCMS (method A): [MH]⁺= 332, t_R=4.19 min.

(E)-2-(1-(3-(2-(Quinolin-6-yl)propan-2-yl)-[1,2,4]-triazolo[4,3-b]pyridazin-6-yl)ethylidene)hydrazinecarboxamide (Example 47)

The title compound was prepared using the same procedure as described in the synthesis of example 40. $^1$H-NMR (400 MHz, DMSO-d$_6$) δ ppm 9.70 (s, 1H), 8.84 (dd, 1H), 8.37 (dd, 1H), 8.23 (d, 1H), 8.16 (d, 1H), 7.97 (d, 1H), 7.88 (d, 1H), 7.47-7.52 (m, 1H), 6.76 (s br, 2H), 2.03 (s, 6H), 1.75 (s, 3H). LCMS (method A): [MH]⁺=389, t_R=4.14 min.

Example 48

(E)-1-Methyl-2-(1-(3-(2-(quinolin-6-yl)propan-2-yl)-[1,2,4]-triazolo[4,3-b]pyridazin-6-yl)ethylidene)hydrazinecarboxamide

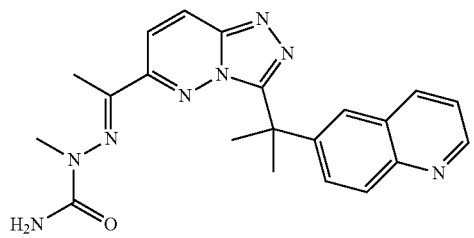 [SMILES: C/C(=N\N(C)C(N)=O)c1ccc2nnc(C(C)(C)c3ccc4ncccc4c3)n2n1]

The title compound was prepared using the same procedure as described in the synthesis of example 47. $^1$H-NMR (400 MHz, CDCl$_3$) δ ppm 8.87 (dd, 1H), 8.09 (dd, 1H), 8.00 (d, 1H), 7.97 (d, 1H), 7.77 (d, 1H), 7.69 (d, 1H), 7.56 (dd, 1H), 7.38 (dd, 1H), 5.47 (s br, 1H), 3.25 (s, 3H), 2.13 (s, 6H), 1.96 (s, 3H). LCMS (method A): [MH]⁺=403, t_R=4.17 min.

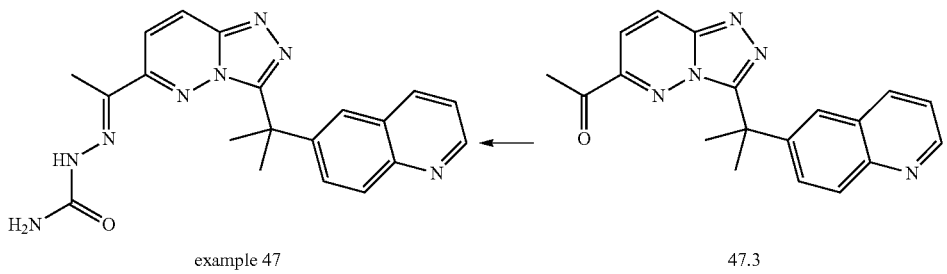

Example 49

(E)-2-(1-(3-(1-(5,7-Difluoroquinolin-6-yl)ethyl)-[1,2,4]triazolo[4,3-b]pyridazin-6-yl)ethyl idene)hydrazinecarboxamide

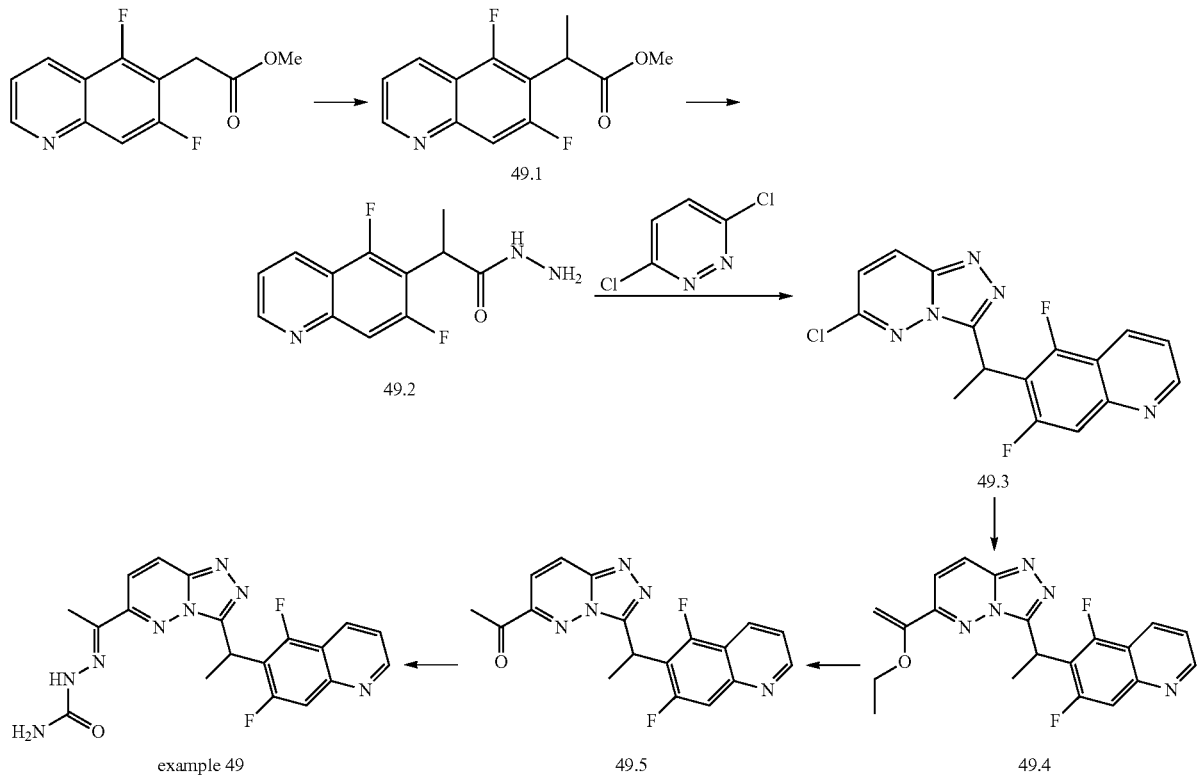

2-(5,7-Difluoro-quinolin-6-yl)-propionic acid methyl ester (49.1)

To a solution of LDA (1.2 M in THF, 9.5 mL, 11.40 mmol) in dry THF (30 mL) at −78° C. was added dropwise a solution of (5,7-difluoroquinolin-6-yl)-acetic acid methyl ester (2.12 g, 9.50 mmol) in THF (20 mL). After 30 min, MeI (0.9 mL, 14.25 mmol) was added dropwise, and the reaction mixture was allowed to rise to 0° C. slowly. After 1 h, the reaction was quenched by satd. aq. NaHCO$_3$ solution, and extracted with EtOAc. The organic layer was washed with brine, dried over anhydrous Na$_2$SO$_4$, filtered, concentrated, and purified by flash chromatography to afford 2.272 g of the title compound as pale yellow solid. $^1$H-NMR (400 MHz, CDCl$_3$) δ ppm 8.93 (d, 1H), 8.39 (dd, 1H), 7.61 (dd, 1H), 7.41-7.46 (m, 1H), 4.29 (q, 1H), 3.73 (s, 3H), 1.62 (d, 3H). LCMS (method A): [MH]$^+$= 252, t$_R$=5.09 min.

2-(5,7-Difluoro-quinolin-6-yl)-propionic acid hydrazide (49.2)

The title compound was prepared using the same procedure as described in the synthesis of 40.1. $^1$H-NMR (400 MHz, DMSO-d$_6$) δ ppm 9.06 (s, 1H), 8.97 (dd, 1H), 8.45 (d, 1H), 7.58-7.67 (m, 2H), 4.23 (s br, 2H), 4.08 (q, 1H), 1.51 (d, 3H). LCMS (method A): [MH]$^+$=252, t$_R$=3.82 min.

6-[1-(6-Chloro-[1,2,4]triazolo[4,3-b]pyridazin-3-yl)-ethyl]-5,7-difluoro-quinoline (49.3)

The title compound was prepared using the same procedure as described in the synthesis of 40.2. $^1$H-NMR (400 MHz, CDCl$_3$) δ ppm 8.93 (dd, 1H), 8.36 (dd, 1H), 8.07 (d, 1H), 7.62 (dd, 1H), 7.43 (dd, 1H), 7.05 (d, 1H), 5.26 (q, 1H), 2.13 (d, 1H). LCMS (method A): [MH]$^+$=346, t$_R$=5.00 min.

6-{1-[6-(1-Ethoxy-vinyl)-[1,2,4]-triazolo[4,3-b]pyridazin-3-yl]-ethyl}-5,7-difluoro-quinoline (49.4)

The title compound was prepared using the same procedure as described in the synthesis of 40.3. LCMS (method A): [MH]$^+$=382, t$_R$=5.05 min.

1-{3-[1-(5,7-Difluoro-quinolin-6-yl)-ethyl]-[1,2,4]triazolo[4,3-b]pyridazin-6-yl}-ethanone (49.5)

The title compound was prepared using the same procedure as described in the synthesis of 40.4. $^1$H-NMR (400 MHz, CDCl$_3$) δ ppm 8.92 (dd, 1H), 8.32 (d, 1H), 8.14 (d, 1H), 7.68 (d, 1H), 7.61 (d, 1H), 7.42 (dd, 1H), 5.32 (q, 1H), 2.43 (s, 3H), 2.21 (d, 3H). LCMS (method A): [MH]$^+$=354, t$_R$=4.42 min.

(E)-2-(1-(3-(1-(5,7-Difluoroquinolin-6-yl)ethyl)-[1,2,4]triazolo[4,3-b]pyridazin-6-yl)ethylidene)hydrazinecarboxamide (Example 49)

The title compound was prepared using the same procedure as described in the synthesis of example 40. ¹H-NMR (400 MHz, DMSO-$d_6$) δ ppm 9.76 (s, 1H), 8.96 (d, 1H), 8.44 (d, 1H), 8.29 (d, 1H), 8.17 (d, 1H), 7.70 (d, 1H), 7.59 (dd, 1H), 6.77 (s br, 2H), 5.24 (q, 1H), 2.01 (d, 3H), 1.87 (s, 3H). LCMS (method A): [MH]$^+$=411, $t_R$=4.28 min.

Example 50

(E)-1-Methyl-2-(1-(3-(1-(quinolin-6-yl)cyclopropyl)-[1,2,4]triazolo[4,3-b]pyridazin-6-yl)ethylidene)hydrazinecarboxamide

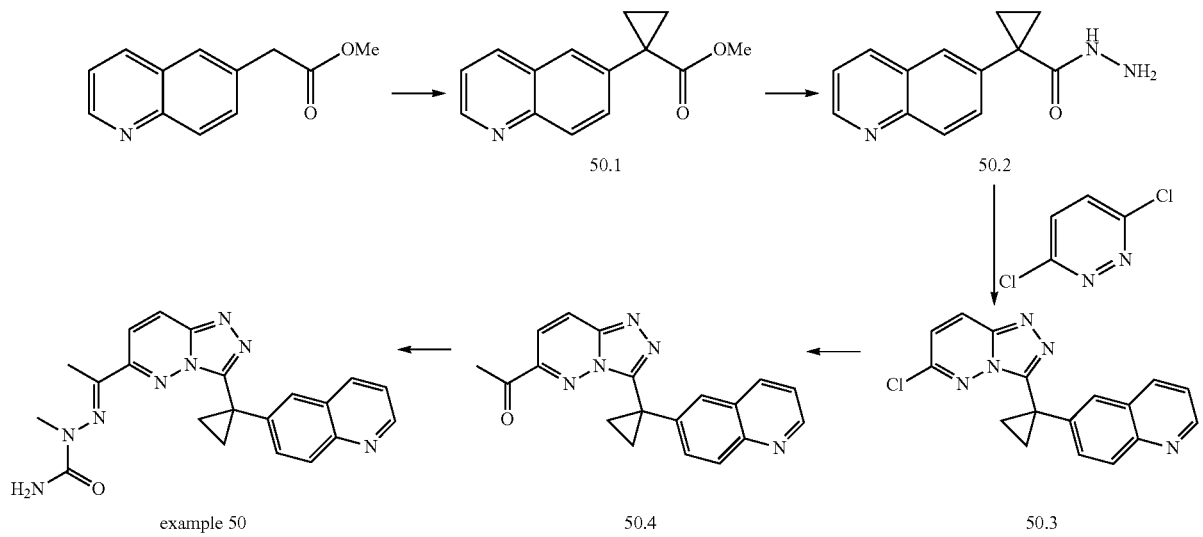

example 50         50.4         50.3

1-Quinolin-6-yl-cyclopropanecarboxylic acid methyl ester (50.1)

A solution of LDA (1.8 M solution in toluene, 14.8 ml, 26.6 mmol) was added dropwise to a solution of quinolin-6-yl-acetic acid methyl ester (2.14 g, 10.64 mmol) in dry THF (40 mL) under a nitrogen atmosphere at −78° C. After 30 min, 1,2-dibromoethane (2.40 g, 12.76 mmol) was added dropwise over 3 min. The resulting mixture was stirred for 1 h at room temperature, then quenched with satd aq. NH$_4$Cl. The mixture was extracted with DCM, washed with brine, dried over Na$_2$SO$_4$, and stripped of solvent. The residue was purified by flash chromatography in silica gel eluting with a EtOAC/hexane gradient to afford 463 mg (20%) of the title compound as yellow solid. ¹H-NMR (400 MHz, CDCl$_3$) δ ppm 8.91 (dd, 1H), 8.12 (d, 1H), 8.07 (d, 1H), 7.77-7.74 (m, 2H), 7.40 (dd, 1H), 3.65 (s, 3H), 1.73-1.71 (m, 2H), 1.33-1.30 (m, 2H). LCMS (method A): [MH]$^+$=228, $t_R$=4.37 min.

1-Quinolin-6-yl-cyclopropanecarboxylic acid hydrazide (50.2)

A solution of 1-quinolin-6-yl-cyclopropanecarboxylic acid methyl ester (513 mg, 2.26 mmol) and hydrazine monohydrate (3.39 g, 67.7 mmol) in methanol (5 mL) was heated under reflux overnight. After cooling, the solvent was removed in vacuo to afford 513 mg (100%) of the title compound and used without further purification. LCMS (method A): [MH]$^+$=228, $t_R$=2.88 min.

6-[1-(6-Chloro-[1,2,4]triazolo[4,3-b]pyridazin-3-yl)-cyclopropyl]-quinoline (50.3)

A microwave tube was charged with 1-quinolin-6-yl-cyclopropanecarboxylic acid hydrazide (513 mg, 2.26 mmol), 3,6-dichloropyridazine (437 mg, 2.93 mmol) and n-butanol (5 mL). The mixture was heated at 140° C. for 12 h. The solvent was removed in vacuo and the residue was purified by flash chromatography in silica gel eluting with ETOAC/methanol gradient to afford 196 mg (41%) of the title compound. LCMS (method A): [MH]$^+$=322, $t_R$=4.38 min.

1-[3-(1-Quinolin-6-yl-cyclopropyl)-[1,2,4]triazolo[4,3-b]pyridazin-6-yl]-ethanone (50.4)

A solution of 6-[1-(6-chloro-[1,2,4]triazolo[4,3-b]pyridazin-3-yl)-cyclopropyl]-quinoline (30 mg, 0.093 mmol), PdCl$_2$(PPh$_3$)$_2$ (6.5 mg, 0.0093 mmol) and tributyl(1-ethoxyvinyl)stannane (67 mg, 0.186 mmol) in 1,4-dioxane (3 mL) was heated at 90° C. for 3 h under N$_2$. The reaction mixture was diluted with EtOAc, washed with aqueous KF. The organic layer was dried over Na$_2$SO$_4$, filtered and concentrated in vacuo. The residue was dissolved in HOAc and 3 N HCl, and stirred at room temperature for 3 h. The solvent was removed in vacuo and the residue was dissolved in DCM, washed with sat. aq. NaHCO$_3$ and brine. The organic layer was dried over Na$_2$SO$_4$, filtered and concentrated in vacuo. The residue was purified by flash chromatography in silica gel eluting with a EtOAC/MeOH gradient to afford the title compound as yellow solid. ¹H-NMR (400 MHz, CDCl$_3$) δ ppm 8.89 (dd, 1H); 8.13-8.04 (m, 3H), 7.93 (d, 1H), 7.87 (dd, 1H), 7.70 (d, 1H), 7.40 (dd, 1H), 2.51 (s, 3H), 1.92-1.89 (m, 2H), 1.73-1.69 (m, 2H). LCMS (method A): [MH]$^+$=330, $t_R$=4.18 min.

(E)-1-Methyl-2-(1-(3-(1-(quinolin-6-yl)cyclopropyl)-[1,2,4]triazolo[4,3-b]pyridazin-6-yl)ethylidene)hydrazinecarboxamide (Example 50)

A solution of 1-[3-(1-quinolin-6-yl-cyclopropyl)-[1,2,4]triazolo[4,3-b]pyridazin-6-yl]-ethanone (30 mg, 0.091 mmol), acetic acid (0.1 mL) and 1-methylhydrazinecarboxamide (16.2 mg, 0.18 mmol) in methanol (5 mL) was stirred at room temperature overnight. The solvent was removed in vacuo and the residue was diluted with DCM, washed with sat. aqueous NaHCO$_3$. The organic layer was dried over Na$_2$SO$_4$, filtered and concentrated in vacuo. The residue was purified by flash chromatography in silica gel eluting with a CH$_2$Cl$_2$/MeOH gradient to afford the title compound (14.9 mg, 41%) as yellow solid. $^1$H-NMR (400 MHz, DMSO-d$_6$) δ ppm 8.84 (dd, 1H), 8.30 (d, 1H), 8.22 (d, 1H), 8.13 (d, 1H), 7.94-7.92 (m, 2H), 7.70 (dd, 1H), 7.49 (dd, 1H), 6.64 (s, 2H), 3.21 (s, 3H), 2.16 (s, 3H), 1.78-1.75 (m, 2H), 1.68-1.65 (m, 2H). LCMS (method A): [MH]$^+$=401, t$_R$=4.11 min.

Example 51

(E)-2-(1-(3-(Quinolin-6-ylmethyl)imidazo[1,2-a]pyrimidin-6-yl)ethylidene)hydrazinecarboxamide

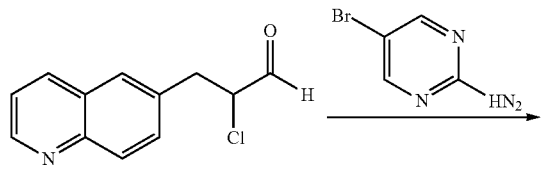

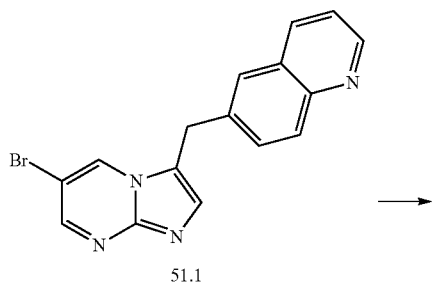

51.1

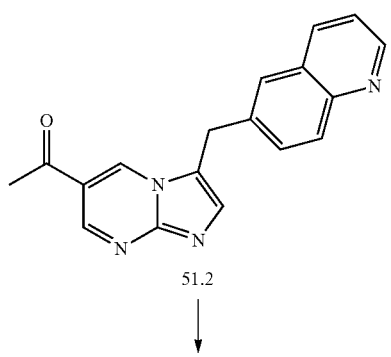

51.2

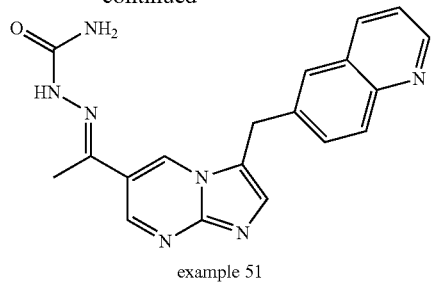

example 51

6-((6-Bromoimidazo[1,2-a]pyrimidin-3-yl)methyl)quinoline (51.1)

A solution of 2-chloro-3-(quinolin-6-yl)propanal (1.0 g, 2.54 mmol) and 5-bromopyrimidin-2-amine (0.53 g, 3.05 mmol) in 2-methyl-butan-2-ol (10 mL) was stirred at 135° C. for 12 h. After cooling, the solvent was removed in vacuo and the residue was purified by flash chromatography in silica gel eluting with a CH$_2$Cl$_2$/MeOH gradient to afford a mixture of the title compound and 6-(6-bromo-imidazo[1,2-a]pyrimidin-2-ylmethyl)quinoline (250 mg, 29%) as brown solid. LCMS (method E): [MH]$^+$=339/341, t$_R$=3.51 min.

1-(3-(Quinolin-6-ylmethyl)imidazo[1,2-a]pyrimidin-6-yl)ethanone (51.2)

A solution of 6-((6-bromoimidazo[1,2-a]pyrimidin-3-yl)methyl)quinoline and 6-(6-bromo-imidazo[1,2-a]pyrimidin-2-ylmethyl)quinoline (mixture, 250 mg, 0.737 mmol), PdCl$_2$(PPh$_3$)$_2$ (51.7 mg, 0.074 mmol) and tributyl(1-ethoxyvinyl)stannane (399 mg, 1.106 mmol) in 5 mL of 1,4-dioxane was heated at 80° C. for 12 h under N$_2$. The reaction mixture was diluted with EtOAc, washed with water. The organic layer was dried over Na$_2$SO$_4$, filtered and concentrated in vacuo. The residue was dissolved in HOAc and 3 N HCl and stirred at room temperature for 3 hours. The solvent was removed under reduced pressure and the residue was dissolved in CH$_2$Cl$_2$, washed with sat. aqueous NaHCO$_3$ and brine. The organic layer was dried over Na$_2$SO$_4$, filtered and concentrated in vacuo. The residue was purified by flash chromatography in silica gel eluting with a EtOAc/MeOH gradient to afford the title compound as a yellow solid. $^1$H-NMR (400 MHz, CDCl$_3$) δ ppm 8.97 (d, 1H), 8.84 (d, 1H), 8.67 (d, 1H), 8.04-7.99 (m, 2H), 7.74 (s, 1H), 7.53-7.51 (m, 1H), 7.34 (dd, 1H), 7.19 (s, 1H), 4.44 (s, 2H), 2.49 (s, 3H).

(E)-2-(1-(3-(Quinolin-6-ylmethyl)imidazo[1,2-a]pyrimidin-6-yl)ethylidene)-hydrazinecarboxamide (Example 51)

A solution of 1-(3-(quinolin-6-ylmethyl)imidazo[1,2-a]pyrimidin-6-yl)ethanone (40 mg, 0.132 mmol) and hydrazinecarboxamide hydrochloride (14.9 mg, 0.198 mmol) in methanol (3 mL) was stirred at 40° C. for 2 h. The solvent was removed in vacuo and the residue was purified by HPLC to afford 4.2 mg (8.8%) of the title compound as white solid. $^1$H-NMR (400 MHz, DMSO-d$_6$) δ ppm 9.45 (s, 1H), 9.24 (d, 1H), 8.91 (d, 1H), 8.86 (dd, 1H), 8.30 (d, 1H), 7.98 (d, 1H), 7.89 (s, 1H), 7.72 (dd, 1H), 7.52-7.49 (m, 2H), 6.65 (s, 2H), 4.59 (s, 2H), 2.18 (s, 3H). LCMS (method A): [MH]$^+$=360, t$_R$=2.95 min.

Example 52

(E)-2-(1-(1-(Quinolin-6-ylmethyl)-1H-[1,2,3]triazolo[4,5-b]pyrazin-6-yl)ethylidene)hydrazinecarboxamide

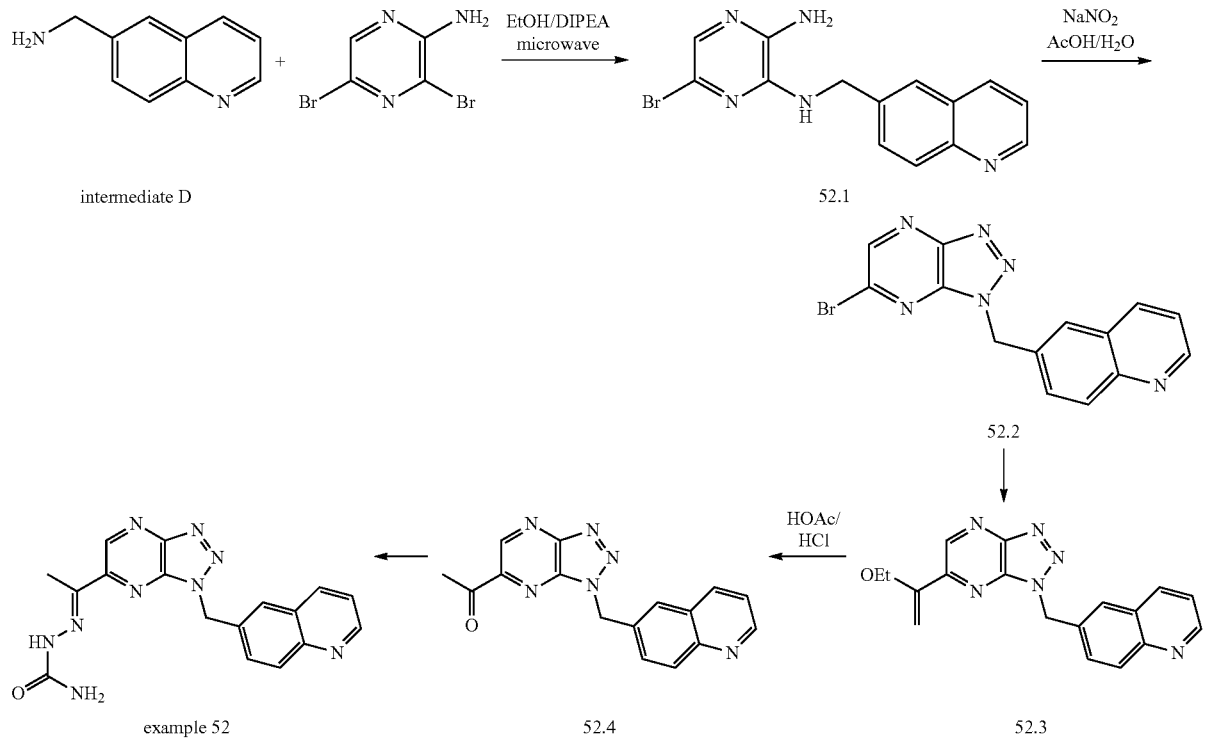

6-Bromo-N2-(quinolin-6-ylmethyl)pyrazine-2,3-diamine (52.1)

A mixture of quinolin-6-ylmethanamine (3.6 g, 22.76 mmol), 3,5-dibromopyrazin-2-amine (5.75 g, 22.76 mmol) and triethyl amine (4.61 g, 45.5 mmol) was heated in a microwave to 130° C. for 5 h. The reaction mixture was diluted with $CH_2Cl_2$ and water and the organic layer was separated, washed with aqueous $NH_4Cl$, dried over $Na_2SO_4$, filtered and concentrated in vacuo. The residue was purified by silica gel chromatography with EA:Hexanes to provide 6-bromo-N2-(quinolin-6-ylmethyl)pyrazine-2,3-diamine (6.93 g, 92%). LCMS (method A): $[MH]^+=330$, $t_R=4.89$ min.

6-((6-Bromo-1H-[1,2,3]triazolo[4,5-b]pyrazin-1-yl)methyl)quinoline (52.2)

To a solution of 6-bromo-N2-(quinolin-6-ylmethyl)pyrazine-2,3-diamine (6.55 g, 19.84 mmol) in acetic acid (15 mL), was added a the solution of sodium nitrite (2.74 g, 39.7 mmol) in water (3 mL). After stirring at rt for 3 h, the solution was concentrated in vacuo. The residue was taken with $NaHCO_3$ (aq), extracted with DCM. The organic layer was washed with $NH_4Cl(aq)$, dried over $Na_2SO_4$, filtered, concentrated in vacuo and purified by silica gel chromatography with EA:Hexanes to provide 6-((6-bromo-1H-[1,2,3]triazolo[4,5-b]pyrazin-1-yl)methyl)quinoline (3.35 g, 47%). $^1$H-NMR (400 MHz, DMSO-$d_6$) δ ppm 9.05 (s, 1H), 8.89 (d, 1H), 8.34 (d, 1H), 8.02 (d, 1H), 7.9 3 (s, 1H), 7.76 (dd, 1H), 7.53 (dd, 1H), 6.19 (s, 2H). LCMS (method B): $[MH]^+=343$, $t_R=2.11$ min.

6-((6-(1-Ethoxyvinyl)-1H-[1,2,3]triazolo[4,5-b]pyrazin-1-yl)methyl)quinoline (52.3)

To a degassed solution of 6-((6-bromo-1H-[1,2,3]triazolo[4,5-b]pyrazin-1-yl)methyl)quino-line (2.50 g, 5.86 mmol) in DMF (20 mL), was added $Pd(Ph_3P)_4$ (0.542 g, 0.469 mmol) and the solution was stirred for 20 min at room temperature. Then tributyl(1-ethoxyvinyl)stannane (2.117 g, 5.86 mmol) was added. The reaction was heated to 100° C. until LC-MS showed the reaction was complete. The reaction mixture was filtered through celite and the filtrate was washed with water, dried over $Na_2SO_4$, and concentrated. The resulting crude product was purified by silica gel column chromatography with gradient Hex:EA to give 6-((6-(1-ethoxyvinyl)-1H-[1,2,3]triazolo[4,5-b]pyrazin-1-yl)methyl)quinoline (1.2 g, 62%). $^1$H-NMR (400 MHz, $CDCl_3$) δ ppm 9.19 (s, 1H), 8.94 (m, 1H), 8.20 (m, 1H), 7.99 (s, 1H), 7.89 (d, 1H), 7.548 (m, 1H), 6.12 (s, 2H), 5.61 (d, 1H), 4.61 (d, 1H), 4.05 (q, 2H), 1.51 (t, 3H). LCMS (method B): $[MH]^+=360$, $t_R=2.40$ min.

1-(1-(Quinolin-6-ylmethyl)-1H-[1,2,3]triazolo[4,5-b]pyrazin-6-yl)ethanone (52.4)

To a solution of the 6-((6-(1-ethoxyvinyl)-1H-[1,2,3]triazolo[4,5-b]pyrazin-1-yl)methyl)quinoline (150 mg, 0.451 mmol) in acetic acid, was added 3N HCl (0.1 mL). After the solution was stirred at rt for 2 h, solvents was removed under reduced pressure. The residue was diluted with water and its pH was adjusted to basic with aqueous NaHCO$_3$, extracted with DCM. The combined organic layers were washed with NaHCO$_3$(aq) and brine, dried over Na$_2$SO$_4$, filtered and concentrated in vacuo. The residue was purified by silica gel column chromatography to give a yellow solid of 1-(1-(quinolin-6-ylmethyl)-1H-[1,2,3]triazolo[4,5-b]pyrazin-6-yl)ethanone (131 mg, 91%). $^1$H-NMR (400 MHz, CDCl$_3$) δ ppm 9.45 (s, 1H), 8.95 (d, 1H), 8.14 (m, 2H), 7.95 (s, 1H), 7.84 (d, 1H), 7.45 (m, 1H), 6.19 (s, 2H), 2.75 (s, 3H). LCMS (method B): [MH]$^+$=305, t$_R$=2.95 min.

(E)-2-(1-(1-(Quinolin-6-ylmethyl)-1H-[1,2,3]triazolo[4,5-b]pyrazin-6-yl)ethylidene)hydrazinecarboxamide (Example 52)

To a solution of 1-(1-(quinolin-6-ylmethyl)-1H-[1,2,3]triazolo[4,5-b]pyrazin-6-yl)ethanone (35 mg, 0.115 mmol) in MeOH (3 mL), was added hydrazinecarboxamide hydrochloride (115 mg, 1.035 mmol). The solution was heated to 37° C. overnight. Triethyl amine (1 mL) was added and the solution was stirred at rt for 20 min. Solvents were removed in vacuo and the residue was diluted with DCM, washed with brine, dried over Na$_2$SO$_4$, filtered and concentrated in vacuo to afford 25 mg of the title compound in 57% yield as a white solid. $^1$H-NMR (400 MHz, DMSO-d$_6$) δ ppm 9.90 (s, 1H), 9.85 (s, 1H), 8.89 (m, 1H), 3.36 (d, 1H), 8.01 (m, 2H), 7.82 (d, 1H), 7.53 (dd, 1H), 6.17 (s, 2H), 2.32 (s, 3H). LCMS (method A): [MH]$^+$=384, t$_R$=4.09 min.

Example 53

(E)-2-Morpholino-N'-(1-(1-(quinolin-6-ylmethyl)-1H-[1,2,3]triazolo[4,5-b]pyrazin-6-yl)ethylidene)acetohydrazide

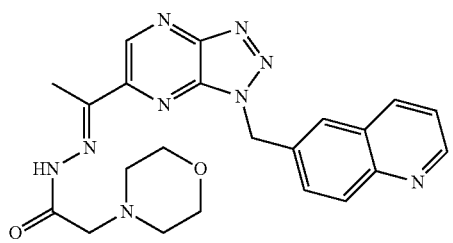 [SMILES: C/C(=N\NC(=O)CN1CCOCC1)c1cnc2nnn(Cc3ccc4ncccc4c3)c2n1]

The title compound was prepared in analogy to the synthesis of example 52 from 1-(1-(quinolin-6-ylmethyl)-1H-[1,2,3]triazolo[4,5-b]pyrazin-6-yl)ethanone and 2-morpholinoaceto-hydrazide. The title compound was obtained as light yellow solid. $^1$H-NMR (400 MHz, DMSO-d$_6$) δ ppm 9.45 (d, 1H), 8.90 (d, 1H), 8.36 (d, 1H), 8.01 (m, 2H), 7.83 (d, 1H), 7.53 (dd, 1H), 6.20 (s, 2H), 3.65 (d, 4H), 3.26 (s, 2H), 2.57 (d, 4H), 2.41 (s, 3H). LCMS (method B): [MH]$^+$=446.2, t$_R$=1.37 min.

Example 54

(E)-2-(4-Methylpiperazin-1-yl)-N'-(1-(1-(quinolin-6-ylmethyl)-1H-[1,2,3]triazolo[4,5-b]pyrazin-6-yl)ethylidene)acetohydrazide

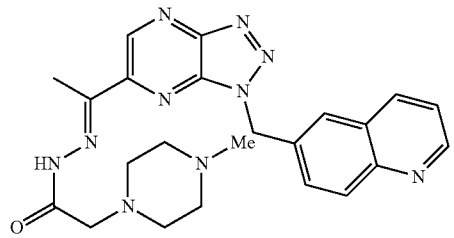 [SMILES: C/C(=N\NC(=O)CN1CCN(C)CC1)c1cnc2nnn(Cc3ccc4ncccc4c3)c2n1]

The title compound was prepared as a light yellow solid in analogy to the synthesis of example 52 from 1-(1-(quinolin-6-ylmethyl)-1H-[1,2,3]triazolo[4,5-b]pyrazin-6-yl). LCMS (method B): [MH]$^+$=459, t$_R$=1.35 min.

Example 55

(E)-3-(1-(1-(Quinolin-6-ylmethyl)-1H-[1,2,3]triazolo[4,5-b]pyrazin-6-yl)ethylideneamino)oxazolidin-2-one

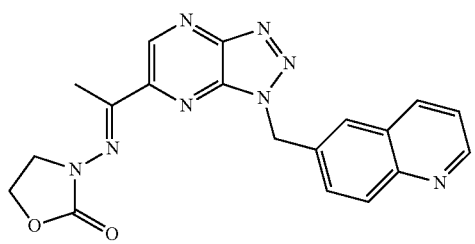 [SMILES: C/C(=N\N1CCOC1=O)c1cnc2nnn(Cc3ccc4ncccc4c3)c2n1]

The title compound was prepared in analogy to the synthesis of example 52 from 1-(1-(quinolin-6-ylmethyl)-1H-[1,2,3]triazolo[4,5-b]pyrazin-6-yl)ethanone and 3-aminooxazolidin-2-one. $^1$H-NMR (400 MHz, DMSO-d$_6$) δ ppm 9.42 (s, 1H), 8.89 (m, 1H), 8.36 (d, 1H), 8.02 (m, 2H), 7.84 (m, 1H), 7.53 (m, 1H), 6.24 (s, 2H), 4.51 (t, 2H), 4.15 (t, 1H), 4.08 (t, 2H), 2.73 (s, 1H), 2.46 (s, 3H). LCMS (method B): [MH]$^+$= 389, $t_R$=1.87 min.

Example 56

(E)-1-(1-(1-(quinolin-6-ylmethyl)-1H-[1,2,3]triazolo[4,5-b]pyrazin-6-yl)ethylideneamino)-imidazolidine-2,4-dione

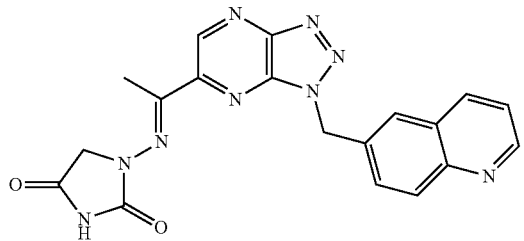 [SMILES: C/C(=N\N1CC(=O)NC1=O)c1cnc2nnn(Cc3ccc4ncccc4c3)c2n1]

The title compound was prepared in 58% yield as a light yellow solid in analogy to the synthesis of example 52 from 1-aminoimidazolidine-2,4-dione hydrochloride and 1-(1-(quinolin-6-ylmethyl)-1H-[1,2,3]triazolo[4,5-b]pyrazin-6-yl)ethanone. $^1$H-NMR (400 MHz, DMSO-d$_6$) δ ppm 11.45 (s, 1H), 9.41 (s, 1H), 8.89 (d, 1H), 8.35 (d, 1H), 8.02 (m, 2H), 7.84 (d, 1H), 7.53 (dd, 1H), 6.23 (s, 2H), 4.56 (s, 2H), 2.49 (s, 3H). LCMS (method B): [MH]$^+$=402, $t_R$=1.81 min.

Example 57

(E)-1-(1-(1-(quinolin-6-ylmethyl)-1H-[1,2,3]triazolo[4,5-b]pyrazin-6-yl)ethylideneamino)-imidazolidin-2-one

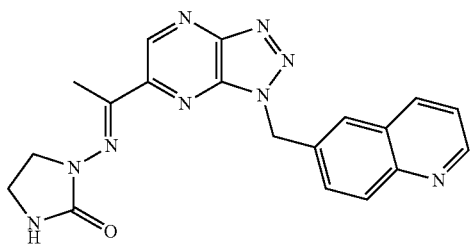 [SMILES: C/C(=N\N1CCNC1=O)c1cnc2nnn(Cc3ccc4ncccc4c3)c2n1]

The title compound was prepared in 26% yield as a light yellow solid in analogy to the synthesis of example 52 from 1-(1-(quinolin-6-ylmethyl)-1H-[1,2,3]triazolo[4,5-b]pyrazin-6-yl)ethanone and 1-aminoimidazolidin-2-one. $^1$H-NMR (400 MHz, DMSO-d$_6$) δ ppm 9.42 (s, 1H), 8.89 (d, 1H), 8.35 (d, 1H), 8.02 (m, 2H), 7.84 (d, 1H), 7.53 (dd, 1H), 7.36 (s, 1H), 6.22 (s, 2H), 3.75 (t, 2H), 3.41 (t, 2H), 2.42 (s, 3H). LCMS (method B): [MH]$^+$=388, $t_R$=1.89 min.

Example 58

(E)-N'-(1-(1-(Quinolin-6-ylmethyl)-1H-[1,2,3]triazolo[4,5-b]pyrazin-6-yl)ethylidene)-methanesulfonohydrazide

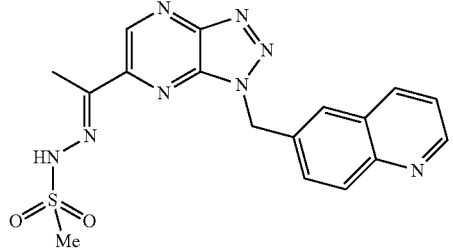 [SMILES: C/C(=N\NS(C)(=O)=O)c1cnc2nnn(Cc3ccc4ncccc4c3)c2n1]

The title compound was prepared in analogy to the synthesis of example 52 from 1-(1-(quinolin-6-ylmethyl)-1H-[1,2,3]triazolo[4,5-b]pyrazin-6-yl)ethanone and methanesulfonohydrazide. $^1$H-NMR (400 MHz, DMSO-d$_6$) δ ppm 9.45 (s, 1H), 8.89 (m, 1H), 8.36 (d, 1H), 7.82 (m, 2H), 7.85 (dd, 1H), 7.53 (dd, 1H), 6.21 (s, 2H), 3.20 (s, 3H), 2.35 (s, 3H)). LCMS (method B): [MH]$^+$=446, $t_R$=1.37 min.

Example 59

[1-(3-Quinolin-6-ylmethyl-3H-[1,2,3]triazolo[4,5-b]pyrazin-5-yl)-eth-(E)-ylidene]-hydrazine

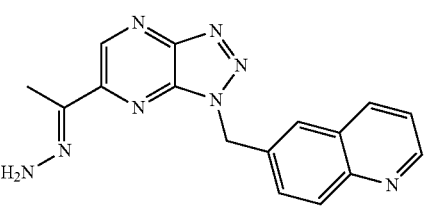 [SMILES: C/C(=N\N)c1cnc2nnn(Cc3ccc4ncccc4c3)c2n1]

The title compound was prepared in 36% yield in analogy to the synthesis of example 52 from 1-(1-(quinolin-6-ylmethyl)-1H-[1,2,3]triazolo[4,5-b]pyrazin-6-yl)ethanone. $^1$H-NMR (400 MHz, DMSO-d$_6$) δ ppm 9.50, 9.3 (s, 1H), 8.89

(m, 1H), 8.35 (d, 1H), 7.99 (m, 2H), 7.80 (d, 1H), 7.72 (s, 1H), 7.53 (dd, 1H), 6.22, 6.12 (s, 2H), 2.28, 2.14 (s, 3H).

Example 60

(E)-1-Methyl-2-(1-(1-(quinolin-6-ylmethyl)-1H-[1,2,3]triazolo[4,5-b]pyrazin-6-yl)ethylidene)hydrazinecarboxamide

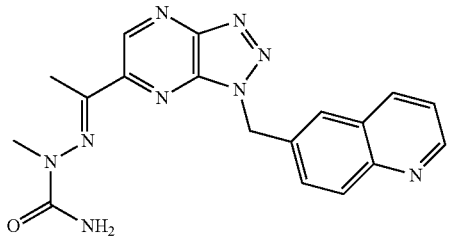 [SMILES: C/C(=N\N(C)C(N)=O)c1cnc2nnn(Cc3ccc4ncccc4c3)c2n1]

The title compound was prepared as a white solid in analogy to the synthesis of example 52 from 1-(1-(quinolin-6-ylmethyl)-1H-[1,2,3]triazolo[4,5-b]pyrazin-6-yl)ethanone and 1-methylhydrazine-carboxamide. $^1$H-NMR (400 MHz, DMSO-d$_6$) δ ppm 9.68 (s, 1H), 8.89 (m, 1H), 8.36 (d, 1H), 8.03 (s, 1H), 8.01 (d, 1H), 7.82 (dd, 1H), 7.53 (dd, 1H), 6.75 (s, 2H), 6.21 (s, 2H) 2.50 (s, 3H), 2.49 (s, 3H). LCMS (method B): [MH]$^+$=376, t$_R$=1.88 min.

Example 61

(E)-N-Methyl-2-(1-(1-(quinolin-6-ylmethyl)-1H-[1,2,3]triazolo[4,5-b]pyrazin-6-yl)ethylidene)hydrazinecarboxamide

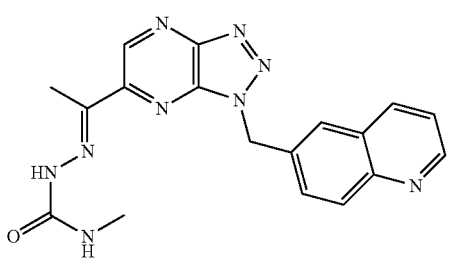 [SMILES: CNC(=O)N/N=C(\C)c1cnc2nnn(Cc3ccc4ncccc4c3)c2n1]

The title compound was prepared in analogy to the synthesis of example 52 from 1-(1-(quinolin-6-ylmethyl)-1H-[1,2,3]triazolo[4,5-b]pyrazin-6-yl)ethanone and N-methylhydrazine-carboxamide. $^1$H-NMR (400 MHz, DMSO-d$_6$) δ ppm 10.04 (s, 1H), 9.88 (s, 1H), 8.89 (m, 1H), 8.36 (d, 1H), 8.02

(m, 2H), 7.82 (d, 1H), 7.52 (dd, 1H), 7.45 (m, 1H), 6.17 (s, 2H), 2.74 (d, 3H), 2.31 (s, 3H). LCMS (method B): [MH]$^+$=376, t$_R$=2.95 min.

Example 62

(E)-N,1-Dimethyl-2-(1-(1-(quinolin-6-ylmethyl)-1H-[1,2,3]triazolo[4,5-b]pyrazin-6-yl)ethylidene)hydrazinecarboxamide

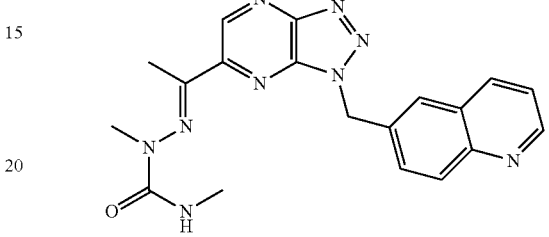

The title compound was prepared in analogy to the synthesis of example 52 from 1-(1-(quinolin-6-ylmethyl)-1H-[1,2,3]triazolo[4,5-b]pyrazin-6-yl)ethanone and N,1-dimethyl-hydrazinecarboxamide. $^1$H-NMR (400 MHz, DMSO-d$_6$) δ ppm 9.73 (s, 1H), 8.89 (m, 1H), 8.36 (dd, 1H), 8.03 (s, 1H), 8.00 (d, 1H), 7.53 (dd, 1H), 7.19 (m, 1H), 6.21 (s, 2H), 3.31 (s, 3H), 2.72 (d, 3H), 2.49 (d, 3H). LCMS (method B): [MH]$^+$=390, t$_R$=1.99 min.

Example 63

(E)-1-Ethyl-2-(1-(1-(quinolin-6-ylmethyl)-1H-[1,2,3]triazolo[4,5-b]pyrazin-6-yl)ethylidene)hydrazinecarboxamide

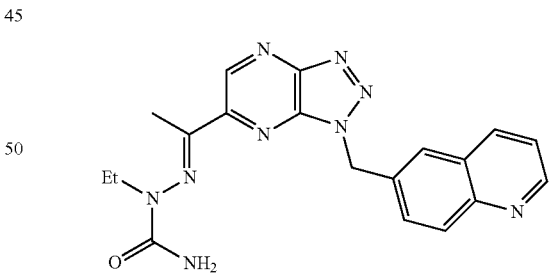

The title compound was prepared in 57% yield as a white solid in analogy to the synthesis of example 52 from 1-(1-(quinolin-6-ylmethyl)-1H-[1,2,3]triazolo[4,5-b]pyrazin-6-yl)ethanone and 1-ethylhydrazine-carboxamide. $^1$H-NMR (400 MHz, DMSO-d$_6$) δ ppm 9.61 (s, 1H), 8.89 (d, 1H), 8.36 (d, 1H), 8.03 (s, 1H), 8.00 (d, 1H), 7.83 (d, 1H), 7.53 (m, 1H), 6.61 (d, 2H), 6.22 (s, 2H), 3.80 (q, 2H), 2.42 (s, 3H), 1.07 (t, 3H). LCMS (method B): [MH]$^+$=390, $t_R$=1.98 min.

Example 64

(E)-N'-Acetyl-1-(quinolin-6-ylmethyl)-1H-[1,2,3]triazolo[4,5-b]pyrazine-6-carbohydrazonamide

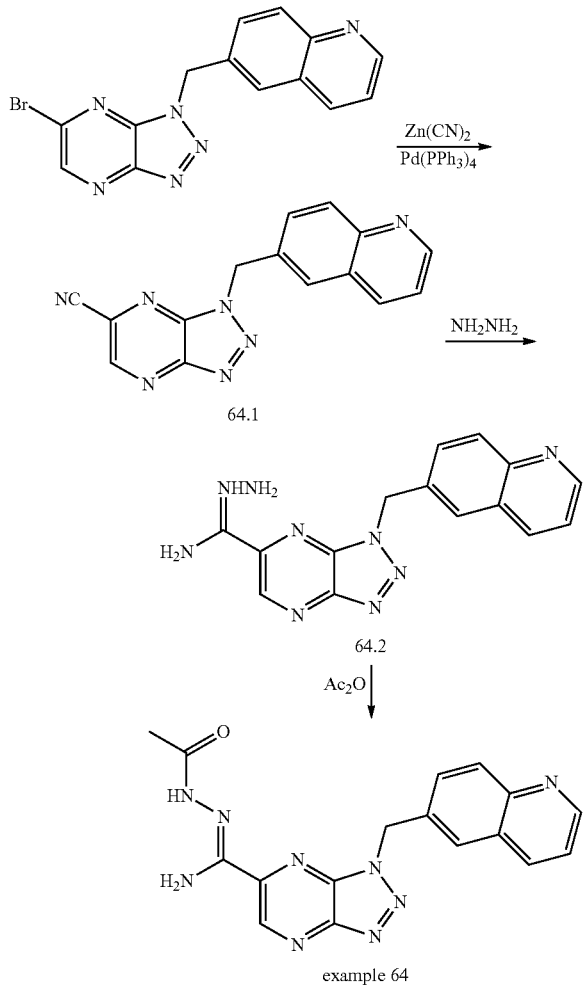

1-(Quinolin-6-ylmethyl)-1H-[1,2,3]triazolo[4,5-b]pyrazine-6-carbonitrile (64.1)

To a degassed solution of 6-((6-bromo-1H-[1,2,3]triazolo[4,5-b]pyrazin-1-yl)methyl)quinoline (1.6 g, 4.69 mmol) in DMF (8 mL), was added Pd(PPh$_3$)$_4$ (0.434 g, 0.375 mmol) and dicyanozinc (0.441 g, 3.75 mmol). The reaction mixture was heated to 127° C. for 4 h. NH$_4$Cl(aq) was added to quench the reaction, followed by EtOAc. The reaction mixture was filtered through celite, washed with saturated NaHCO$_3$ and NH$_4$Cl. The organic layer was separated, dried over Na$_2$SO$_4$, filtered and concentrated to give a crude product, which was purified with Analogix gel silica (Hexanes:EtOAc) to afford the title compound as a light yellow solid. LCMS (method B): [MH]$^+$=288, $t_R$=1.81 min.

1-(Quinolin-6-ylmethyl)-1H-[1,2,3]triazolo[4,5-b]pyrazine-6-carbohydrazonamide (64.2)

To a solution of 1-(quinolin-6-ylmethyl)-1H-[1,2,3]triazolo[4,5-b]pyrazine-6-carbonitrile (80 mg, 0.278 mmol) in EtOH (3 mL), was added hydrazine hydrate (18.12 mg, 0.362 mmol). The reaction was heated to 60° C. overnight. The mixture was filtered and washed with EtOH, H$_2$O, and EtOH to give a yellow solid. $^1$H-NMR (400 MHz, DMSO-d$_6$+D$_2$O) δ ppm 9.29 (s, 1H), 8.88 (s, 1H), 8.34 (d, 1H), 8.01 (m, 2H), 7.83 (d, 1H), 7.52 (m, 1H), 6.16 (s, 2H). LCMS (method B): [MH]$^+$=320, $t_R$=1.03 min.

((E)-N'-Acetyl-1-(quinolin-6-ylmethyl)-1H-[1,2,3]triazolo[4,5-b]pyrazine-6-carbohydrazonamide (Example 64)

To a solution of 1-(quinolin-6-ylmethyl)-1H-[1,2,3]triazolo[4,5-b]pyrazine-6-carbohydrazonamide (25 mg, 0.078 mmol) in DMSO (1 mL) and DCM (2.0 mL), was added pyridine (6.19 mg, 0.078 mmol) and acetic anhydride (10.39 mg, 0.102 mmol). After stirring overnight, the reaction mixture was filtered. The solid was washed with EtOH, H$_2$O and EtOH to give 19.9 mg of title compound in 67% yield. $^1$H-NMR (400 MHz, DMSO-d$_6$) δ ppm 9.48 (d, 1H), 8.88 (d, 1H), 8.34 (d, 1H), 8.05 (s, 1H), 8.01 (d, 1H), 7.86 (d, 1H), 7.53 (dd, 1H), 6.20 (s, 2H), 2.24 (s, 1H), 2.00 (s, 1H). LCMS (method B): [MH]$^+$=362, $t_R$=1.60 min.

Example 65

(E)-2-(Amino(1-(quinolin-6-ylmethyl)-1H-[1,2,3]triazolo[4,5-b]pyrazin-6-yl)methylene)hydrazinecarboxamide

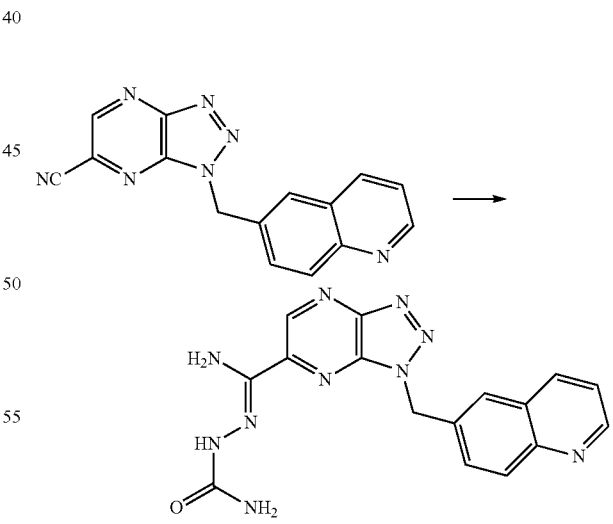

The title compound was prepared in analogy to the synthesis of compound 64.2 from 1-(quinolin-6-ylmethyl)-1H-[1,2,3]triazolo[4,5-b]pyrazine-6-carbonitrile and hydrazinecarbox-amide hydrochloride. $^1$H-NMR (400 MHz, DMSO-d$_6$) δ ppm 9.80 (s, 1H), 8.88 (m, 1H), 8.34 (d, 1H), 8.05 (d, 1H), 8.00 (d, 1H), 7.86 (d, 1H), 7.52 (dd, 1H), 6.18 (s, 2H). LCMS (method B): [MH]$^+$=363, $t_R$=1.70 min.

Example 66

(E)-2-((1-(Quinolin-6-ylmethyl)-1H-[1,2,3]triazolo[4,5-b]pyrazin-6-yl)methylene)-hydrazinecarboxamide

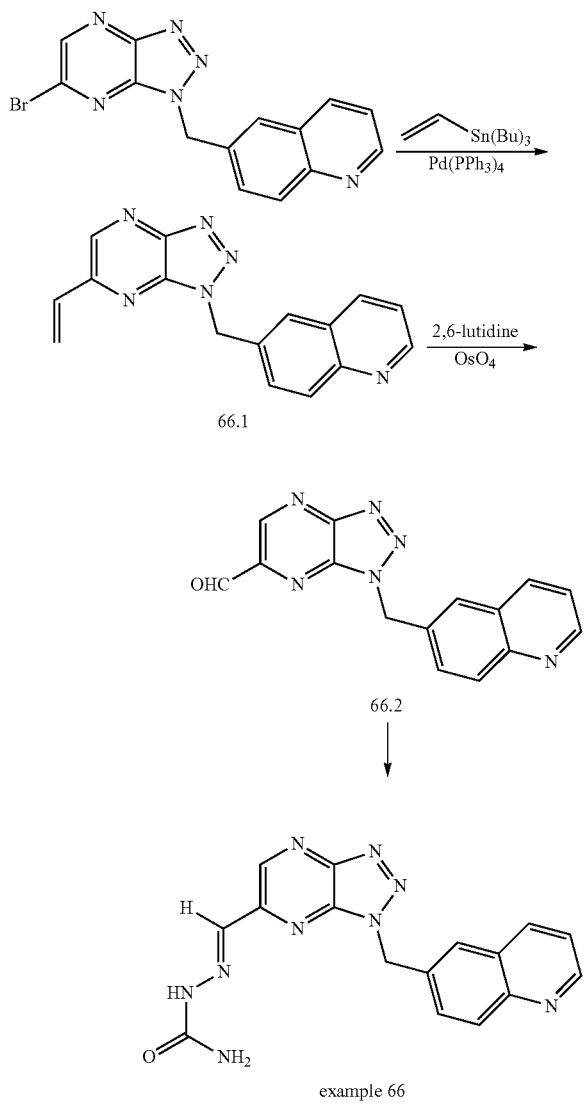

example 66

6-((6-Vinyl-1H-[1,2,3]triazolo[4,5-b]pyrazin-1-yl)methyl)quinoline (66.1)

To a degassed solution 6-((6-bromo-1H-[1,2,3]triazolo[4,5-b]pyrazin-1-yl)methyl)quinoline (1200 mg, 3.52 mmol) in DMF (10 mL), was added Pd(PPh$_3$)$_4$ (610 mg, 0.528 mmol). The solution was stirred for 20 min, then tributyl(vinyl)stannane (1227 mg, 3.87 mmol) was added. The reaction mixture was heated to 120° C. for 5 h. NH$_4$Cl(aq) was added to quench the reaction, followed by EtOAc. The reaction mixture was filtered through celite and the filtrate was washed with sat NaHCO$_3$, sat NH$_4$Cl. The organic layer was separated, dried over Na$_2$SO$_4$ and concentrated to give the crude product, which was purified with Analogix gel silica (Hexanes:EA) to afford 210 mg of title compound in 20% yield. LCMS (method B): [MH]$^+$=288, $t_R$=2.05 min.

1-(Quinolin-6-ylmethyl)-1H-[1,2,3]triazolo[4,5-b]pyrazine-6-carbaldehyde (66.2)

To a mixture of 6-((6-vinyl-1H-[1,2,3]triazolo[4,5-b]pyrazin-1-yl)methyl)quinoline (100 mg, 0.347 mmol) and 2,6-dimethylpyridine (74.3 mg, 0.694 mmol), was added a solution of osmium(VIII) oxide (297 mg, 1.387 mmol) in H$_2$O (1.333 mL), followed by a solution of sodium periodate (88 mg, 6.94 μmol) in 1,4-Dioxane (4 ml). The reaction mixture was stirred at rt for 10 h. The solvents was removed in vacuo and DCM was added to dilute the residue. The resulting solution was washed with saturated NaHCO$_3$, NH$_4$Cl and brine. The organic layer was separated, dried over Na$_2$SO$_4$, and concentrated to give a crude product, which was purified with Analogix gel silica (Hexanes:EA) to afford 45 mg of title compound in 43% yield. LCMS (method B): [MH]$^+$=291, $t_R$=1.00 min.

(E)-2-((1-(Quinolin-6-ylmethyl)-1H-[1,2,3]triazolo[4,5-b]pyrazin-6-yl)methylene) hydrazinecarboxamide (Example 66)

The title compound was prepared in 65% yield in analogy to the synthesis of compound of 52 from 1-(quinolin-6-ylmethyl)-1H-[1,2,3]triazolo[4,5-b]pyrazine-6-carbaldehyde. $^1$H-NMR (400 MHz, DMSO-d$_6$) δ ppm 9.68 (s, 1H), 8.88 (m, 1H), 8.33 (m, 1H), 7.99 (m, 2H), 7.91 (s, 1H), 7.76 (m, 1H), 7.52 (dd, 1H), 6.16 (s, 2H). LCMS (method B): [MH]$^+$=348, $t_R$=1.60 min.

Example 67

(E)-2-(1-(1-(1-(7-Fluoroquinolin-6-yl)ethyl)-1H-[1,2,3]triazolo[4,5-b]pyrazin-6-yl)ethylidene)hydrazinecarboxamide

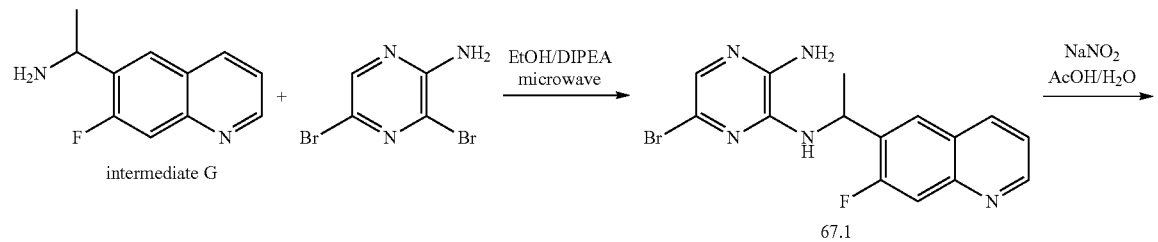

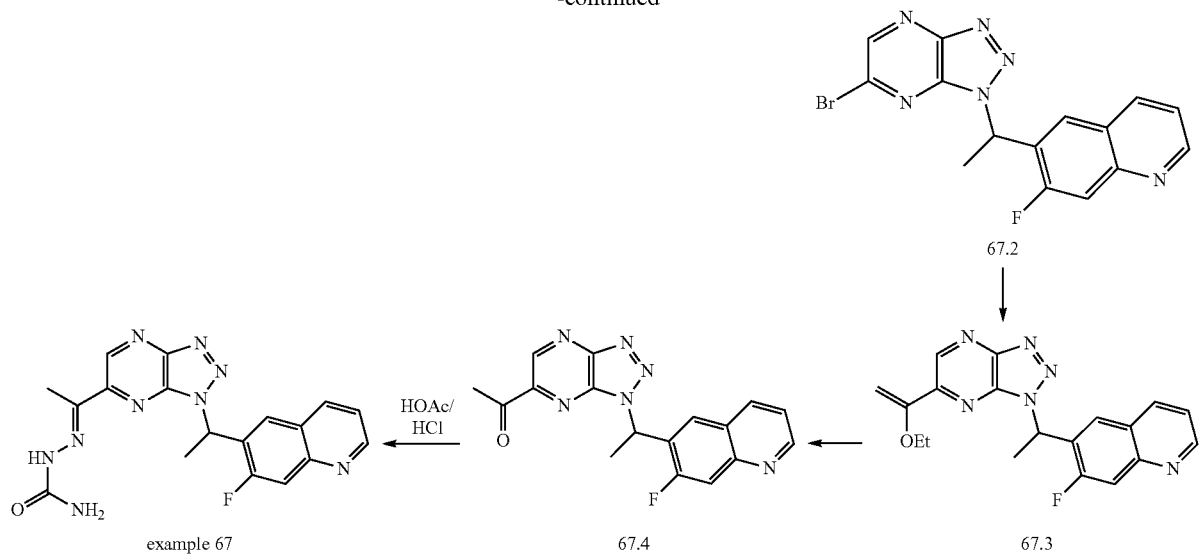

6-Bromo-N2-(1-(7-fluoroquinolin-6-yl)ethyl)pyrazine-2,3-diamine (67.1)

The title compound was prepared as a white solid from 1-(7-fluoroquinolin-6-yl)ethanamine in analogy to the synthesis of compound 52.1. LCMS (method B): [MH]⁺=364, $t_R$=2.38 min.

6-(1-(6-Bromo-1H-[1,2,3]triazolo[4,5-b]pyrazin-1-yl)ethyl)-7-fluoroquinoline (67.1)

The title compound was prepared from 6-bromo-N2-(1-(7-fluoroquinolin-6-yl)ethyl)pyrazine-2,3-diamine in analogy to the synthesis of compound 52.2. LCMS (method B): [MH]⁺=345, $t_R$=2.36 min.

6-(1-(6-(1-Ethoxyvinyl)-1H-[1,2,3]triazolo[4,5-b]pyrazin-1-yl)ethyl)-7-fluoroquinoline (67.3)

The title compound was prepared in analogy to the synthesis of compound 52.3 from 6-(1-(6-bromo-1H-[1,2,3]triazolo[4,5-b]pyrazin-1-yl)ethyl)-7-fluoroquinoline. ¹H-NMR (400 MHz, CDCl₃) δ ppm 9.17 (9.17 (s, 1H), 8.90 (m, 1H), 8.10 (d, 1H), 7.89 (d, 1H), 7.78 (d, 1H), 7.39 (dd, 1H), 6.82 (q, 1H), 5.56 (d, 1H), 4.56 (d, 1H), 4.04 (q, 2H), 2.30 (d, 3H), 1.48 (t, 3H). LCMS (method B): [MH]⁺=365, $t_R$=2.55 min.

1-(1-(1-(7-Fluoroquinolin-6-yl)ethyl)-1H-[1,2,3]triazolo[4,5-b]pyrazin-6-yl)ethanone (67.4)

The title compound was prepared in analogy to the synthesis of compound of 52.4 from 6-(1-(6-(1-ethoxyvinyl)-1H-[1,2,3]triazolo[4,5-b]pyrazin-1-yl)ethyl)-7-fluoroquinoline. ¹H-NMR (400 MHz, CDCl₃) δ ppm 9.44 (s, 1H), 8.93 (m, 1H), 8.13 (d, 1H), 7.94 (s, 1H) 7.79 (d, 1H), 7.41 (dd, 1H), 6.88 (q, 1H), 2.76 (s, 3H), 2.37 (d, 3H). LCMS (method B): [MH]⁺=337, $t_R$=2.21 min.

(E)-2-(1-(1-(1-(7-Fluoroquinolin-6-yl)ethyl)-1H-[1,2,3]triazolo[4,5-b]pyrazin-6-yl)ethylidene)hydrazinecarboxamide (Example 67)

The title compound was prepared in analogy to the synthesis of example 52 from 1-(1-(1-(7-fluoroquinolin-6-yl)ethyl)-1H-[1,2,3]triazolo[4,5-b]pyrazin-6-yl)ethanone. ¹H-NMR (400 MHz, DMSO-d₆) δ ppm 9.69 (s, 1H), 8.89 (d, 1H), 8.43 (d, 1H), 8.22 (d, 1H), 7.73 (d, 1H), 7.55 (dd, 1H), 8.86 (q, 1H), 2.34 (d, 3H), 2.31 (s, 3H). LCMS (method B): [MH]⁺=394, $t_R$=2.13 min.

Example 68

(E)-2-(1-(3-((6-Fluoro-1-methyl-1H-indazol-5-yl)ethyl)imidazo[1,2-b]pyridazin-6-yl)ethylidene)hydrazinecarboxamide

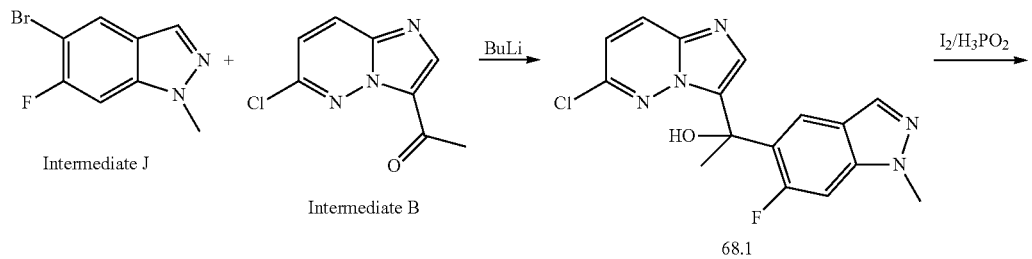

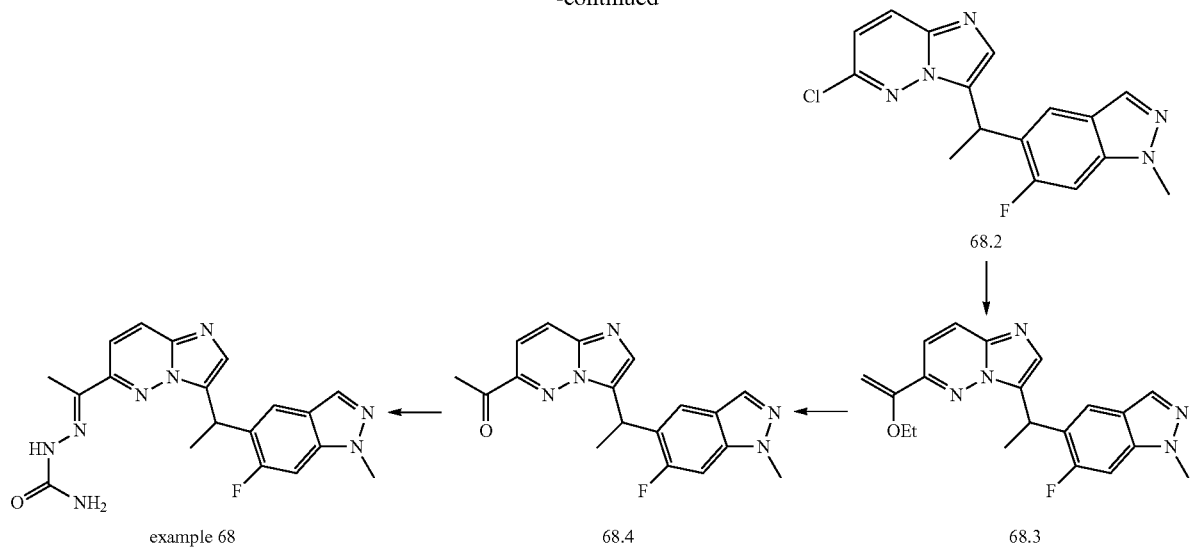

example 68            68.4            68.3

1-(6-Chloroimidazo[1,2-b]pyridazin-3-yl)-1-(6-fluoro-1-methyl-1H-indazol-5-yl)ethanol (68.1)

To a solution of 5-bromo-6-fluoro-1-methyl-1H-indazole (1.800 g, 7.86 mmol) in THF (79 ml) at −100° C., was added n-BuLi (5.40 ml, 8.64 mmol) dropwise. After stirring for 1 h at −100° C., 1-(6-chloroimidazo[1,2-b]pyridazin-3-yl)ethanone (1.691 g, 8.64 mmol) in THF (20 mL) was added dropwise. The reaction solution was stirred for additional 2 h and was quenched with NH$_4$Cl (aq). The resulting mixture was extracted with EtOAc. Combined organic layers were washed with NH$_4$Cl(aq), dried over Na$_2$SO$_4$ and concentrated in vacuo to afford a crude product, which was purified on silica gel column chromatography (Hexanes:EtOAc) to give the title compound in 34% yield. LCMS (method B): [MH]$^+$= 346, $t_R$=2.14 min.

6-Chloro-3-(1-(6-fluoro-1-methyl-1H-indazol-5-yl)ethyl)imidazo[1,2-b]pyridazine (68.2)

A mixture of 1-(6-chloroimidazo[1,2-b]pyridazin-3-yl)-1-(6-fluoro-1-methyl-1H-indazol-5-yl)ethanol (1.1 g, 3.18 mmol), diiodine (2.019 g, 7.95 mmol), and phosphinic acid (0.840 g, 12.73 mmol) in HOAc (10 ml) was heated to 120° C. for 5 h. After cooling to rt, the reaction mixture was concentrated in vacuo. The residue was taken with water and adjusted its pH tp 8 with aqueous NaOH. The mixture was extracted with DCM, dried over Na$_2$SO$_4$ and concentrated to give a residue, which was purified with silica gel column chromatography (MeOH:EA) to give 6-chloro-3-(1-(6-fluoro-1-methyl-1H-indazol-5-yl)ethyl)imidazo[1,2-b]pyridazine (900 mg 60%). LCMS (method B): [MH]$^+$=330, $t_R$=2.59 min.

6-(1-Ethoxyvinyl)-3-(1-(6-fluoro-1-methyl-1H-indazol-5-yl)ethyl)imidazo[1,2-b]pyridazine (68.3)

To a solution of 6-chloro-3-(1-(6-fluoro-1-methyl-1H-indazol-5-yl)ethyl)imidazo[1,2-b]pyridazine (900 mg, 1.910 mmol) in DMF (8 mL), was added Pd(Ph$_3$P)$_4$ (221 mg, 0.191 mmol). The mixture was stirred for 20 min, and tributyl(1-ethoxyvinyl)stannane (784 mg, 2.102 mmol) was added. The resulting mixture was heated to 100° C. until the LC-MS showed the reaction was complete. The reaction mixture was filtered through celite and the solid was washed with ether. The filtration was then washed with water, dried over Na$_2$SO$_4$, and concentrated to a residue, which was purified by silica gel column chromatography with gradient Hex:EA to give 6-(1-ethoxyvinyl)-3-(1-(6-fluoro-1-methyl-1H-indazol-5-yl)ethyl)imidazo[1,2-b]pyridazine (450 mg, 52%).

1-(3-(1-(6-Fluoro-1-methyl-1H-indazol-5-yl)ethyl)imidazo[1,2-b]pyridazin-6-yl)ethanone (68.4)

To a solution of the 6-(1-ethoxyvinyl)-3-(1-(6-fluoro-1-methyl-1H-indazol-5-yl)ethyl)-imidazo[1,2-b]pyridazine (450 mg, 0.985 mmol) in acetic acid (8 mL), was added 3N HCl (0.5 mL). The solution was stirred at rt for 2 h and the solvents were removed under reduced pressure. The residue was diluted with water and its pH was adjusted to basic with aqueous NaHCO$_3$, extracted with DCM. The organic layer was washed with NaHCO$_3$(aq) and brine, dried over Na$_2$SO$_4$, and concentrated in vacuo. The residue was purified by silica gel column chromatography to give yellow solid 1-(3-(1-(6-fluoro-1-methyl-1H-indazol-5-yl)ethyl)imidazo[1,2-b]pyridazin-6-yl)ethanone (300 mg, 81%). LCMS (method B): [MH]$^+$=338, $t_R$=2.49 min.

(E)-2-(1-(3-(1-(6-Fluoro-1-methyl-1H-indazol-5-yl)ethyl)imidazo[1,2-b]pyridazin-6-yl)ethylidene)hydrazinecarboxamide (Example 68)

To a solution of 1-(3-(1-(6-fluoro-1-methyl-1H-indazol-5-yl)ethyl)imidazo[1,2-b]pyridazin-6-yl)ethanone (35 mg, 0.104 mmol) in MeOH (4 mL), was added hydrazinecarboxamide hydrochloride (28.9 mg, 0.259 mmol). The reaction mixture was heated to 35° C. After stirring for 5 h, the solvent was removed and DCM was added to dilute the residue. The resulting mixture was then washed with brine, dried over Na$_2$SO$_4$, and concentrated in vacuo to give (E)-2-(1-(3-(1-(6-fluoro-1-methyl-1H-indazol-5-yl)ethyl)imidazo[1,2-b]pyridazin-6-yl)ethylidene)hydrazinecarboxamide (14 mg, 33%) as a white solid. $^1$H-NMR (400 MHz, DMSO-d$_6$) δ ppm 9.64 (s, 1H), 8.14 (d, 1H), 7.93 (m, 2H), 7.74 (s, 1H), 7.51 (m, 2H), 4.93 (m, 1H), 3.96 (s, 3H), 2.13 (s, 3H), 1.76 (d, 3H). LCMS (method B): [MH]$^+$=395, $t_R$=2.32 min.

Example 69

(E)-2-(1-(3-((6-Fluoro-1-methyl-1H-indazol-5-yl)methyl)imidazo[1,2-b]pyridazin-6-yl)ethylidene)hydrazinecarboxamide

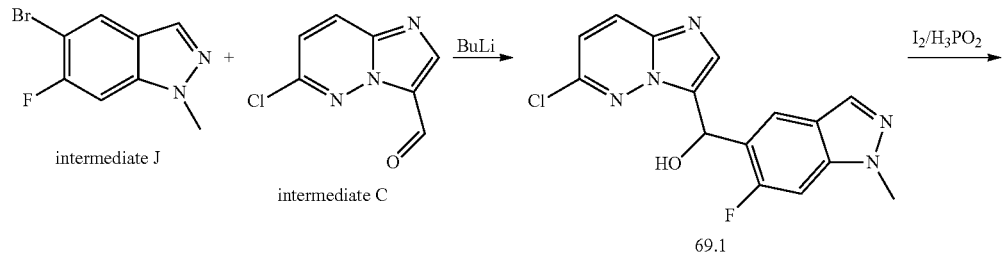

6-(1-Ethoxyvinyl)-3-((6-fluoro-1-methyl-1H-indazol-5-yl)methyl)imidazo[1,2-b]pyridazine (67.3)

The title compound was prepared in analogy to the synthesis of compound 68.3 from 6-chloro-3-((6-fluoro-1-methyl-1H-indazol-5-yl)methyl)imidazo[1,2-b]pyridazine.

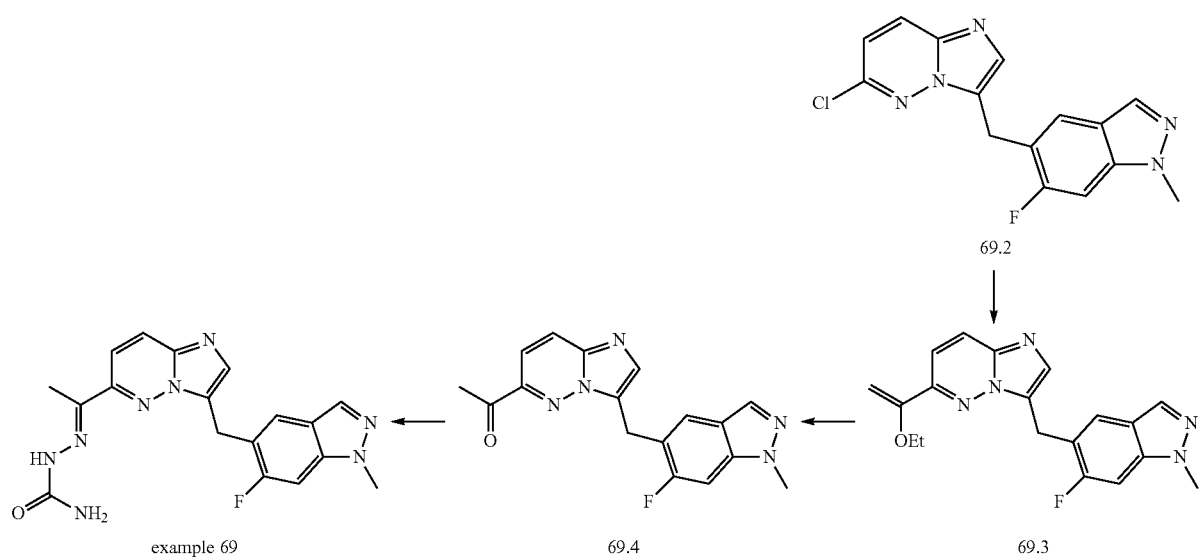

6-Chloroimidazo[1,2-b]pyridazin-3-yl)(6-fluoro-1-methyl-1H-indazol-5-yl)methanol (69.1)

The title compound was prepared as a yellow solid in analogy to the synthesis of compound 68.1 from 6-chloroimidazo[1,2-b]pyridazine-3-carbaldehyde. LCMS (method B): [MH]$^+$=332, $t_R$=2.09 min.

6-Chloro-3-((6-fluoro-1-methyl-1H-indazol-5-yl)methyl)imidazo[1,2-b]pyridazine (69.2)

The title compound was prepared as a yellow solid in analogy to the synthesis of compound 68.2 from (6-chloroimidazo[1,2-b]pyridazin-3-yl)(6-fluoro-1-methyl-1H-indazol-5-yl)methanol. LCMS (method B): [MH]$^+$=316, $t_R$=2.56 min.

1-(3-((6-Fluoro-1-methyl-1H-indazol-5-yl)methyl)imidazo[1,2-b]pyridazin-6-yl)ethanone (67.4)

The title compound was prepared as a white solid in analogy to the synthesis of compound 68.4 from 6-(1-ethoxyvinyl)-3-((6-fluoro-1-methyl-1H-indazol-5-yl)methyl)imidazo[1,2-b]pyridazine. LCMS (method B): [MH]$^+$=324, $t_R$=2.41 min.

(E)-2-(1-(3-((6-Fluoro-1-methyl-1H-indazol-5-yl)methyl)imidazo[1,2-b]pyridazin-6-yl)ethylidene)hydrazinecarboxamide (Example 67)

The title compound was prepared as a white solid in analogy to the synthesis of example 68 from 1-(3-((6-fluoro-1-methyl-1H-indazol-5-yl)methyl)imidazo[1,2-b]pyridazin-6-yl)ethanone. $^1$H-NMR (400 MHz, DMSO-d$_6$) δ ppm 9.71 (s, 1H), 8.19 (s, 1H), 7.96 (m, 2H), 7.69 (d, 1H), 7.55 (s, 1H), 7.54 (d, 1H), 4.41 (s, 2H), 3.97 (s, 3H), 2.28 (s, 3H). LCMS (method B): [MH]$^+$=381, $t_R$=2.20 min.

Example 70

(E)-2-(1-(3-((1-Methyl-1H-indazol-5-yl)methyl) imidazo[1,2-b]pyridazin-6-yl)ethylidene) hydrazinecarboxamide

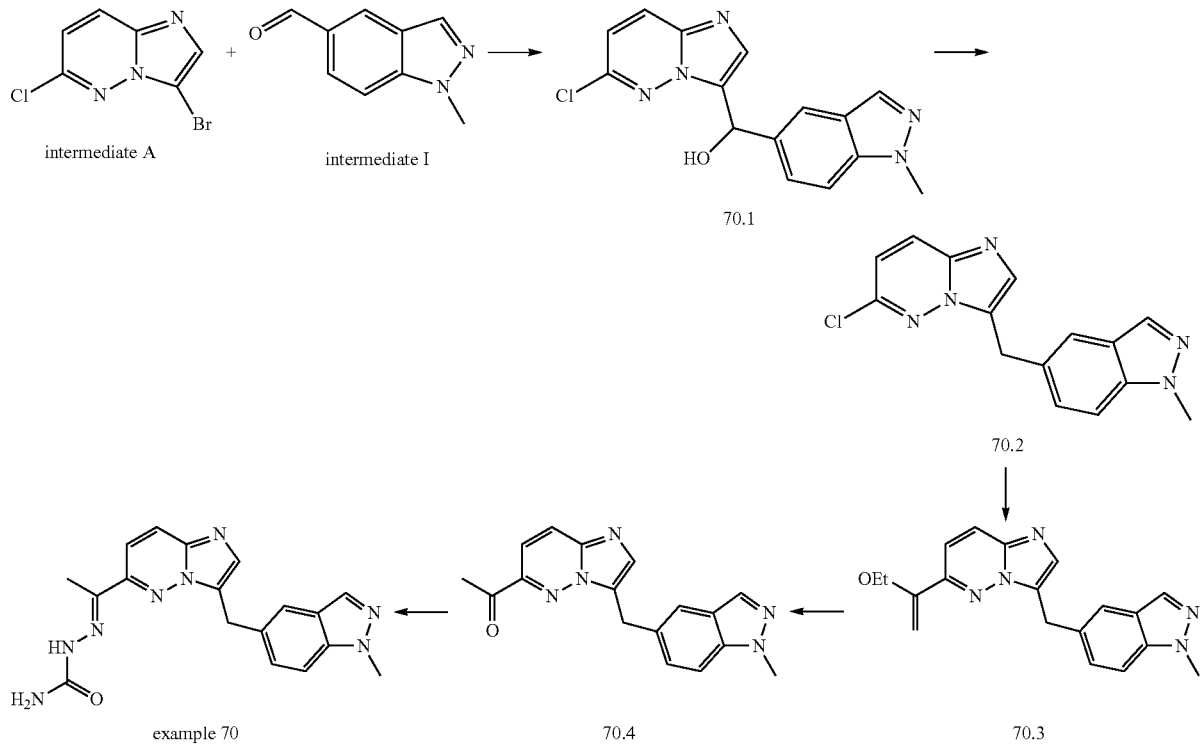

(6-Chloroimidazo[1,2-b]pyridazin-3-yl)(1-methyl-1H-indazol-5-yl)methanol (70.1)

To a solution of 3-bromo-6-chloroimidazo[1,2-b]pyridazine (232.0 mg, 1.00 mmol) in 5 mL THF, was added ethylmagnesium bromide (1.50 mL, 1.50 mmol) at −10° C. After stirring at −10° C. for 1 hour, 1-methyl-1H-indazole-5-carbaldehyde (240.0 mg, 1.50 mmol) was added. The mixture was allowed to warm to room temperature slowly and stirred for additional 2 hours. The reaction was quenched with Sat. NH₄Cl solution and concentrated under reduced pressure. The residue was diluted with water, and extracted with EtOAc twice. The organic layers were combined, dried over Na₂SO₄ and concentrated. The crude product was washed with DCM to give the title compound as a white solid (230 mg, 70%). $^1$H-NMR (400 MHz, DMSO-d₆) δ ppm 8.21 (d, 1H), 8.02 (s, 1H), 7.81 (s, 1H), 7.59 (d, 1H), 7.56 (s, 1H), 7.49 (d, 1H), 7.35 (d, 1H), 6.29 (d, 1H), 6.21 (d, 1H), 4.02 (s, 3H). LCMS (method A): [MH]⁺=314, $t_R$=4.44 min

6-Chloro-3-((1-methyl-1H-indazol-5-yl)methyl)imidazo[1,2-b]pyridazine (70.2)

A solution of (6-chloroimidazo[1,2-b]pyridazin-3-yl)(1-methyl-1H-indazol-5-yl)methanol (156.8 mg, 0.50 mmol), I₂ (381 mg, 1.50 mmol) and H₃PO₂ (0.273 mL, 2.50 mmol) in 4 mL AcOH was heated at 110° C. for 7 hours. The solvent was removed under reduced pressure. The residue was diluted with water and extracted with DCM twice. The organic layers were combined, dried over Na₂SO₄ and concentrated. The crude product was purified by flash chromatography (DCM:MeOH=20:1) to give the title compound which contains some iodine and used in the next step without further purification (180.0 mg, 44%, 36% pure). LCMS (method A): [MH]⁺=298, $t_R$=5.37 min

6-(1-Ethoxy-vinyl)-3-(1-methyl-1H-indazol-5-ylmethyl)-imidazo[1,2-b]pyridazine (70.3)

A suspension of 6-chloro-3-((1-methyl-1H-indazol-5-yl)methyl)imidazo[1,2-b]pyridazine (180.0 mg, 36% pure, 0.22 mmol), tributyl(1-ethoxyvinyl)stannane (94 mg, 0.26 mmol) and Pd(PPh₃)₄ (25.1 mg, 0.02 mmol) in 10 mL DMF was flashed with nitrogen, then heated at 110° C. and stirred overnight. Solvent was removed under reduced pressure, the residue was diluted with DCM, washed sequentially with KF solution and water. The organic layer was dried over Na₂SO₄, filtered and concentrated in vacuo. The crude product was purified by flash chromatography (DCM:MeOH=20:1) to give the title compound which contains some triphenylphosphine oxide impurity and used in the next step without further purification (49 mg, 47%, 70% pure). LCMS (method A): [MH]⁺=334, $t_R$=5.71 min.

1-(3-((1-Methyl-1H-indazol-5-yl)methyl)imidazo[1,2-b]pyridazin-6-yl)ethanone (70.4)

A solution of 6-(1-ethoxy-vinyl)-3-(1-methyl-1H-indazol-5-ylmethyl)-imidazo[1,2-b]pyridazine (50 mg, 0.15 mmol) and HCl (0.15 mL, 0.15 mmol) in 10 mL AcOH was heated at 50° C. for 3 hour. The solvent was removed under reduced pressure. The residue was diluted with water and adjusted the pH value of solution to around 8 with aqueous NaHCO₃, extracted with DCM three times. Organic layers were combined, dried over Na₂SO₄ and concentrated. The crude product was used in the next step without purification (45 mg, 75%, 76% pure). LCMS (method A): [MH]⁺=306, $t_R$=5.03 min.

(E)-2-(1-(3-((1-Methyl-1H-indazol-5-yl)methyl) imidazo[1,2-b]pyridazin-6-yl)ethylidene) hydrazinecarboxamide (Example 70)

A solution of 1-(3-((1-methyl-1H-indazol-5-yl)methyl) imidazo[1,2-b]pyridazin-6-yl)ethanone (40.0 mg, 0.09 mmol) and hydrazinecarboxamide (19.47 mg, 0.26 mmol) in 10 mL THF was stirred at 40° C. for overnight. Solvent was removed in vacuo. The crude product was purified on flash chromatography (DCM:MeOH=20:1) to give the title compound as a white solid (29.0 mg, 88%). ¹H-NMR (400 MHz, DMSO-$d_6$) δ ppm 9.71 (s, 1H), 8.18 (d, 1H), 7.95 (m, 2H), 7.69 (s, 1H), 7.60 (s, 1H), 7.75 (d, 1H), 7.40 (dd, 1H), 6.76 (bs, 2H), 4.41 (s, 2H), 3.99 (s, 3H), 2.29 (s, 3H). LCMS (method A): [MH]⁺=363, $t_R$=4.42 min.

Example 71

(E)-2-(1-(3-(1-(1-Methyl-1H-indazol-5-yl)ethyl) imidazo[1,2-b]pyridazin-6-yl)ethylidene) hydrazinecarboxamide adjusted to around 10 with 10% aqueous NaOH. The precipitates were collected by filtration and washed with water three times. The solid was dissolved in DCM, dried over Na₂SO₄, filtered and concentrated to give the title compound as a white solid (410.0 mg, 78%). ¹H-NMR (400 MHz, DMSO-$d_6$) δ ppm 8.46 (s, 1H), 8.42 (m, 1H), 8.32 (m, 1H), 8.27 (d, 1H), 7.95 (dd, 1H), 7.815 (d, 1H), 7.66 (d, 1H), 4.12 (s, 2H). LCMS (method A): [MH]⁺=312, $t_R$=4.64 min.

1-(6-Chloro-imidazo[1,2-b]pyridazin-3-yl)-1-(1-methyl-1H-indazol-5-yl)-ethanol (71.2)

To a solution of (6-chloroimidazo[1,2-b]pyridazin-3-yl) (1-methyl-1H-indazol-5-yl)methanone (410 mg, 1.32 mmol) in 10 mL THF was added methylmagnesium iodide (0.88 mL, 2.63 mmol) at 0° C. After stirring at 0° C. for 3 hour, the reaction was quenched with saturated NH₄Cl and concentrated under resdue pressure. The residue was extracted with DCM three times. The organic layers were combined, dried over Na₂SO₄ and concentrated to give the title compound as a white solid (430.0 mg, 95%). ¹H-NMR (400 MHz, DMSO-$d_6$) δ ppm 8.17 (d, 1H), 7.99 (s, 1H), 7.50 (m, 1H), 7.40 (d, 1H), 7.25 (d, 1H), 5.98 (s, 1H), 3.99 (s, 3H), 2.05 (s, 3H). LCMS (method A): [MH]⁺=328, $t_R$=4.55 min.

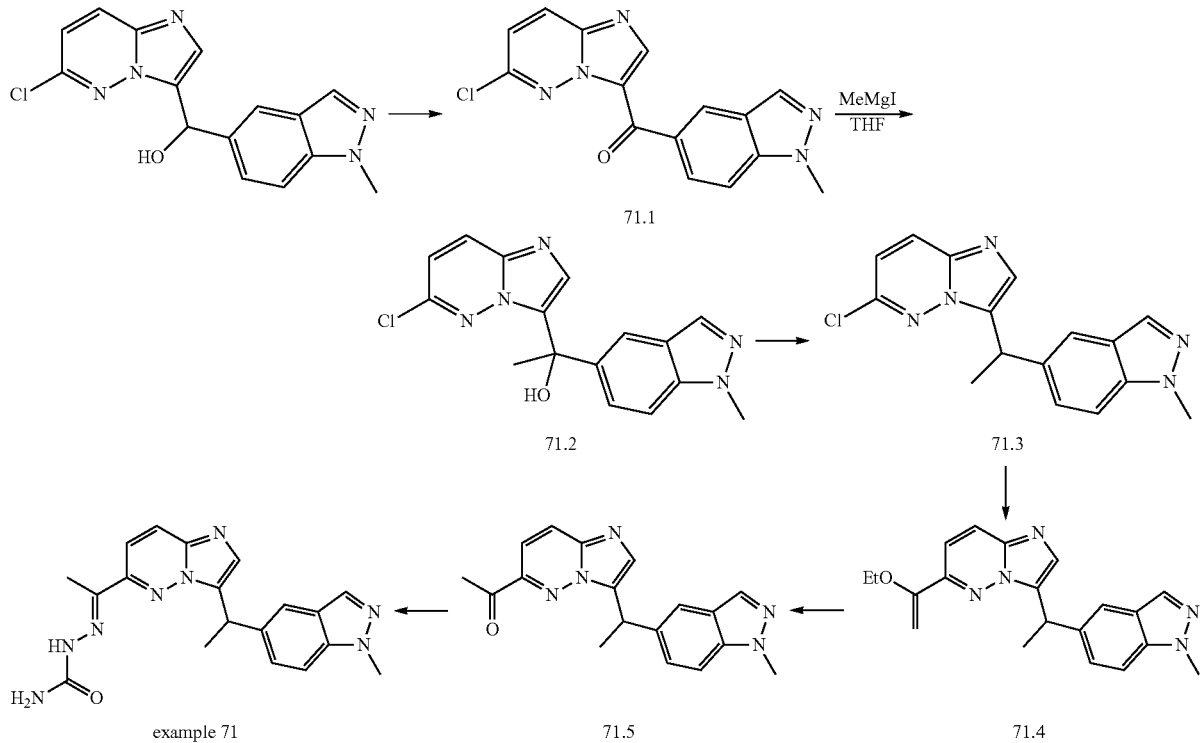

(6-Chloroimidazo[1,2-b]pyridazin-3-yl)(1-methyl-1H-indazol-5-yl)methanone (71.1)

A suspension of (6-chloroimidazo[1,2-b]pyridazin-3-yl) (1-methyl-1H-indazol-5-yl)methanol (500.0 mg, 1.60 mmol) and 2-Iodoxybenzoic acid (45% pure, 1488.0 mg, 2.39 mmol) in 10 mL acetone was heated at refluxe and stirred for 3 hours. Solvent was removed under reduced pressure. The residue was diluted with water, and the pH value of the solution

6-Chloro-3-[1-(1-methyl-1H-indazol-5-yl)-ethyl]-imidazo[1,2-b]pyridazine (71.3)

The title compound (390.0 mg, 91%) was synthesized from 1-(6-chloro-imidazo[1,2-b]pyridazin-3-yl)-1-(1-methyl-1H-indazol-5-yl)-ethanol (430.0 mg, 1.31 mmol), I₂ (832.0 mg, 3.28 mmol) and H₃PO₂ (0.72 mL, 6.56 mmol) using the same procedure as described in the synthesis of compound 69.2. ¹H-NMR (400 MHz, DMSO-$d_6$) δ ppm 8.18 (d, 1H), 7.95 (s, 1H), 7.83 (s, 1H), 7.55 (m, 2H), 7.36 (d, 1H), 7.28 (d, 1H), 4.70 (q, 1H), 3.99 (s, 3H), 1.74 (d, 3H). LCMS (method A): [MH]$^+$=312, $t_R$=5.49 min.

6-(1-Ethoxy-vinyl)-3-[1-(1-methyl-1H-indazol-5-yl)-ethyl]-imidazo[1,2-b]pyridazine (71.4)

The title compound (415.0 mg, 86%, 90% pure) was synthesized from 6-chloro-3-[1-(1-methyl-1H-indazol-5-yl)-ethyl]-imidazo[1,2-b]pyridazine (390.0 mg, 1.25 mmol), tributyl(1-ethoxyvinyl)stannane (497.0 mg, 1.38 mmol) and Pd(PPh$_3$)$_4$ (145 mg, 0.13 mmol) using the same procedure as described in the synthesis of compound 69.3. LCMS (method A): [MH]$^+$=348, $t_R$=5.86 min.

ecarboxamide (13.97 mg, 0.13 mmol) using the same procedure as described in the synthesis of example 69. $^1$H-NMR (400 MHz, CDCl$_3$) δ ppm 8.33 (s, 1H), 7.87 (m, 2H), 7.66 (m, 3H), 7.32 (m, 2H), 4.74 (q, 1H), 4.03 (s, 3H), 2.24 (s, 3H), 1.84 (d, 3H). LCMS (method A): [MH]$^+$=377, $t_R$=4.70 min.

Example 72

(E)-2-(1-(1-((7-Fluoroquinolin-6-yl)methyl)-1H-[1,2,3]triazolo[4,5-b]pyrazin-6-yl)ethyl idene)hydrazinecarboxamide

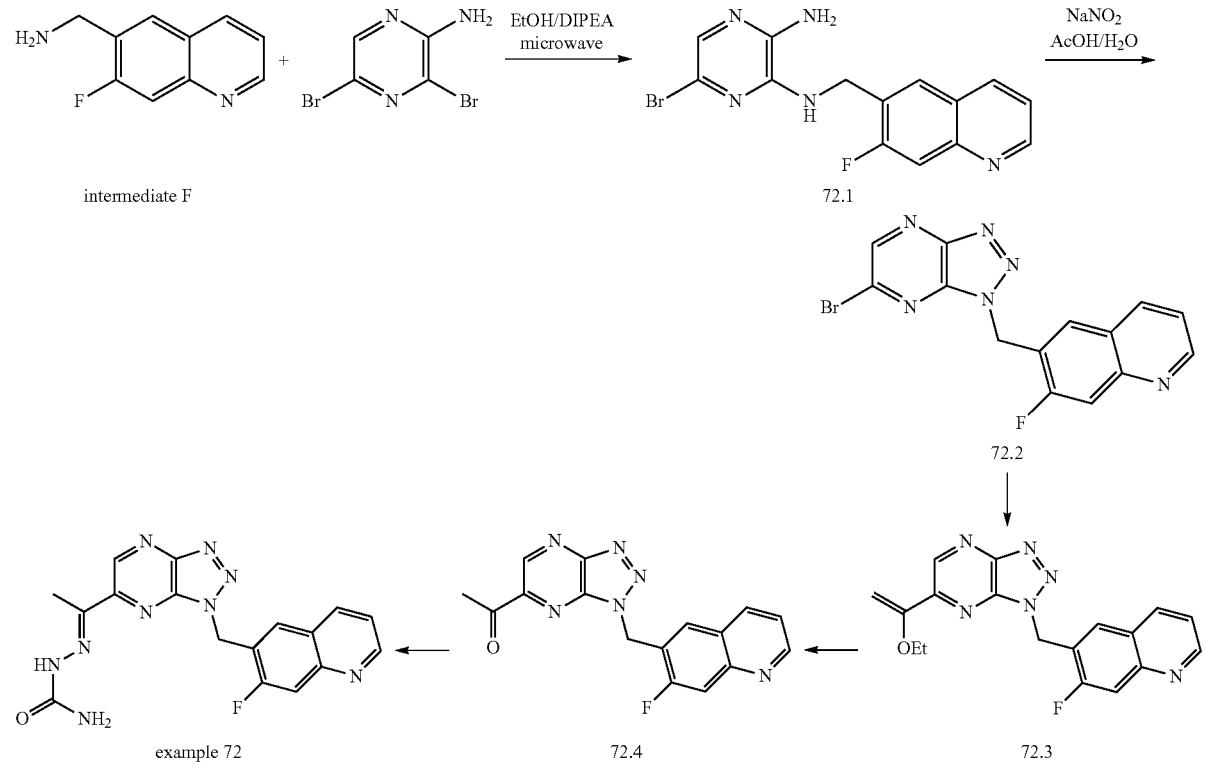

1-(3-(1-(1-Methyl-1H-indazol-5-yl)ethyl)imidazo[1,2-b]pyridazin-6-yl)ethanone (71.5)

The title compound (325.0 mg, 75%, 88% pure) was synthesized from 6-(1-ethoxy-vinyl)-3-[1-(1-methyl-1H-indazol-5-yl)-ethyl]-imidazo[1,2-b]pyridazine (415.0 mg, 1.20 mmol) and HCl (1.20 mL, 1.20 mmol) using the same procedure as described in the synthesis of compound 69.4. LCMS (method A): [MH]$^+$=320, $t_R$=5.21 min.

(E)-2-(1-(3-(1-(1-Methyl-1H-indazol-5-yl)ethyl)imidazo[1,2-b]pyridazin-6-yl)ethylidene) hydrazinecarboxamide (Example 71)

The title compound (14.0 mg, 59%) was synthesized from 1-(3-(1-(1-methyl-1H-indazol-5-yl)ethyl)imidazo[1,2-b]pyridazin-6-yl)ethanone (20.0 mg, 0.06 mmol) and hydrazin-

5-Bromo-N*3*-(7-fluoro-quinolin-6-ylmethyl)-pyrazine-2,3-diamine (72.1)

A mixture of N-(7-fluoro-quinolin-6-yl)-methylamine (1.69 g, 9.63 mmol), 3,5-dibromopyrazin-2-amine (2.43 g, 9.63 mmol) and DIPEA (2.96 g, 22.90 mmol) was heated in a microwave to 120° C. for 10 hour. The reaction was diluted with DCM and water. The organic layer was washed with NH$_4$Cl (aq.), dried over Na$_2$SO$_4$, filtered and concentrated in vacuo. The crude product was purified by silica gel chromatography (DCM:MeOH) to give the title compound as a yellow solid (2.60 g, 69%). LCMS (method E): [MH]$^+$=348/350, $t_R$=5.21 min.

6-(6-Bromo-[1,2,3]triazolo[4,5-b]pyrazin-1-ylmethyl)-7-fluoro-quinoline (72.2)

To a solution of 5-bromo-N*3*-(7-fluoro-quinolin-6-ylmethyl)-pyrazine-2,3-diamine (90 mg, 0.26 mmol) in acetic acid (4 mL), was added a solution of sodium nitrite (11.4 mg, 0.26 mmol) in water (1 mL) at once. After stirring at room temperature for 3 hour, the solvent was removed in vacuo and the residue was diluted with NaHCO$_3$(aq.), extracted with DCM. The organic layer was washed with water, dried over Na$_2$SO$_4$, filtered and concentrated in vacuo. The crude product was purified by silica gel chromatography with (DCM:MeOH=50:1) to give the title compound as a yellow solid (57.0 mg, 61%). $^1$H-NMR (400 MHz, DMSO-d$_6$) δ ppm 9.03 (s, 1H), 8.94 (d, 1H), 8.40 (d, 1H), 8.08 (d, 1H), 7.84 (d, 1H), 7.55 (dd, 1H), 7.53 (dd, 1H), 6.21 (s, 2H). LCMS (method A): [MH]$^+$=359/361, t$_R$=2.23 min.

6-[6-(1-Ethoxy-vinyl)-[1,2,3]triazolo[4,5-b]pyrazin-1-ylmethyl]-7-fluoro-quinoline (72.3)

A mixture of 6-(6-bromo-[1,2,3]triazolo[4,5-b]pyrazin-1-ylmethyl)-7-fluoro-quinoline (2.0 g, 5.57 mmol), Pd(Ph$_3$P)$_4$ (0.64 g, 0.56 mmol) and tributyl(1-ethoxyvinyl)stannane (4.02 g, 11.14 mmol) in DMF (50 mL) was flushed with nitrogen and then heated at 100° C., stirred for 7 hours. Removal of the solvent under reduced pressure, the residue was diluted with DCM, washed sequentially with KF (aq.) and water, dried over Na$_2$SO$_4$ and concentrated in vacuo. The crude product was purified by silica gel column chromatography with gradient (DCM:MeOH=50:1) to give the title compound as a white solid. $^1$H-NMR (400 MHz, DMSO-d$_6$) δ ppm 9.11 (s, 1H), 8.93 (d, 1H), 8.40 (d, 1H), 8.15 (d, 1H), 7.83 (d, 1H), 7.54 (m, 1H), 6.22 (s, 2H), 5.50 (d, 1H), 4.73 (d, 1H), 4.02 (q, 2H), 1.40 (t, 3H). LCMS (method E): [MH]$^+$=351, t$_R$=5.42 min.

1-[3-(7-Fluoro-quinolin-6-ylmethyl)-3H-[1,2,3]triazolo[4,5-b]pyrazin-5-yl]-ethanone (72.4)

A solution of the 6-[6-(1-ethoxy-vinyl)-[1,2,3]triazolo[4,5-b]pyrazin-1-ylmethyl]-7-fluoro-quinoline (600.0 mg, 0.89 mmol) and 3 N HCl (0.1 mL) in acetic acid was stirred at 50° C. for 2 hour. The solvent was removed under reduced pressure. The residue was diluted with water, adjusted the pH value of solution to around 8 with aqueous NaHCO$_3$, extracted with DCM twice. The combined organic layers were washed sequentially with water and brine, dried over Na$_2$SO$_4$, filtered and concentrated in vacuo to give the title compound as a white solid (630 mg, 96%). $^1$H$^1$H-NMR (400 MHz, CDCl$_3$) δ ppm 9.46 (s, 1H), 8.94 (d, 1H), 8.11 (d, 2H), 7.85 (dd, 1H), 7.41 (dd, 1H), 6.23 (s, 2H), 2.79 (s, 3H). LCMS (method A): [MH]$^+$=323, t$_R$=2.23 min.

(E)-2-(1-(1-((7-Fluoroquinolin-6-yl)methyl)-1H-[1,2,3]triazolo[4,5-b]pyrazin-6-yl)ethylidene)hydrazinecarboxamide (Example 72)

To a solution of 1-[3-(7-fluoro-quinolin-6-ylmethyl)-3H-[1,2,3]triazolo[4,5-b]pyrazin-5-yl]-ethanone (30.0 mg, 0.09 mmol) in MeOH (10 mL), was added hydrazinecarboxamide hydrochloride (31.0 mg, 0.28 mmol). The mixture was heated at 45° C. and stirred overnight. The solvent was removed under reduced pressure. The residue was purified by silica gel column chromatography with gradient (DCM:MeOH=10:1) to give the title compound as a white solid (25.0 mg, 67%). $^1$H-NMR (400 MHz, DMSO-d$_6$) δ ppm 9.91 (s, 1H), 9.85 (s, 1H), 8.93 (dd, 1H), 8.42 (d, 1H), 8.185 (d, 1H), 7.83 (d, 1H), 7.54 (dd, 1H), 6.20 (s, 2H), 2.28 (s, 3H). LCMS (method A): [MH]$^+$=380, t$_R$=1.98 min.

Example 73

Acetic acid [1-[3-(7-fluoro-quinolin-6-ylmethyl)-3H-[1,2,3]triazolo[4,5-b]pyrazin-5-yl]-eth-(E)-ylidene]-hydrazide

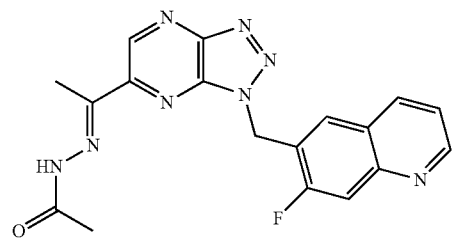 [SMILES: CC(=O)N/N=C(\C)c1cnc2nnn(Cc3cc4cccnc4cc3F)c2n1]

The title compound (30.5 mg, 82%) was synthesized from 1-[3-(7-fluoro-quinolin-6-ylmethyl)-3H-[1,2,3]triazolo[4,5-b]pyrazin-5-yl]-ethanone (30.0 mg, 0.09 mmol) and acetic acid hydrazide (23.0 mg, 0.28 mmol) using the same procedure as described in the synthesis of example 72. $^1$H-NMR (400 MHz, DMSO-d$_6$) δ ppm 10.83 (bs, 1H), 9.46 (s, 1H), 8.93 (dd, 1H), 8.40 (d, 1H), 8.19 (d, 1H), 7.81 (d, 1H), 7.53 (dd, 1H), 6.22 (s, 2H), 2.34, 2.14 (s, 6H). LCMS (method A): [MH]$^+$=379, t$_R$=2.07 min.

Example 74

1N'-[1-[3-(7-Fluoro-quinolin-6-ylmethyl)-3H-[1,2,3]triazolo[4,5-b]pyrazin-5-yl]-eth-(E)-ylidene]-hydrazinecarboxylic acid methyl ester

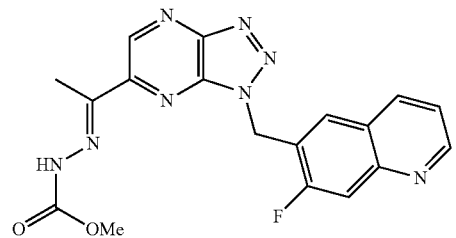 [SMILES: COC(=O)N/N=C(\C)c1cnc2nnn(Cc3cc4cccnc4cc3F)c2n1]

The title compound (29.9 mg, 77%) was synthesized from 1-[3-(7-fluoro-quinolin-6-ylmethyl)-3H-[1,2,3]triazolo[4,5-b]pyrazin-5-yl]-ethanone (30.0 mg, 0.09 mmol) and hydrazinecarboxylic acid methyl ester (25.2 mg, 0.28 mmol) using the same procedure as described in the synthesis of example 72. $^1$H-NMR (400 MHz, DMSO-d$_6$) δ ppm 10.78 (bs, 1H), 9.38 (s, 1H), 8.93 (dd, 1H), 8.41 (d, 1H), 8.18 (d, 1H), 7.83 (d, 1H), 7.54 (dd, 1H), 6.22 (s, 2H), 3.78 (s, 3H), 2.31 (s, 3H). LCMS (method E): [MH]⁺=395, $t_R$=4.64 min.

Example 75

Isonicotinic acid [1-[3-(7-fluoro-quinolin-6-ylmethyl)-3H-[1,2,3]triazolo[4,5-b]pyrazin-5-yl]-eth-(E)-ylidene]-hydrazide

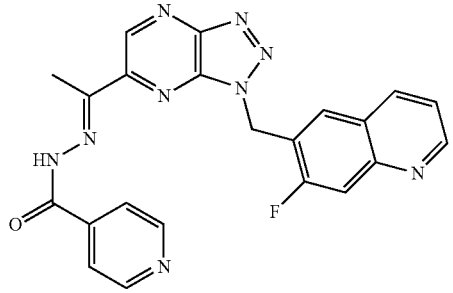 [SMILES: C/C(=N\NC(=O)c1ccncc1)c1cnc2nnn(Cc3cc4cccnc4cc3F)c2n1]

The title compound (27.9 mg, 64%) was synthesized from 1-[3-(7-fluoro-quinolin-6-ylmethyl)-3H-[1,2,3]triazolo[4,5-b]pyrazin-5-yl]-ethanone (30.0 mg, 0.09 mmol) and isonicotinic acid hydrazide (38.3 mg, 0.28 mmol) using the same procedure as described in the synthesis of example 72. ¹H-NMR (400 MHz, DMSO-d₆) δ ppm 11.75, 11.39 (bs, 1H), 9.51 (s, 1H), 8.93 (dd, 1H), 8.79 (m, 2H), 8.42 (d, 1H), 8.20 (d, 1H), 7.836 (m, 3H), 7.54 (dd, 1H), 6.25 (s, 2H), 2.49 (s, 3H). LCMS (method E): [MH]⁺=442, $t_R$=4.59 min.

Example 76

1-[1-[3-(7-Fluoro-quinolin-6-ylmethyl)-3H-[1,2,3]triazolo[4,5-b]pyrazin-5-yl]-eth-(E)-ylideneamino]-imidazolidine-2,4-dione

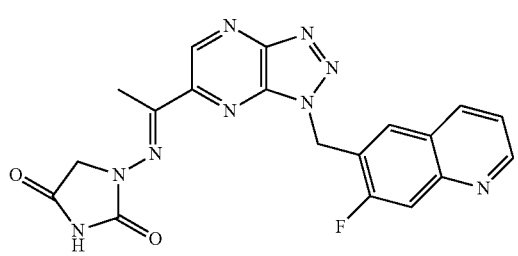 [SMILES: C/C(=N\N1CC(=O)NC1=O)c1cnc2nnn(Cc3cc4cccnc4cc3F)c2n1]

The title compound (18.0 mg, 66%) was synthesized from 1-[3-(7-fluoro-quinolin-6-ylmethyl)-3H-[1,2,3]triazolo[4,5-b]pyrazin-5-yl]-ethanone (20.0 mg, 0.06 mmol) and 1-amino-imidazolidine-2,4-dione (28.2 mg, 0.19 mmol) using the same procedure as described in the synthesis of example 72. ¹H-NMR (400 MHz, DMSO-d₆) δ ppm 11.45 (bs, 1H), 9.41 (s, 1H), 8.93 (dd, 1H), 8.42 (d, 1H), 8.21 (d, 1H), 7.83 (d, 1H), 7.54 (dd, 1H), 6.26 (s, 2H), 4.56 (s, 2H), 2.45 (s, 3H). LCMS (method B): [MH]⁺=420, $t_R$=1.95 min.

Example 77

Propionic acid [1-[3-(7-fluoro-quinolin-6-ylmethyl)-3H-[1,2,3]triazolo[4,5-b]pyrazin-5-yl]-eth-(E)-ylidene]-hydrazide

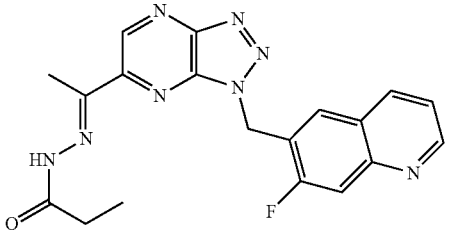 [SMILES: CCC(=O)N/N=C(\C)c1cnc2nnn(Cc3cc4cccnc4cc3F)c2n1]

The title compound (28.5 mg, 74%) was synthesized from 1-[3-(7-fluoro-quinolin-6-ylmethyl)-3H-[1,2,3]triazolo[4,5-b]pyrazin-5-yl]-ethanone (30.0 mg, 0.09 mmol) and propionic acid hydrazide (24.6 mg, 0.28 mmol) using the same procedure as described in the synthesis of example 72. ¹H-NMR (400 MHz, DMSO-d₆) δ ppm 10.93, 10.76 (bs, 1H), 9.45 (s, 1H), 8.92 (dd, 1H), 8.41 (d, 1H), 8.18 (d, 1H), 7.83 (d, 1H), 7.53 (dd, 1H), 6.22 (s, 2H), 2.79 (q, 2H), 2.31 (s, 3H), 1.09 (t, 3H). LCMS (method E): [MH]⁺=393, $t_R$=4.78 min.

Example 78

Nicotinic acid [1-[3-(7-fluoro-quinolin-6-ylmethyl)-3H-[1,2,3]triazolo[4,5-b]pyrazin-5-yl]-eth-(E)-ylidene]-hydrazide

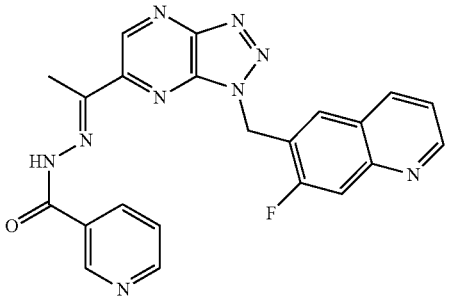 [SMILES: C/C(=N\NC(=O)c1cccnc1)c1cnc2nnn(Cc3cc4cccnc4cc3F)c2n1]

The title compound (17.0 mg, 59%) was synthesized from 1-[3-(7-fluoro-quinolin-6-ylmethyl)-3H-[1,2,3]triazolo[4,5-b]pyrazin-5-yl]-ethanone (20.0 mg, 0.06 mmol) and nicotinic acid hydrazide (17.0 mg, 0.12 mmol) using the same procedure as described in the synthesis of example 72. ¹H-NMR (400 MHz, DMSO-d₆) δ ppm 11.64, 11.38 (bs, 1H), 9.52 (s, 1H), 9.05 (s, 1H), 8.93 (dd, 1H), 8.78 (d, 1H), 8.42 (d, 1H)8.20 (d, 1H), 7.84 (d, 1H), 7.56 (m, 2H), 6.26 (s, 2H), 2.49 (s, 3H). LCMS (method A): [MH]⁺=442, $t_R$=2.10 min. ,

Example 79

1-[1-[3-(7-Fluoro-quinolin-6-ylmethyl)-3H-[1,2,3]triazolo[4,5-b]pyrazin-5-yl]-eth-(E)-ylideneamino]-imidazolidin-2-one

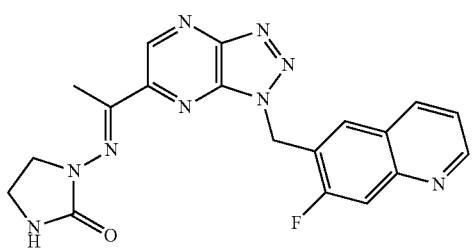 [SMILES: C/C(=N\N1CCNC1=O)c1cnc2nnn(Cc3cc4cccnc4cc3F)c2n1]

The title compound (18.0 mg, 66%) was synthesized from 1-[3-(7-fluoro-quinolin-6-ylmethyl)-3H-[1,2,3]triazolo[4,5-b]pyrazin-5-yl]-ethanone (20.0 mg, 0.06 mmol) and 1-amino-imidazolidin-2-one (28.2 mg, 0.19 mmol) using the same procedure as described in the synthesis of example 72. $^1$H-NMR (400 MHz, DMSO-$d_6$) δ ppm 9.42 (s, 1H), 8.93 (dd, 1H), 8.41 (d, 1H), 8.20 (d, 1H), 7.83 (d, 1H), 7.54 (dd, 1H), 7.38 (s, 1H), 6.25 (s, 2H), 3.86 (t, 2H), 3.42 (t, 2H), 2.38 (s, 3H). LCMS (method A): [MH]$^+$=401, $t_R$=2.01 min.

Example 80

(E)-2-(1-(3-((6-fluoro-1-methyl-1H-indazol-5-yl)methyl)imidazo[1,2-b]pyridazin-6-yl)propylidene)hydrazinecarboxamide

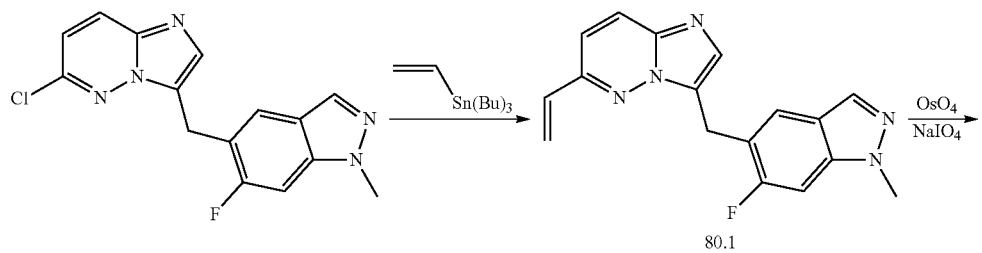

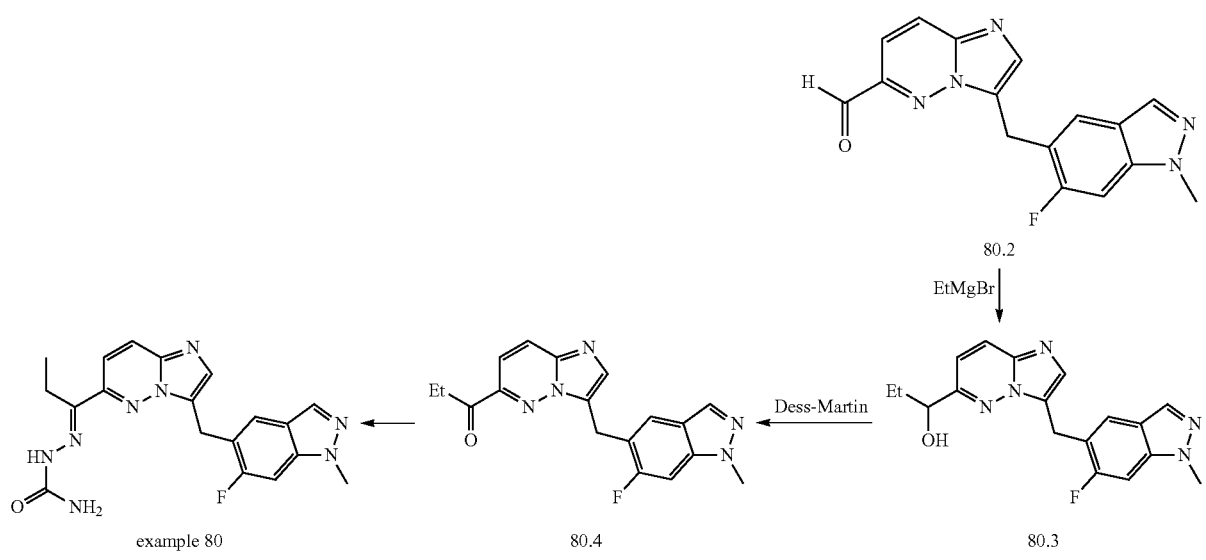

3-((6-Fluoro-1-methyl-1H-indazol-5-yl)methyl)-6-vinylimidazo[1,2-b]pyridazine (80.1)

To a degassed solution of 6-chloro-3-((6-fluoro-1-methyl-1H-indazol-5-yl)methyl)imidazo[1,2-b]pyridazine (400 mg, 1.267 mmol), was added Pd(Ph$_3$P)$_4$ (220 mg, 0.190 mmol) and tributyl(vinyl)stannane (422 mg, 1.330 mmol). The reaction mixture was heated to 120° C. for overnight. Then the reaction was quenched with NH$_4$Cl(aq), extracted with DCM, dried over Na$_2$SO$_4$ and concentrated in vacuo to give a residue, which was purified by silica gel column chromatography with gradient Hex:EA to give 3-((6-fluoro-1-methyl-1H-indazol-5-yl)methyl)-6-vinylimidazo[1,2-b]pyridazine (168 mg, 43%). $^1$H-NMR (400 MHz, DMSO-d$_6$) δ ppm 8.09 (d, 1H), 7.97 (s, 1H), 7.63 (d, 1H), 7.55 (d, 1H), 7.54 (d, 1H), 7.50 (s, 1H), 6.84 (dd, 1H), 6.31 (d, 1H), 5.72 (d, 1H), 4.37 (s, 2H), 3.98 (s, 3H). LCMS (method B): [MH]$^+$=308, t$_R$=2.49 min.

3-((6-Fluoro-1-methyl-1H-indazol-5-yl)methyl)imidazo[1,2-b]pyridazine-6-carbaldehyde (80.2)

To a mixture of 3-((6-fluoro-1-methyl-1H-indazol-5-yl)methyl)-6-vinylimidazo[1,2-b]pyridazine (50 mg, 0.163 mmol) osmium(VIII) oxide (103 mg, 8.13 µmol), was added a solution of NMO (29.5 mg, 0.252 mmol) in acetone (2 ml) and H$_2$O (0.16 ml). The reaction mixture was heated to 46° C. After stirring for 4 h, the solvent was removed and a mixture of THF (6 ml) and H$_2$O (1.5 ml) was added to dissolve the residue, then sodium periodate (69.6 mg, 0.325 mmol) was added and the resulting mixture was stirred at 46° C. for 12 h. The reaction mixture was then quenched with Na$_2$SO$_3$(aq), extracted with DCM, dried over Na$_2$SO$_4$, filtered through Celite and concentrated in vacuo to give a residue, which was purified by silica gel column chromatography with gradient Hex:EA to give 3-((6-fluoro-1-methyl-1H-indazol-5-yl)methyl)imidazo[1,2-b]pyridazine-6-carbaldehyde (20 mg), yield 38%. $^1$H-NMR (400 MHz, CDCl$_3$) δ ppm 10.09 (s, 1H), 8.07 (dd, 1H), 7.89 (d, 1H), 7.74 (s, 1H), 7.63 (m, 2H), 7.10 (d, 1H), 4.54 (s, 2H), 4.03 (s, 3H). LCMS (method A): [MH]$^+$=310, t$_R$=3.95 min.

1-(3-((6-Fluoro-1-methyl-1H-indazol-5-yl)methyl)imidazo[1,2-b]pyridazin-6-yl)propan-1-ol (80.3)

To a solution of 3-((6-fluoro-1-methyl-1H-indazol-5-yl)methyl)imidazo[1,2-b]pyridazine-6-carbaldehyde (52 mg, 0.168 mmol) in THF (4 mL) at 0° C., was added a solution of ethylmagnesium bromide in THF (1M, 0.336 mL) dropwise. After stirring for 16 h, the reaction mixture was quenched with NH$_4$Cl(aq), extracted with EtOAc, dried over Na$_2$SO$_4$. Filtered through Celite and concentrated in vacuo to give a crude product (14 mg, 10%). LCMS (method B): [MH]$^+$=340, t$_R$=2.04 min.

1-(3-((6-fluoro-1-methyl-1H-indazol-5-yl)methyl)imidazo[1,2-b]pyridazin-6-yl)propan-1-one (80.4)

To a solution 1-(3-((6-fluoro-1-methyl-1H-indazol-5-yl)methyl)imidazo[1,2-b]pyridazin-6-yl)propan-1-ol (13 mg, 0.015 mmol) in DCM (3 mL), was added TEA (0.011 ml, 0.079 mmol) and Dess-Martin periodinane (40 mg, 0.094 mmol). After stirring at rt for 10 min, the reaction was quenched with Na$_2$SO$_3$(aq), extracted with DCM. The organic layer was separated, dried over Na$_2$SO$_4$ and concentrated in vacuo to give a residue, which was purified by silica gel column chromatography with gradient Hex:EA to give 1-(3-((6-fluoro-1-methyl-1H-indazol-5-yl)methyl)imidazo[1,2-b]pyridazin-6-yl)propan-1-one (4 mg, 74%). LCMS (method A): [MH]$^+$=338, t$_R$=5.08 min.

(E)-2-(1-(3-((6-fluoro-1-methyl-1H-indazol-5-yl)methyl)imidazo[1,2-b]pyridazin-6-yl)propylidene)hydrazinecarboxamide (Example 80)

The title compound was prepared as a white solid in analogy to the synthesis of example 1 from 1-(3-((6-fluoro-1-methyl-1H-indazol-5-yl)methyl)imidazo[1,2-b]pyridazin-6-yl)propan-1-one. $^1$H-NMR (400 MHz, DMSO-d$_6$) δ ppm 9.89 (s, 1H), 8.16 (d, 1H), 7.95 (m, 2H), 7.67 (d, 1H), 7.61 (s, 1H), 7.52 (d, 1H), 4.40 (s, 2H), 3.96 (s, 3H), 2.85 (q, 2H), 0.91 (t, 3H). LCMS (method B): [MH]$^+$=395, t$_R$=1.72 min.

Example 81

(E)-2-(1-(7-(quinolin-6-ylmethyl)imidazo[1,2-b][1,2,4]triazin-2-yl)ethylidene)hydrazinecarboxamide

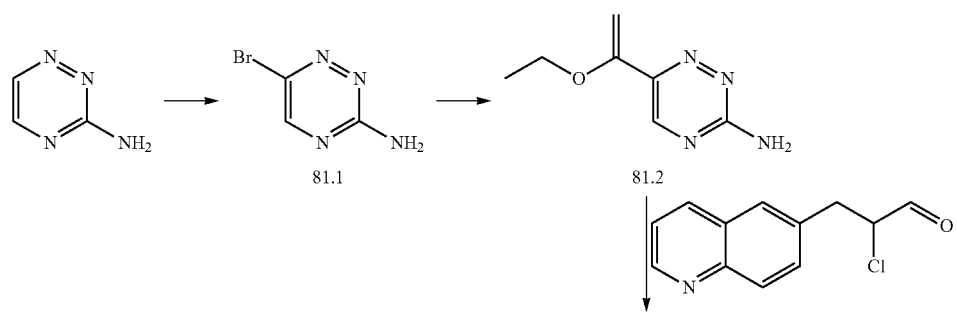

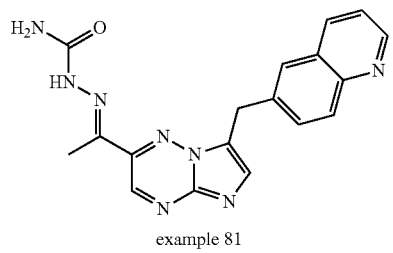
example 81

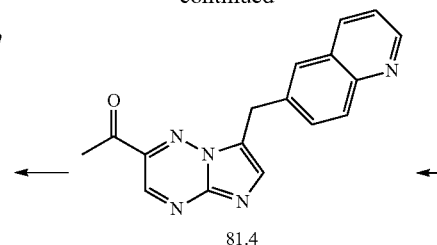
81.4

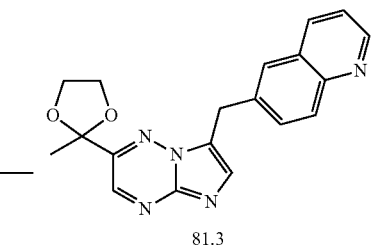
81.3

-continued

6-Bromo-1,2,4-triazin-3-amine (81.1)

A mixture of 3-amino-1,2,4-triazine (50.0 g, 521 mmol) in water (6000 mL) was cooled to 0-5° C. The bromine (70 mL, 1.30 mmol) was added dropwise to the reaction mixture for 1 h. Then the mixture was stirred overnight at 0-10° C. A satured aqueous $Na_2SO_3$ solution was added to the reaction and the mixture was neutralized to pH=12 with a 6 N aqueous NaOH solution. The mixture was extracted with dichloromethane, dried over $Na_2SO_4$. The solvent was removed in vacuo to afford 50.0 g (54%) of the title compound as a yellow solid. $^1$H-NMR (400 MHz, $d_6$-DMSO) δ ppm 8.40 (s, 1H), 7.47 (s, 2H). LCMS (method B): [MH]$^+$=175/177, $t_R$=0.328 min.

6-(1-Ethoxyvinyl)-1,2,4-triazin-3-amine (81.2)

A solution of 6-bromo-1,2,4-triazin-3-amine (780 mg, 4.46 mmol) in N,N-dimethylformamide (50 mL) was treated with tetrakis(triphenylphosphine)palladium (0) (258 mg, 0.22 mmol), N,N-diisopropylethyl amine (2284 mg, 11.14 mmol), lithium chloride (661 mg, 15.6 mmol), and vinyltri-n-butyltin (2093 mg, 5.79 mmol), and the reaction was heated at 120° C. for 2 h. The reaction mixture was cooled to room temperature and concentrated the solvent in vacuo. The residue was diluted with dichloromethane and washed with aqueous KF solution. The crude product was purified by flash chromatography in silica gel eluting with a ethyl acetate/hexane gradient to afford 380 mg (51%) of the title compound as a yellow solid. $^1$H-NMR (400 MHz, CDCl$_3$) δ ppm 8.48 (s, 1H), 5.41-5.39 (m, 3H), 4.36 (s, 1H), 3.98 (q, 2H), 1.43 (t, 2H).

6-((2-(2-Methyl-1,3-dioxolan-2-yl)imidazo[1,2-b][1,2,4]triazin-7-yl)methyl)quinoline (81.3)

A solution of 6-(1-ethoxyvinyl)-1,2,4-triazin-3-amine (120 mg, 0.72 mmol), 2-chloro-3-(quinolin-3-yl)propanal (317 mg, 1.44 mmol) in ethylene glycol (8 mL) was stirred at 140° C. for 2 h. The reaction mixture was cooled to room temperature, neutralized with saturated aqueous $Na_2CO_3$ solution and diluted with water, extracted with ethyl acetate, dried over $Na_2SO_4$. The solvent was removed in vacuo and the residue was purified by flash chromatography in silica gel eluting with a ethyl acetate/hexane gradient to afford 135 mg (54%) of the title compound as yellow solid. LCMS (method B): [MH]$^+$=348, $t_R$=2.03 min.

1-(7-(Quinolin-6-ylmethyl)imidazo[1,2-b][1,2,4]triazin-2-yl)ethanone (81.4)

A solution of 6-((2-(2-methyl-1,3-dioxolan-2-yl)imidazo[1,2-b][1,2,4]triazin-7-yl)methyl)quinoline (130 mg, 0.37 mmol) in 3 N HCl (5 mL) was stirred at 90° C. for 0.5 h. The reaction mixture was cooled to room temperature, neutralized with saturated aqueous $Na_2CO_3$ solution, extracted with ethyl acetate, dried over $Na_2SO_4$. The solvent was removed in vacuo to afford 85 mg (75%) of the title compound as yellow solid. $^1$H-NMR (400 MHz, CDCl$_3$) δ ppm 9.06 (s, 1H), 8.91 (d, 1H), 8.12 (t, 2H), 8.04 (s, 1H), 7.74-7.71 (m, 2H), 7.48-7.39 (m, 1H), 4.60 (s, 2H), 2.70 (s, 3H). LCMS (method B): [MH]$^+$=304, $t_R$=1.81 min.

C-Met Enzyme Assay

A number of compounds of the present invention were assayed in an antibody based kinase phosphorylation assay as follows.

EPK cMET Profiling Assay:

The EPK kinase assay for cMET receptor tyrosine kinase was developed, using the purified recombinant GST-fusion protein, containing the cytoplasmic domain of the enzyme. GST-cMET (969-1390) was purified by affinity chromatography.

The kinase assay is based on the LanthaScreen™ technology. LanthaScreen™ is the detection of Time-Resolved Fluorescence Resonance Energy Transfer (TR-FRET) using lanthanide chelates to measure interactions between various binding partners. In a TR-FRET kinase assay, a long-lifetime lanthanide donor species is conjugated to an antibody that specifically binds to a phosphorylated product of a kinase reaction that is labeled with a suitable acceptor fluorophore. This antibody-mediated interaction brings the lanthanide donor and the acceptor into proximity such that resonance energy transfer can take place, resulting in a detectible increase in the FRET signal.

The kinase reactions were performed in 384 well microtiter plates in a total reaction volume of 10.05 μL. The assay plates were prepared with 0.05 μL per well of test compound in the appropriate test concentration, as described under "preparation of compound dilutions". The reactions were started by combining 5 μL of ATP solution with 5 μL of enzyme-substrate mix (consisting of kinase and substrate). The final concentrations in the kinase reactions were 25 mM Tris/HCl, 1 mM DTT, 0.025% Tween20, 10 μM sodium orthovanadate, 0.25% BSA, 0.5% DMSO, 10 mM MgCl$_2$, 3 mM MnCl$_2$, 2 μM ATP, 50 nM Fluorescein-PolyEAY, and 0.3 nM enzyme.

The reactions were incubated for 60 minutes at room temperature and stopped by adding 5 μL of stop buffer (50 mM EDTA, 0.04% NP40, 20 mM Tris/HCl).

Subsequently 5 μL of detection mix (50 mM Tris/HCl, 2 mM DTT, 0.05% Tween20, 20 μM sodium orthovanadate, 1% BSA, 1 nM Tb-PY20 antibody) were added to the stopped reactions. After 45 minutes incubation in dark at room temperature, the plates were measured in a Perkinelmer Envision fluorescence reader. The effect of compound on the enzymatic activity was in all assays obtained from the linear progress curves and determined from one reading (end point measurement).

Results are summarized in the Table below. "Active" compounds of the invention have an IC50 in this enzyme assay of less than 5000 nM, in particular less than 3500 nM, preferably less than 1000 nM, more preferably less than 500 nM and most preferably less than 10 nM.

GTL16 Cell Viability Assay:

GTL16 cell line is derived from a gastric cancer patient. GTL16 expresses high level of cMet receptor tyrosine kinase due to the gene amplification. The growth of GTL16 is highly dependent on cMet kinase activity; hence it is used as a cell base assay to monitor the cellular activity of the cMet kinase inhibitors.

GTL16 cells were seeded in DMEM medium with 10% FBS and 1% Pene. & Strep. at 5000 cells/well/90 μL in 96 well plate and incubated overnight for attachment at 37° C. in 5% $CO_2$ incubator. 10-fold serials dilutions of compounds were added to the cell as 10 μL/well. The final assay volume was 100 μl/well. The assay plates were incubated at 37° C. in 5% $CO_2$ incubator for 24 hours. The viability of cells was measured using the CellTiter Glo (Cat# G7573 Promega) according to the protocol suggested by the vender. Briefly, the plates were cooled at room temperature for 10 mins and 100 μl of CellTiter Glo reagent was added into each well. Plates were shaken for 10 mins. The chemiluminescent light unit was read in Envision from Perkin Elmer. All the tests were run at triplicates. The $IC_{50}$ was calculated using Spotfire software.

TABLE 1

Inhibitory Activity of Compounds

| Example number | cMet enzyme ($IC_{50}$ nM) |
|---|---|
| 1 | 1 |
| 2 | 18 |
| 3 | 3 |
| 4 | 267 |
| 5 | 18 |
| 6 | 83 |
| 7 | 2,453 |
| 8 | 1 |
| 9 | 61 |
| 10 | 3 |
| 11 | 1 |
| 12 | 590 |
| 13 | 250 |
| 14 | 28 |
| 15 | 932 |
| 16 | 6 |
| 17 | 1 |
| 18 | 1 |
| 19 | 2 |
| 20 | 0.4 |
| 21 | 3 |
| 22 | 9 |
| 23 | 9 |
| 24 | 159 |
| 25 | 2 |
| 26 | 24 |
| 27 | 14 |
| 28 | 66 |
| 29 | 6 |
| 30 | 0.4 |
| 30 | 21 |
| 31 | 7 |
| 32 | 3 |
| 33 | 0.7 |
| 34 | 10 |
| 35 | 21 |
| 36 | 224 |
| 37 | 1 |
| 38 | 4 |
| 39 | 11 |

TABLE 1-continued

Inhibitory Activity of Compounds

| Example number | cMet enzyme ($IC_{50}$ nM) |
|---|---|
| 40 | 0.3 |
| 41 | 185 |
| 42 | 4 |
| 43 | 21 |
| 44 | 1 |
| 45 | 4 |
| 46 | 0.2 |
| 46 | 9 |
| 47 | 260 |
| 48 | 2,983 |
| 49 | 0.5 |
| 50 | 77 |
| 51 | 131 |
| 52 | 3 |
| 53 | 20 |
| 54 | 119 |
| 55 | 4 |
| 56 | 7 |
| 57 | 73 |
| 58 | 14 |
| 59 | 5 |
| 60 | 0.8 |
| 61 | 191 |
| 62 | 685 |
| 63 | 66 |
| 64 | 28 |
| 65 | 0.2 |
| 66 | 0.3 |
| 67 | 3 |
| 68 | 12 |
| 69 | 5 |
| 70 | 16 |
| 71 | 17 |
| 72 | 0.2 |
| 73 | 0.4 |
| 74 | 1 |
| 75 | 0.5 |
| 76 | 0.9 |
| 77 | 9 |
| 78 | 1 |
| 79 | 9 |
| 80 | 4 |
| 81 | 42 |

The invention claimed is:

1. A compound of formula (I)

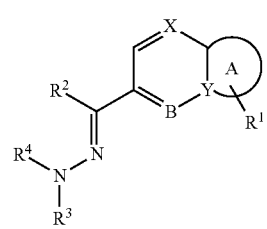

wherein

Y is N;

X is CH;

B is N;

A is a ring;

such that when X is CH and B is N, ring A is ring Ai or ring Aii;

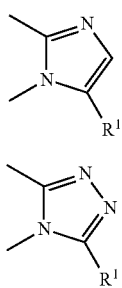

R[1] is a group i:

wherein R[5] is heteroaryl[1],
heteroaryl[1] is a 9- or 10-membered, unsaturated or partially unsaturated bicyclic group comprising 1, 2, 3 or 4 ring heteroatoms independently selected from N, O and S, wherein the total number of ring S atoms does not exceed 1, and the total number of ring O atoms does not exceed 1, wherein heteroaryl[1] is optionally substituted by one or more substituents independently selected from halo, OH, and $(C_1-C_3)$alkyl, said $(C_1-C_3)$alkyl being optionally substituted by one or more substituents independently selected from OH and halo;
R[6] is hydrogen, OH, methyl or halo;
R[7] is hydrogen, halo, or $(C_1-C_3)$alkyl, wherein said $(C_1-C_3)$alkyl is optionally substituted by one or more substituents independently selected from OH and halo;
or R[6] and R[7], together with the carbon to which they are attached form cyclopropyl, wherein said cyclopropyl is optionally substituted by methyl;
R[2] is hydrogen, NH$_2$, or $(C_1-C_4)$alkyl, wherein said $(C_1-C_4)$alkyl is optionally substituted by one or more substituents independently selected from OH, NH$_2$ and halo;
R[3] is hydrogen, —CONH$_2$, —CONH($C_1$-$C_4$)alkyl, —CONHphenyl, wherein the phenyl of said CONHphenyl is optionally substituted by one or more halo, —($C_1$-$C_4$)alkyl, —CO($C_1$-$C_4$)alkyl, —CO$_2$($C_1$-$C_4$)alkyl, phenyl, heteroaryl[2], —COheteroaryl[2], —CSNH$_2$, —CSNH($C_1$-$C_4$)alkyl, —CSNHbenzyl, —SO$_2$($C_1$-$C_4$)alkyl or —COCH$_2$heterocyclyl[1], said heterocyclyl[1] being optionally substituted by $(C_1-C_3)$alkyl;
heteroaryl[2] is a 5- to 10-membered unsaturated or partially unsaturated monocyclic or bicyclic group comprising 1, 2, 3 or 4 ring heteroatoms independently selected from N, O and S, wherein the total number of ring S atoms does not exceed 1, and the total number of ring O atoms does not exceed 1, wherein heteroaryl[2] is optionally substituted by one or more substituents independently selected from halo, OH, and $(C_1-C_3)$alkyl, said $(C_1-C_3)$alkyl being optionally substituted by one or more substituents independently selected from OH and halo;
heterocyclyl[1] means a 5 or 6 membered saturated or partially unsaturated monocyclic group comprising 1 or 2 ring heteroatoms independently selected from N, O and S;

R[4] is hydrogen or $(C_1-C_3)$alkyl;
or R[3] and R[4] together with the nitrogen to which they are attached form a 5 or 6 membered saturated or partially unsaturated monocyclic group comprising 1 ring N atom to which R[3] and R[4] are attached and optionally 1 additional ring heteroatom independently selected from N, O and S, wherein said monocyclic group is substituted by one or two =O substituents;
or a pharmaceutically acceptable salt thereof.

2. The compound or pharmaceutically acceptable salt thereof of claim 1, wherein
B is N;
Y is N;
X is CH;
such that when X is CH, ring A is ring Ai or ring Aii

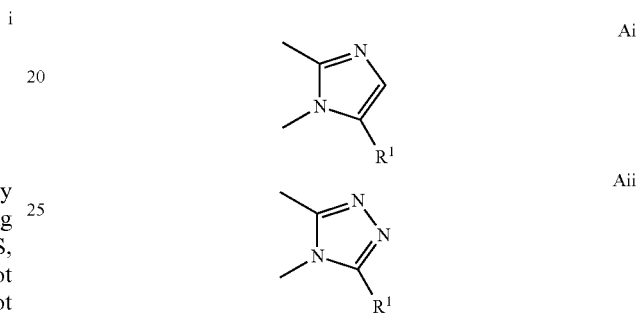

and the remaining substituents are as defined in claim 1.

3. The compound or pharmaceutically acceptable salt thereof of claim 2, wherein R[5] is heteroaryl[3], wherein heteroaryl[3] is a 9- or 10-membered, unsaturated or partially unsaturated bicyclic group comprising 1 or 2 ring N heteroatoms, wherein heteroaryl[3] is optionally substituted by one or more substituents independently selected from halo, OH, and $(C_1-C_3)$alkyl, said $(C_1-C_3)$alkyl being optionally substituted by one or more substituents independently selected from OH and halo.

4. The compound or pharmaceutically acceptable salt thereof of claim 3, wherein R[5] is indazolyl or quinolinyl, optionally substituted by one or more substituents independently selected from halo and $(C_1-C_3)$alkyl.

5. The compound or pharmaceutically acceptable salt thereof of claim 4, wherein R[5] is indazol-5-yl substituted at the 1 position by a methyl substituent and optionally further substituted by one or two fluoro substituents, or R[5] is quinolin-6-yl optionally substituted by one or two fluoro substituents.

6. The compound or pharmaceutically acceptable salt thereof of claim 1, wherein R[6] is hydrogen, deuterium or halo.

7. The compound or pharmaceutically acceptable salt thereof of claim 1, wherein R[7] is hydrogen, deuterium, halo or methyl.

8. The compound or pharmaceutically acceptable salt thereof of claim 1, wherein when R[6] and R[7] are not both hydrogen, the compound of formula (I) is the (S) enantiomer.

9. The compound or pharmaceutically acceptable salt thereof of claim 1, wherein R[2] is hydrogen or methyl.

10. The compound or pharmaceutically acceptable salt thereof of claim 1, wherein R[3] is hydrogen, —CONH$_2$, —CONHCH$_3$, —CONHphenyl, wherein the phenyl of said CONHphenyl is optionally substituted by one or more halo, —($C_1$-$C_4$)alkyl, —COCH$_3$, —CO$_2$CH$_3$, phenyl, benzoxazolyl, heteroaryl[4], —COheteroaryl[4], —CSNH$_2$, —CSNH($C_1$-$C_2$)alkyl, —CSNHbenzyl, —SO$_2$Me, —COCH$_2$-morpholinyl, COCH₂piperidinyl, or —COCH₂piperazinyl, said piperazinyl being optionally substituted by one or more (C₁-C₃)alkyl, and wherein heteroaryl⁴ is a 5 or 6 membered unsaturated or partially unsaturated monocyclic group comprising 1, 2, 3 or 4 ring heteroatoms independently selected from N, O and S, wherein the total number of ring S atoms does not exceed 1, and the total number of ring O atoms does not exceed 1.

11. The compound or pharmaceutically acceptable salt thereof of claim 10, wherein $R^3$ is —CONH₂.

12. The compound or pharmaceutically acceptable salt thereof of claim 1, wherein $R^3$ and $R^4$, together with the nitrogen to which they are attached, form oxazolidinone, oxazolidinedione, imidazolidinone or imidazolidinedione.

13. A method of treating a disorder or condition selected from rheumatoid arthritis and breast cancer which involves administering to a subject in need thereof an effective amount of a compound of formula (I) or a pharmaceutically acceptable salt thereof.

14. A pharmaceutical composition, comprising a compound of claim 1, or a pharmaceutically acceptable salt thereof, and at least one pharmaceutically acceptable carrier or diluent and optionally one or more further therapeutic agents.

15. A compound of claim 1 or a pharmaceutically acceptable salt thereof, in combination with one or more additional therapeutically active agents.

16. A compound, or a pharmaceutically acceptable salt thereof, selected from:

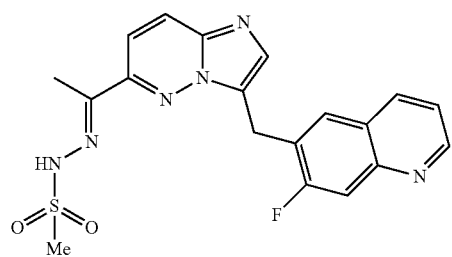

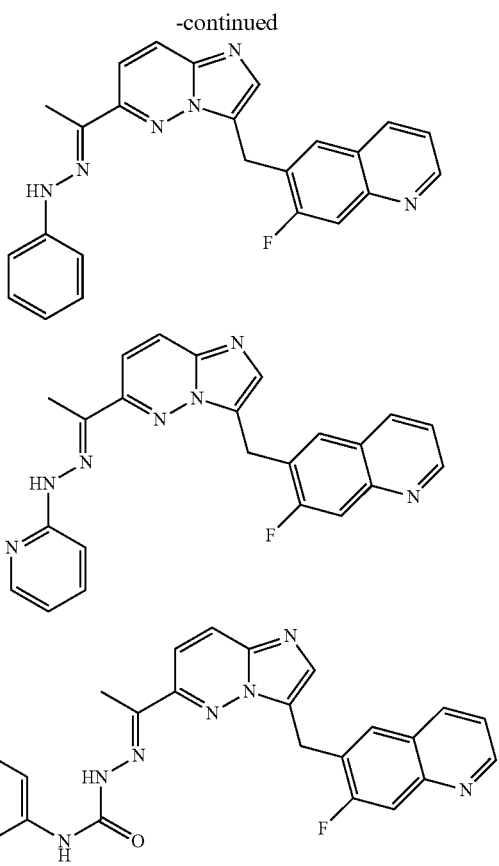

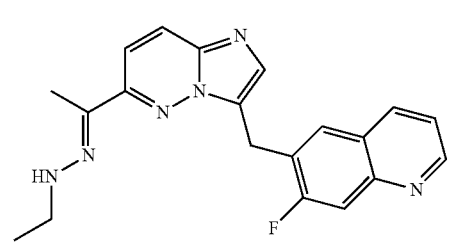

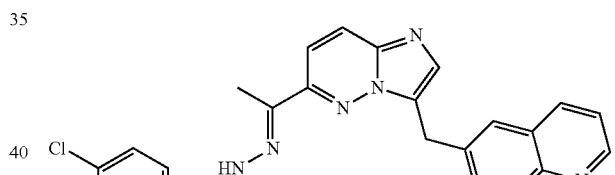

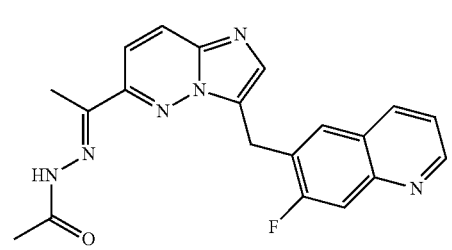

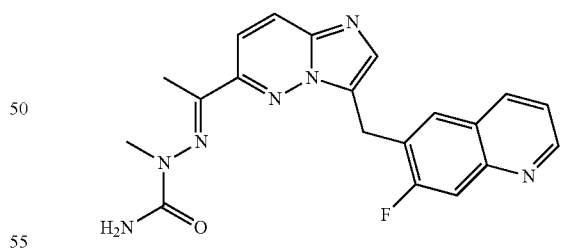

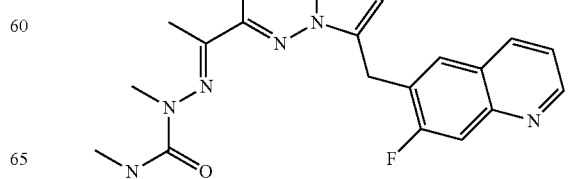

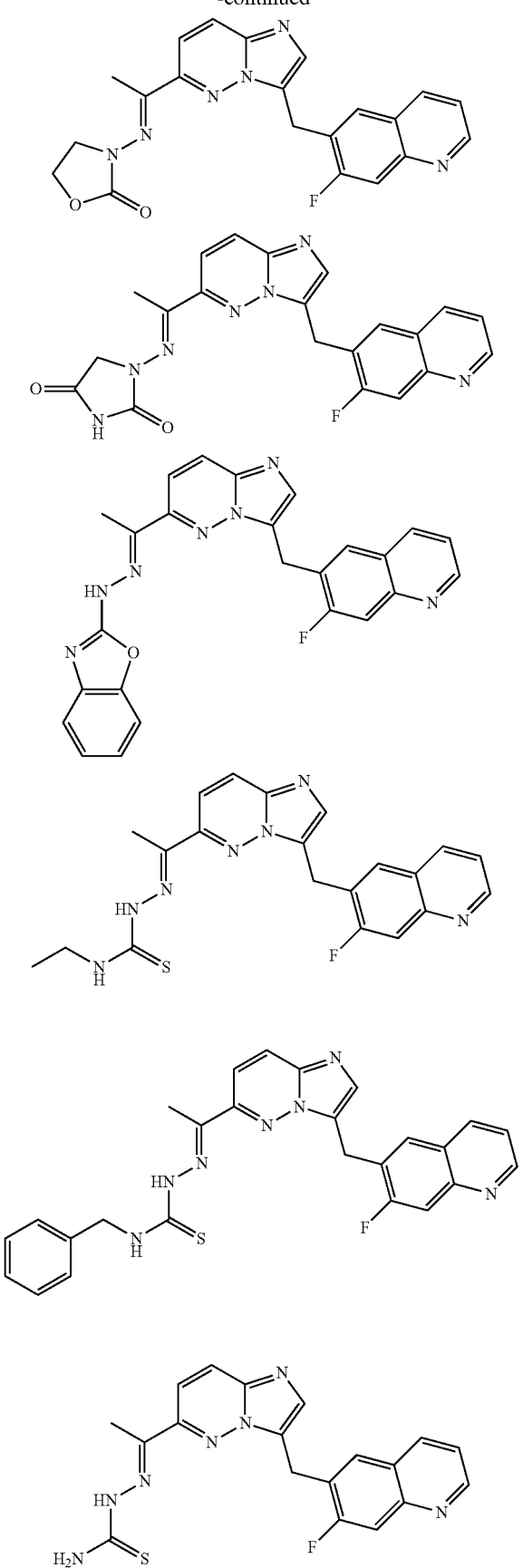
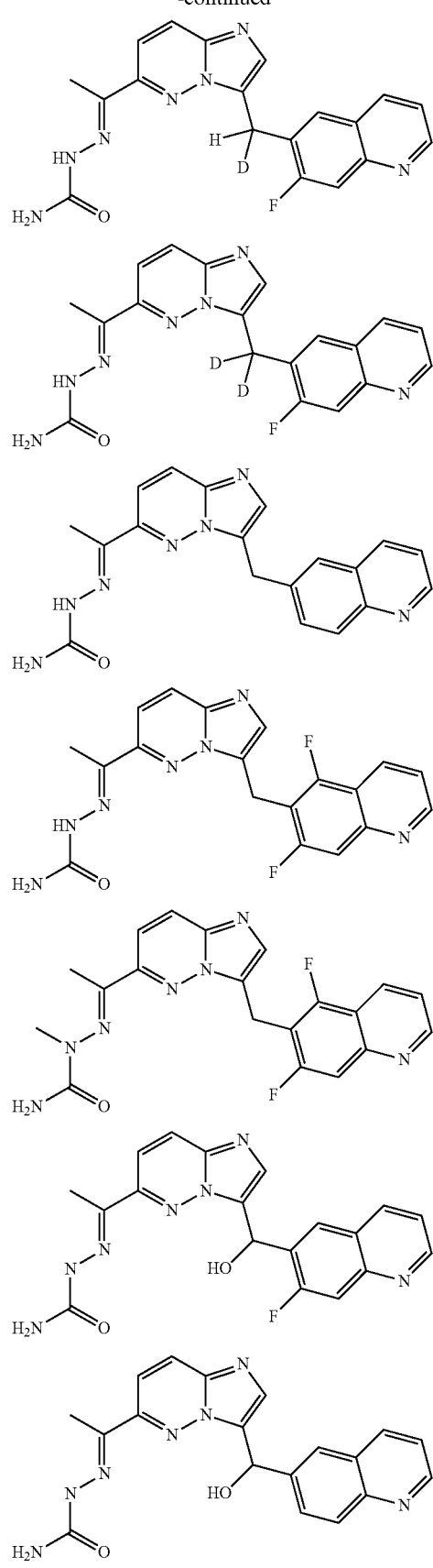

143
-continued
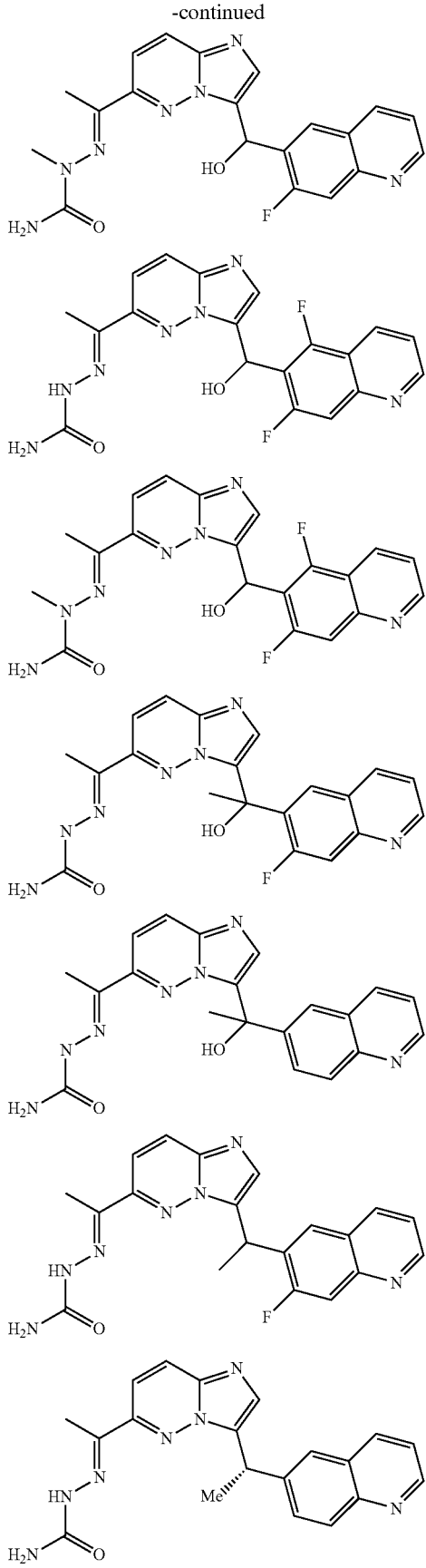
144
-continued
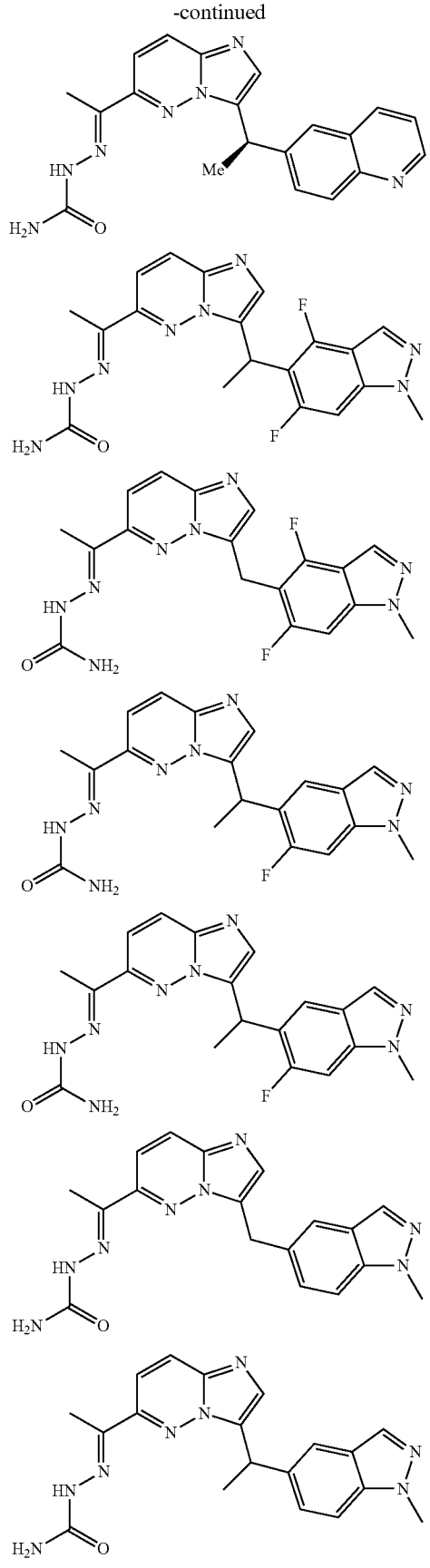

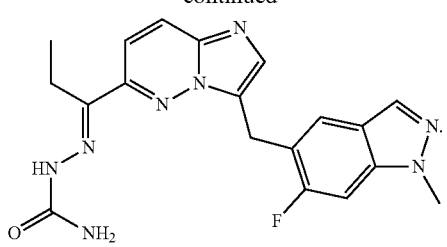
17. A compound, or a pharmaceutically acceptable salt thereof, selected from:
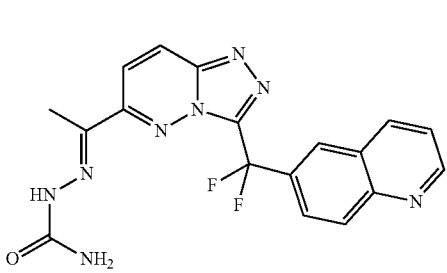
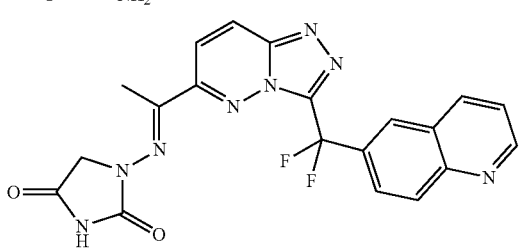
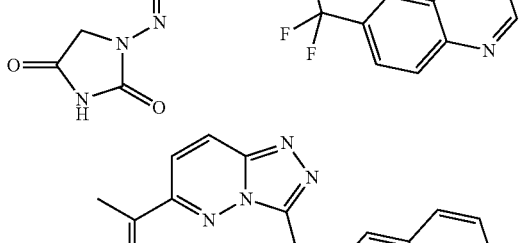
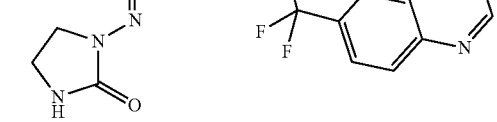
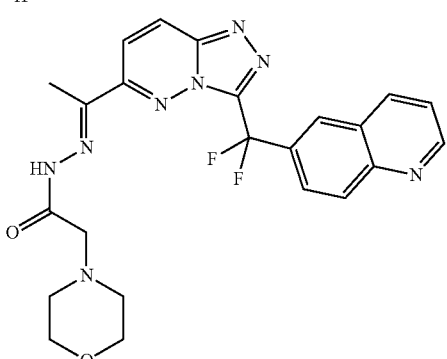
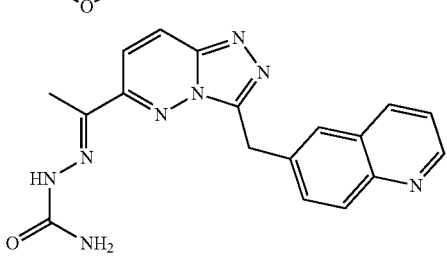
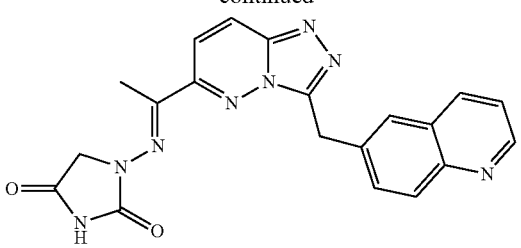
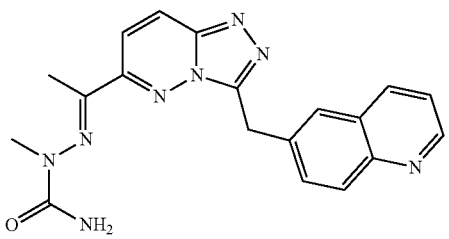
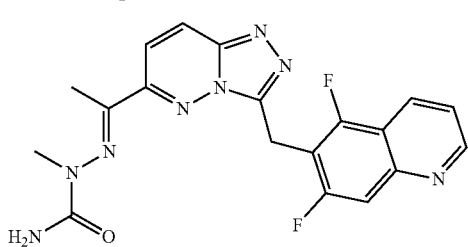
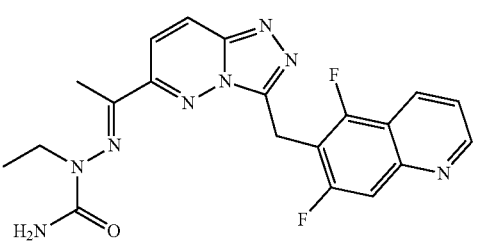
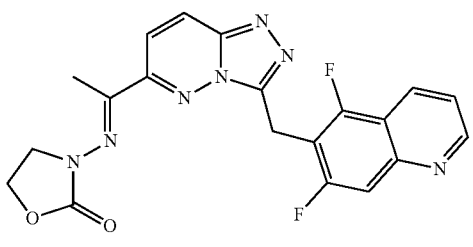
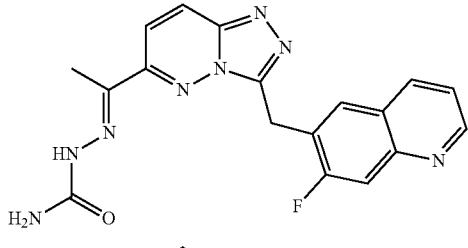
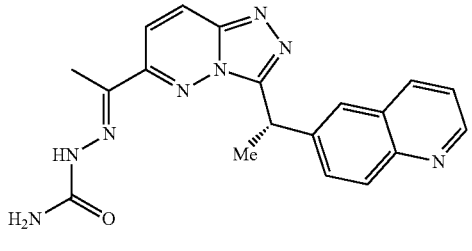

147
-continued
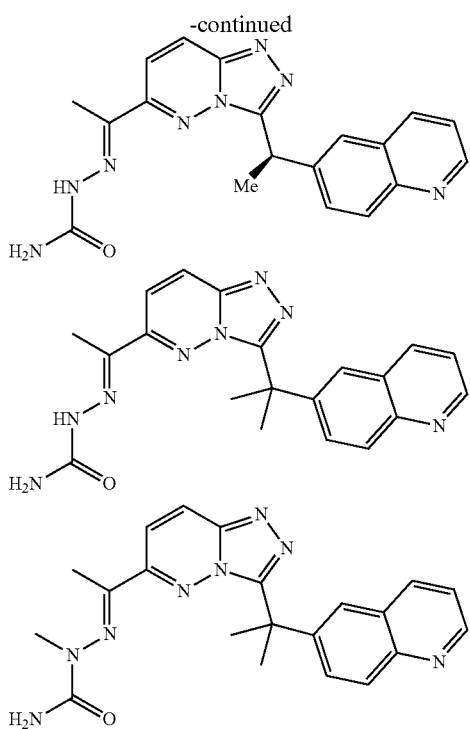
148
-continued
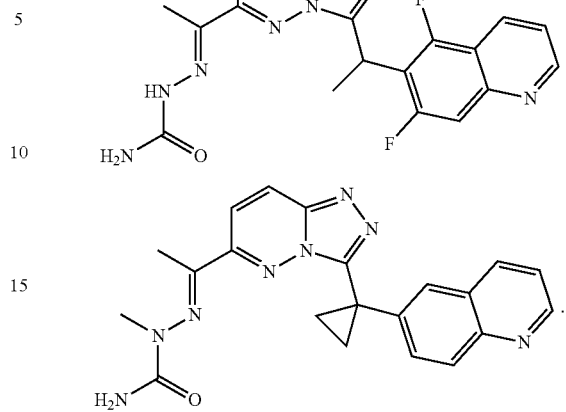
18. A compound that is (E)-2-(1-(3-((7-fluoroquinolin-6-yl)methyl)imidazo[1,2-b]pyridazin-6-yl)ethylidene)-hydrazinecarboxamide or a pharmaceutically acceptable salt thereof.
* * * * *